US008945897B2

(12) United States Patent
Siekmann et al.

(10) Patent No.: US 8,945,897 B2
(45) Date of Patent: Feb. 3, 2015

(54) MATERIALS AND METHODS FOR CONJUGATING A WATER SOLUBLE FATTY ACID DERIVATIVE TO A PROTEIN

(75) Inventors: Juergen Siekmann, Vienna (AT); Richard Sheinecker, Vienna (AT); Hanspeter Rottensteiner, Vienna (AT); Peter Turecek, Klosterneuburg (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 13/329,002

(22) Filed: Dec. 16, 2011

(65) Prior Publication Data
US 2012/0190096 A1    Jul. 26, 2012

Related U.S. Application Data

(63) Continuation-in-part of application No. 12/843,542, filed on Jul. 26, 2010.

(60) Provisional application No. 61/426,356, filed on Dec. 22, 2010.

(51) Int. Cl.
*C12N 9/96* (2006.01)
*C07K 14/475* (2006.01)
*A61K 47/48* (2006.01)

(52) U.S. Cl.
CPC ..... *A61K 47/48038* (2013.01); *A61K 47/48215* (2013.01)
USPC ........... 435/188; 530/350; 530/384; 530/351; 530/383; 530/381

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,356,170 A | 10/1982 | Jennings et al. | |
| 4,367,309 A | 1/1983 | Kondo et al. | |
| 4,757,006 A | 7/1988 | Toole, Jr. et al. | |
| 4,966,999 A | 10/1990 | Coughlin et al. | |
| 4,970,300 A | 11/1990 | Fulton et al. | |
| 5,122,614 A | 6/1992 | Zalipsky | |
| 5,153,265 A | 10/1992 | Shadle et al. | |
| 5,198,349 A | 3/1993 | Kaufman | |
| 5,198,493 A | 3/1993 | Holmberg et al. | |
| 5,250,421 A | 10/1993 | Kaufman et al. | |
| 5,298,643 A | 3/1994 | Greenwald | |
| 5,492,821 A | 2/1996 | Callstrom et al. | |
| 5,621,039 A | 4/1997 | Hallahan et al. | |
| 5,733,873 A | 3/1998 | Osterberg et al. | |
| 5,750,497 A | 5/1998 | Andersen et al. | |
| 5,846,951 A | 12/1998 | Gregoriadis | |
| 5,866,538 A | 2/1999 | Norup et al. | |
| 5,919,766 A | 7/1999 | Osterberg et al. | |
| 5,969,040 A | 10/1999 | Hallahan et al. | |
| 6,011,007 A | 1/2000 | Havelund et al. | |
| 6,037,452 A | 3/2000 | Minamino et al. | |
| 6,048,720 A | 4/2000 | Dalborg et al. | |
| 6,183,738 B1 | 2/2001 | Clark | |
| 6,531,298 B2 | 3/2003 | Stafford et al. | |
| 6,596,398 B1 | 7/2003 | Russo et al. | |
| 6,692,931 B1 | 2/2004 | Reutter et al. | |
| 6,743,908 B2 | 6/2004 | Filpula et al. | |
| 6,806,063 B2 | 10/2004 | Pedersen et al. | |
| 6,869,930 B1 | 3/2005 | Havelund et al. | |
| 6,872,393 B2 | 3/2005 | Whitlow et al. | |
| 6,913,915 B2 | 7/2005 | Ensor et al. | |
| 7,060,259 B2 | 6/2006 | Bentley et al. | |
| 7,118,737 B2 | 10/2006 | Kochendoerfer et al. | |
| 7,199,223 B2 | 4/2007 | Bossard et al. | |
| 7,230,081 B1 | 6/2007 | Jensen et al. | |
| 7,259,224 B2 | 8/2007 | Harris et al. | |
| 7,338,788 B2 | 3/2008 | Pedersen et al. | |
| 2002/0110535 A1 | 8/2002 | Jones | |
| 2003/0069170 A1* | 4/2003 | Soltero et al. | 514/2 |
| 2003/0143596 A1 | 7/2003 | Bentley et al. | |
| 2004/0063911 A1 | 4/2004 | DeFrees et al. | |
| 2004/0137557 A1 | 7/2004 | DeFrees et al. | |
| 2004/0235734 A1 | 11/2004 | Bossard et al. | |
| 2005/0106658 A1 | 5/2005 | DeFrees et al. | |
| 2005/0234230 A1 | 10/2005 | Zander et al. | |
| 2006/0019877 A1 | 1/2006 | Conradt et al. | |
| 2006/0088906 A1 | 4/2006 | DeFrees et al. | |
| 2006/0111279 A1 | 5/2006 | DeFrees et al. | |
| 2006/0286634 A1 | 12/2006 | Kingsman et al. | |
| 2007/0026485 A1 | 2/2007 | DeFrees et al. | |
| 2007/0087961 A1 | 4/2007 | Eichner et al. | |

(Continued)

FOREIGN PATENT DOCUMENTS

EP    0306968 A2    3/1989
EP    0605963       7/1994

(Continued)

OTHER PUBLICATIONS

Ekrami et al. (1995) FEBS Lett. 371: 283-286.*
Abuchowski et al., Cancer therapy with chemically modified enzymes. I. Antitumor properties of polyethylene glycol-asparaginase conjugates. *Cancer Biochem. Biophys.* 7: 175-86 (1984).
Acharya et al., Rare Bleeding Disorder Registry: deficiencies of factors IIi, V, VII, X, XIII, fibrinogen and dysfibrinogenemias, *J. Throm. Haemostasis*, 2(2):248-56 (2004).
Baxter announces collaborations to develop longer acting forms of blood clotting factors. *Baxter News (online)*, Sep. 29, 2005.
Bi et al., Target disruption of the mouse factor VIII gene produces a model of Haemophilia A. *Nat. Genet.* 10: 119-21 (1995).
Boturyn et al., Synthesis of fluorescent probes for the detection of abasic sites in DNA, *Tetrahedron*, 53(15):5485-92 (1997).

(Continued)

*Primary Examiner* — Lisa J Hobbs
(74) *Attorney, Agent, or Firm* — Marshall, Gerstein & Borun LLP

(57) ABSTRACT

The invention relates to materials and methods of conjugating a water soluble fatty acid derivative to a therapeutic protein comprising contacting the therapeutic protein with an activated water soluble fatty acid derivative under conditions that allow conjugation.

37 Claims, 1 Drawing Sheet

(56) References Cited

U.S. PATENT DOCUMENTS

| | | |
|---|---|---|
| 2007/0191597 A1 | 8/2007 | Jain et al. |
| 2007/0244301 A1 | 10/2007 | Siekmann et al. |
| 2007/0254836 A1 | 11/2007 | Defrees et al. |
| 2007/0282096 A1 | 12/2007 | Jain et al. |
| 2008/0146771 A1 | 6/2008 | Kozlowski et al. |
| 2008/0206182 A1 | 8/2008 | Sommermeyer et al. |
| 2008/0221032 A1 | 9/2008 | Turecek et al. |
| 2008/0260755 A1 | 10/2008 | Metzner et al. |
| 2009/0028822 A1 | 1/2009 | DeFrees et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2011/0054152 A1 | 3/2011 | Zander et al. |

FOREIGN PATENT DOCUMENTS

| | | |
|---|---|---|
| EP | 1258497 A2 | 11/2002 |
| EP | 1260582 A1 | 11/2002 |
| EP | 1400533 A1 | 3/2004 |
| EP | 1 681 303 A1 | 7/2006 |
| EP | 2070951 A1 | 6/2009 |
| WO | WO-91/009122 A1 | 6/1991 |
| WO | WO-92/16555 A1 | 10/1992 |
| WO | WO-94/05332 A2 | 3/1994 |
| WO | WO-94/15625 A1 | 7/1994 |
| WO | WO-94/29370 A1 | 12/1994 |
| WO | WO-95/01804 A1 | 1/1995 |
| WO | WO-96/40662 A2 | 12/1996 |
| WO | WO-96/40731 A1 | 12/1996 |
| WO | WO-96/41813 A2 | 12/1996 |
| WO | WO-97/11957 A1 | 4/1997 |
| WO | WO-99/28455 A1 | 6/1999 |
| WO | WO-99/32134 A1 | 7/1999 |
| WO | WO-00/12587 A2 | 3/2000 |
| WO | WO-00/23114 A2 | 4/2000 |
| WO | WO-00/48635 A1 | 8/2000 |
| WO | WO-01/82943 A2 | 11/2001 |
| WO | WO-01/83725 A1 | 11/2001 |
| WO | WO-02/002764 A2 | 1/2002 |
| WO | WO-02/22776 A2 | 3/2002 |
| WO | WO-02/29025 A2 | 4/2002 |
| WO | WO-02/77218 A1 | 10/2002 |
| WO | WO-03/31464 A2 | 4/2003 |
| WO | WO-03/45980 A2 | 6/2003 |
| WO | WO-03/46102 A2 | 6/2003 |
| WO | WO-2004/000366 A1 | 12/2003 |
| WO | WO-2004/014424 A1 | 2/2004 |
| WO | WO-2004/024776 A1 | 3/2004 |
| WO | WO-2004/030617 A2 | 4/2004 |
| WO | WO-2004/060965 A2 | 7/2004 |
| WO | WO-2004/075923 A2 | 9/2004 |
| WO | WO-2004/089280 | 10/2004 |
| WO | WO-2004/108070 A2 | 12/2004 |
| WO | WO-2005/014024 A2 | 2/2005 |
| WO | WO-2005/014035 A2 | 2/2005 |
| WO | WO-2005/014655 A2 | 2/2005 |
| WO | WO-2005/016974 A1 | 2/2005 |
| WO | WO-2005/055950 A2 | 6/2005 |
| WO | WO-2005/070138 A2 | 8/2005 |
| WO | WO-2005/092369 A2 | 10/2005 |
| WO | WO-2005/117984 A2 | 12/2005 |
| WO | WO 2005117984 A2 * | 12/2005 |
| WO | WO-2006/013202 A2 | 2/2006 |
| WO | WO-2006/016168 A2 | 2/2006 |
| WO | WO-2006/020372 A2 | 2/2006 |
| WO | WO-2006/053299 A2 | 5/2006 |
| WO | WO-2006/069246 A2 | 6/2006 |
| WO | WO-2006/071801 | 7/2006 |
| WO | WO-2006/074279 A1 | 7/2006 |
| WO | WO-2006/127896 A2 | 11/2006 |
| WO | WO-2006/134173 A2 | 12/2006 |
| WO | WO-2006/138572 A2 | 12/2006 |
| WO | WO-2007/022784 A2 | 3/2007 |
| WO | WO-2007076062 A2 | 7/2007 |
| WO | WO-2007/140282 A1 | 12/2007 |
| WO | WO-2008/025856 A2 | 3/2008 |
| WO | WO-2008/035373 A2 | 3/2008 |
| WO | WO-2008/057683 A2 | 5/2008 |
| WO | WO-2008/074032 A1 | 6/2008 |
| WO | WO-2008/081024 A1 | 7/2008 |
| WO | WO-2008/083346 A1 | 7/2008 |
| WO | WO-2008/119815 A1 | 10/2008 |
| WO | WO-2009/000522 A1 | 12/2008 |
| WO | WO-2009/006620 A1 | 1/2009 |
| WO | WO-2009/047500 A1 | 4/2009 |
| WO | WO-2009/089396 A2 | 7/2009 |
| WO | WO-2009/108806 A1 | 9/2009 |
| WO | WO-2009/130602 A2 | 10/2009 |
| WO | WO-2009/141418 A1 | 11/2009 |
| WO | WO-2009/141433 A1 | 11/2009 |
| WO | WO-2009/149303 A1 | 12/2009 |
| WO | WO-2010/010324 A1 | 1/2010 |
| WO | WO-2010/062768 A1 | 6/2010 |
| WO | WO-2010/083536 A1 | 7/2010 |
| WO | WO-2010/100430 A1 | 9/2010 |
| WO | WO-2010/102886 A1 | 9/2010 |
| WO | WO-2010/120365 A2 | 10/2010 |
| WO | WO-2010/140148 A1 | 12/2010 |
| WO | WO-2011/014890 A1 | 2/2011 |
| WO | WO-2011/018496 A2 | 2/2011 |
| WO | WO-2011/037896 A2 | 3/2011 |
| WO | WO-2011/064247 A1 | 6/2011 |
| WO | WO-2011/101242 A1 | 8/2011 |
| WO | WO-2011/101267 A1 | 8/2011 |
| WO | WO-2011/101277 A1 | 8/2011 |
| WO | WO-2011/135307 A1 | 11/2011 |
| WO | WO-2011/135308 A1 | 11/2011 |
| WO | WO-2012/016131 A1 | 2/2012 |
| WO | WO-2012/068134 A1 | 5/2012 |
| WO | WO-2013/009627 A2 | 1/2013 |

OTHER PUBLICATIONS

Burgess et al. (eds.), Guide to Protein Purification, Methods in Enzymology, 2nd edition, vol. 463, Academic Press (2009).

Caliceti et al., Pharmacokinetics of pegylated interferons: What is misleading? *Digest. Liver Dis.* 36(Suppl. 3): S334-9 (2004).

Cline et al., The aminolysis of N-hydroxysuccinimide esters. A structure-reactivity study, J. Am. Chem. Soc., 109:3087-91 (1987).

Cordes et al., Nucleophilic catalysis of semicarbazone formation by anilines. *J. Am. Chem. Soc.*, 84: 826-31 (1962).

DeFrees et al., GlycoPEGylation of recombinant therapeutic proteins produced in *Escherichia coli*, Glycobiology, 16(9):833-43 (2006).

Dirksen et al., Nucleophilic catalysis of hydrazone formation and transimination: Implications for dynamic covalent chemistry. *J. Am. Chem. Soc.*, 128: 15602-3 (2006).

Dirksen et al., Nucleophilic catalysis of oxime ligation. *Ange. Chem. Int. Ed.*, 45(45): 7581-4 (2006).

Dirksen et al., Rapid oxime and hydrazone ligations with aromatic aldehyres for biomolecular labeling. *Bioconj. Chem.*, 19(12): 2543-8 (2008).

Eigenbrot, Structure, function, and activation of coagulation factor VII, Curr. Protein Pept. Sci., 3(3):287-99 (2002).

Ekrami et al., Water-soluble fatty acid derivatives as acrylating agents for reversible lipidization of polypeptides, FEBS Lett., 371:283-6 (1995).

Fernandes et al., The effect of polysialylation on the immunogenicity and antigenicity of asparaginase: implication in its pharmacokinetics, Int. J. Pharm., 217(1-2):215-24 (2001).

Gitschier et al., Characterization of the human factor VIII gene, Nature, 312(5992):326-30 (1984).

Great Britain Search Report and Written Opinion, GB-1012482.4, dated Nov. 24, 2010.

Gregoriadis et al., Improving the therapeutic efficiency of peptides and proteins: A role for polysialic acids. *Int. J. Pharma.* 300(1-2): 125-30 (2005).

Hagen et al., Characterization of a cDNA coding for human factor VII, Proc. Natl. Acad. Sci. USA, 83(8):2412-6 (1986).

Hang et al., Chemical probes for the rapid detection of Fatty-acylated proteins in Mammalian cells, *J. Am. Chem. Soc.*, 129(10):2744-5 (2007).

(56) References Cited

OTHER PUBLICATIONS

Harris et al., Effect of pegylation on pharmaceuticals. *Nat. Rev. Drug Discovery.* 2: 214-21 (2003).
Heredia et al., Aminooxy end-functionalized polymers synthesized by ATRP for chemoselective conjugation to proteins, Macromolecules, 40(14):4772-9 (2007).
International Preliminary Report on Patentability, PCT/GB2010/001422, dated Jan. 31, 2012.
International Preliminary Report on Patentability, PCT/US2009/052103, dated Feb. 1, 2011.
International Preliminary Report on Patentability, PCT/US2010/043242, dated Jan. 31, 2012.
International Search Report and Written Opinion for International Application No. PCT/US2011/065591, mailing date Mar. 23, 2012.
International Search Report and Written Opinion of the International Searching Authority, PCT/GB2010/001422, European Patent Office, dated Feb. 4, 2011.
International Search Report and Written Opinion of the International Searching Authority, PCT/US2007/007560, European Patent Office, dated Sep. 18, 2007.
International Search Report and Written Opinion of the International Searching Authority, PCT/US2009/052103, European Patent Office, dated Feb. 12, 2010.
International Search Report and Written Opinion, PCT/US2010/043242, dated Feb. 10, 2011.
Jain et al., Polysialylation: The natural way to improve the stability and pharmacokinestics of protein and peptide drugs http://www.lipoxen.co.uk/media/48760/dds%20and%20s%20pp39.pdf, DD&S 4(1) 309 (2004).
Ong et al., Synthesis of ceramides using N-hydroxysuccinimide estersJ. Lipid Res., 13:819-22 (1972).
Kohler, Aniline: A catalyst for sialic acid detection. *ChemBioChem*, 10: 2147-50 (2009).
Kozlowski et al., Development of pegylated interferons for the treatment of chronic Hepatitis C. *BioDrugs*, 15(7): 419-29 (2001).
Kubler-Kielb et al., A new method for conjugation of carbohydrates to proteins using an aminooxy-thiol heterobifunctional linker, J. Org. Chem., 70:6987-90 (2005).
Lees et al., Versatile and efficient synthesis of protein-polysaccharide conjugate vaccines using aminooxy reagents and oxime chemistry. *Vaccine*, 24(6): 716-29 (2006).
Lehninger, Biochemistry, 2nd ed., New York: Worth Publishers, Inc., pp. 71-77 (1975).
Leyte et al., The pro-polypeptide of von Willebrand factor is required for the formation of a functional factor VIII-binding site on mature von Willebrand factor, Biochem. J., 274(Pt.1):257-61 (1991).
Malaprade, Analytical application, Bull. Soc. Chim. France, 43:683-96 (1928).
Mann, Biochemistry and physiology of blood coagulation, Thromb. Haemost., 82(2):165-74 (1999).
Marko et al., Efficient, aerobic, ruthenium-catalyzed oxidation of alcohols into aldehydes and ketones, J. Am. Chem. Soc., 119:12661-2 (1997).
Meynial-Salles et al., In vitro glycosylation of proteins: an enzymatic approach, J. Biotechnol., 46(1):1-14 (1996).
Mukherji et al., The chemical biology of branched-chain lipid metabolism, Prog. Lipid Res., 42(5):359-76 (2003).
Nektar Advanced PEGylation Catalog 2005-2006, p. 30 (2005).
Nektar Advanced PEGylation Price List 2005-2006, p. 11 (2005).
NOF Corporation DDS Catalogue, p. 58 (2005).
Peri et al., Chemo- and stereoselective glycosylation of hydroxylamino derivatives: A versatile approach to glycoconjugates, Tetrahedron, 54(40):12269-78 (1998).
Pinotti et al., Modulation of factor VII levels by intron 7 polymorphisms: population and in vitro studies, Blood, 95(11):3423-8 (2000).
Roberts et a., Chemistry for peptide and protein pegylation *Adv. Drug Del. Rev.* 54: 459-76 (2002).
Rosen et al., Assay of factor VIII: C with a chromogenic substrate. *Scand J. Haematol.* 33(Suppl. 40): 139-45 (1984).
Rostin et al., B-domain deleted recombinant coagulation factor Viii modified with monomethoxy polyethylene glycol. *Bioconjugate Chem.* 11: 387-96 (2000).

Rothfus et al., Glycopeptides. IV. The periodate oxidation of glycopeptides from human gamma-globulin, J. Biol. Chem., 238:1402-10 (1963).
Ruggeri et al., von Willebrand factor, FASEB J., 7(2):308-16 (1993).
Sabater-Lleal et al., Human F7 sequence is split into three deep clades that are related to FVII plasma levels, Hum. Genet., 118(6):741-51 (2006).
Saenko et al., Strategies towards a longer acting factor VIII. *Haemophilia.* 12: 42-51 (2006).
Sakuragawa et al., Studies on the stability of factor VIII modified by polyethylene glycol. *Acta Med. Biol.* 36:1-5 (1988).
Sambrook et al., Molecular Cloning: A Laboratory Manual, 2nd ed., Cold Spring Harbor Press, sections 9,47-9.51 (1989).
Sasson et al., Engineering prolonged-acting prodrugs employing an albumin-binding probe that undergoes slow hydrolysis at physiological conditions, J. Control. Release, 142(2):214-20 (2010).
Schechter et al., Albumin-insulin conjugate releasing insulin slowly under physiological conditions: a new concept for long-acting insulin, Bioconjug. Chem., 16(4):913-20 (2005).
Schechter et al., New technologies to prolong life-time of peptide adn protein drugs in vivo, Int. J. Peptide Res. and Therapeutics, 13(1-2):105-17 (2007).
Schenone et al., The blood coagulation cascade, Curr. Opin. Hematol., 11(4):272-7 (2004).
Seffernick et al., Melamine deaminase and atrazine chlorohydrolase: 98% identical but functionally different. *J. Bacteriology.* 2405-10 (2001).
Severs et al., Characterization of PEGylated factor VIII molecules. *Blood.* 108: 11-12 (2006). Abstract.
Sola et al., Glycosylation of therapeutic proteins: an effective strategy to optimize efficacy, BioDrugs, 21(1):9-21 (2010).
Spector, Fatty acid binding to plasma albumin, J. Lipid Res., 16(3):165-79 (1975).
Study shows molecular size and structure of PEG interferon molecules, as used in pegintron(R), affect antiviral activity in vitro. *Hispanic PR Wire*, Oct. 28,2003.
Thompson, Structure and function of the Factor VIII gene and protein, Semin. Thromb. Hemost., 29:11-29 (2002).
Thygesen et al., Nucleophilic catalysis of carbohydrate oxime formation by anilines. *J. Org. Chem.*, 75: 1752-5 (2010).
Toyokuni et al., Synthesis of a new heterobifunctional linker, N-[4-(aminooxy)butyl]maleimide, for facile access to a thiol-reactive 18F-labeling agent, Bioconjug. Chem., 14(6):1253-9 (2003).
Tsubery et al., Prolonging the action of protein and peptide drugs by a novel approach of reversible polyethylene glycol modification. *J. Biol. Chem.* 279(37): 38118-24 (2004).
Tsutsumi et al., Site-specific chemical modification with polyethylene glycol of recombinant immunotoxin anti-Tac(Fv)-PE38 (LMB-2) improves antitumor activity and reduces animal toxicity and immunogenicity. *Proc. Natl. Acad. Sci. USA.* 97: 8548-53 (2000).
Urrutigoity et al., Biocatalysis in organic solvents with a polymer-bound horseradish peroxidase. *Biocatalysis.* 2: 145-9 (1989).
Van Lenten et al., Studies on the chemical and enzymatic modification of glycoproteins. A general method for the tritiation of sialic acid-containing glycoproteins, J. Biol. Chem., 246(6):1889-94 (1971).
Vehar et al., Structure of human factor VIII, Nature, 312(5992):337-42 (1984).
Veronese et al., Bioconjugation in pharmaceutical chemistry. *IL Farmaco.* 54: 497-516 (1999).
Wells et al., Additivity of mutational effects in proteins. *Biochemistry.* 29(37): 8509-17 (1990).
Wilchek et al., Labeling glycoconjugates with hydrazide reagents. *Methods Enzymol.* 138: 42942 (1987).
Zalipsky et al., Hydrazide derivatives of poly(ethylene glycol) and their bioconjugates. Poly(ethylene glycol) Chemistry and Biological Applications. Chapter 21, pp. 318-341 (1997).
Zeng et al., High-efficiency labeling of sialylated glycoproteins on living cells. *Nat. Meth.* 6(3): 207-9 (2009).
Caplar et al., Positionally isometric organic gelators: structure-gelation study, racemic versus enantiomeric gelators and solvation effects, Chem. Eur. J., 16:3066-82 (2010).

* cited by examiner

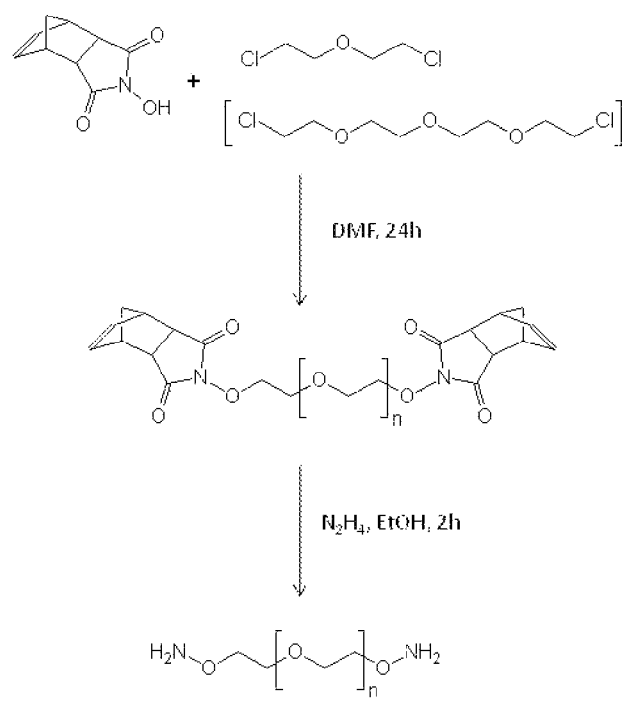

MATERIALS AND METHODS FOR CONJUGATING A WATER SOLUBLE FATTY ACID DERIVATIVE TO A PROTEIN

FIELD OF THE INVENTION

The present invention relates to materials and methods for conjugating a water soluble fatty acid derivative to a protein.

BACKGROUND OF THE INVENTION

A variety of molecules and/or compounds have been described for conjugating to therapeutic proteins in order to increase the half-life of the conjugated therapeutic proteins following administration to a patient (Veronese F M and Mero A, BioDrugs 2008; 22:315-29; Gregoriadis G et al., Int J Pharm 2005; 300:125-30; and Shechter Y et al.; International Journal of Peptide Research and Therapeutics 2007; Vol 13 :105-17).

Fatty acids (FA) can be conjugated to therapeutic proteins to form longer-acting derivatives. This principle for prolongation of protein or peptide half-life is based on the fact that FA can bind to human serum albumin (HSA; also referred to as albumin binding probes). The association of a FA with human serum albumin in the blood stream can lead to a substantial prolongation of the half-life of the therapeutic protein as it will recycle together with albumin through the neonatal Fc receptor. FA and derivatives thereof (e.g., corresponding methyl esters) have shown similar albumin-binding properties (Spector A A, J Lipid Res 1975; 16:165-79).

One prominent example for this longer-acting principle is insulin detemir (Levemir®) from Novo Nordisk. In insulin detemir, the carboxyl group of a FA is covalently coupled to the $\epsilon$-amino group of a lysine residue of the insulin protein (see, e.g., U.S. Pat. Nos. 5,866,538; 6,011,007; and 6,869, 930). Other research groups have described similar approaches (Shechter Y et al., Bioconj Chem 2005; 16:913-20; and Sasson K et al., J Control Release 2010; 142:214-20). For example, these groups describe a releasable FMOC system containing an active NHS ester for coupling to amino groups of proteins. The difference however is that in this concept the FA is linked to the protein via a functional group in ω-position thereby rendering the carboxyl group intact. Thus, prolonged-acting prodrugs can be prepared that bind to human serum albumin yet dissociate over time as the FMOC system undergoes slow hydrolysis under physiological conditions (Sasson K et al., J Control Release 2010; 142:214-20).

In addition to fatty acids, the preparation of conjugates by forming a covalent linkage between the water soluble polymer and the therapeutic protein can be carried out by a variety of chemical methods. PEGylation of polypeptide drugs protects them in circulation and improves their pharmacodynamic and pharmacokinetic profiles (Harris and Chess, Nat Rev Drug Discov. 2003; 2:214-21). The PEGylation process attaches repeating units of ethylene glycol (polyethylene glycol (PEG)) to a polypeptide drug. PEG molecules have a large hydrodynamic volume (5-10 times the size of globular proteins), are highly water soluble and hydrated, non-toxic, non-immunogenic and rapidly cleared from the body. PEGylation of molecules can lead to increased resistance of drugs to enzymatic degradation, increased half-life in vivo, reduced dosing frequency, decreased immunogenicity, increased physical and thermal stability, increased solubility, increased liquid stability and reduced aggregation. The first PEGylated drugs were approved by the FDA in the early 1990s. Since then, the FDA has approved several PEGylated drugs for oral, injectable and topical administration.

Polysialic acid (PSA), also referred to as colominic acid (CA), is a naturally occurring polysaccharide. It is a homopolymer of N-acetylneuraminic acid with $\alpha(2\rightarrow 8)$ ketosidic linkage and contains vicinal diol groups at its non-reducing end. It is negatively charged and a natural constituent of the human body. It can easily be produced from bacteria in large quantities and with pre-determined physical characteristics (U.S. Pat. No. 5,846,951). Because the bacterially-produced PSA is chemically and immunologically identical to PSA produced in the human body, bacterial PSA is non-immunogenic, even when coupled to proteins. Unlike some polymers, PSA acid is biodegradable. Covalent coupling of colominic acid to catalase and asparaginase has been shown to increase enzyme stability in the presence of proteolytic enzymes or blood plasma. Comparative studies in vivo with polysialylated and unmodified asparaginase revealed that polysialylation increased the half-life of the enzyme (Fernandes and Gregoriadis, Int J Pharm. 2001; 217:215-24).

Coupling of PEG-derivatives to peptides or proteins is reviewed by Roberts et al. (Adv Drug Deliv Rev 2002; 54:459-76). One approach for coupling water soluble polymers to therapeutic proteins is the conjugation of the polymers via the carbohydrate moieties of the protein. Vicinal hydroxyl (OH) groups of carbohydrates in proteins can be easily oxidized with sodium periodate (NaIO4) to form active aldehyde groups (Rothfus and Smith, J Biol Chem 1963; 238:1402-10; van Lenten and Ashwell, J Biol Chem 1971; 246:1889-94). Subsequently the polymer can be coupled to the aldehyde groups of the carbohydrate by use of reagents containing, for example, an active hydrazide group (Wilchek M and Bayer E A, Methods Enzymol 1987; 138:429-42). A more recent technology is the use of reagents containing aminooxy groups which react with aldehydes to form oxime linkages (WO 96/40662, WO2008/025856).

Additional examples describing conjugation of a water soluble polymer to a therapeutic protein are described in WO 06/071801 which teaches the oxidation of carbohydrate moieties in von Willebrand factor and subsequent coupling to PEG using hydrazide chemistry; US Publication No. 2009/0076237 which teaches the oxidation of rFVIII and subsequent coupling to PEG and other water soluble polymers (e.g. PSA, HES, dextran) using hydrazide chemistry; WO 2008/025856 which teaches oxidation of different coagulation factors, e.g. rFIX, FVIII and FVIIa and subsequent coupling to e.g., PEG, using aminooxy chemistry by forming an oxime linkage; and U.S. Pat. No. 5,621,039 which teaches the oxidation of FIX and subsequent coupling to PEG using hydrazide chemistry.

Notwithstanding the above materials and methods for protein conjugation, new materials and methods are desired that, for example, allow manipulation and preparation of stable protein conjugates. Although fatty acids can provide the benefit of binding HSA, fatty acids are often difficult to manipulate in an aqueous environment and can be released or removed from its protein binding partner over time.

SUMMARY OF THE INVENTION

The present invention provides materials and methods for conjugating polymers and water soluble fatty acid derivatives to proteins that improves the protein's pharmacodynamic and/or pharmacokinetic properties while minimizing the costs associated with the various reagents and the health risks to the patient recipients when the conjugation reaction is catalyzed by a nucleophilic catalyst. The present invention provides materials and methods for conjugating water soluble fatty acid derivatives to proteins in an aqueous solution, thereby producing stable protein conjugates wherein the fatty acid derivatives are not released over time.

In one embodiment of the present invention, a water soluble fatty acid derivative is provided comprising a fatty acid or fatty acid ester attached to a water soluble linker, said fatty acid derivative stably attached to a therapeutic protein. In another embodiment, the fatty acid derivative binds human serum albumin (HSA) in vitro or in vivo. In still another embodiment, the fatty acid derivative—therapeutic protein conjugate has increased half-life relative to a native therapeutic protein. In yet another embodiment, an aforementioned fatty acid derivative comprises a saturated fatty acid or unsaturated fatty acid. In a related embodiment, the fatty acid is a saturated fatty acid. In yet another embodiment, the fatty acid is a branched chain fatty acid.

Various lengths of fatty acids in the fatty acid derivatives are contemplated. In one embodiment, an aforementioned fatty acid derivative is provided wherein the fatty acid comprises a chain length between C10 and C24, including synthetic fatty acids with odd carbon numbers. In one embodiment, an aforementioned fatty acid derivative is provided wherein the fatty acid comprises a chain length selected from the group consisting of: C10, C12, C14, C16, C18, C20, C20, C22 and C24. In another embodiment, the fatty acid has a chain length selected from the group consisting of C14, C16 and C18. In still another the fatty acid has a chain length selected from the group consisting of C13, C15 and C17.

In still another embodiment, an aforementioned fatty acid derivative is provided wherein the fatty acid is attached to the water soluble linker at a group on the fatty acid selected from the group consisting of: terminal carboxyl group and ω group. In another embodiment, the fatty acid is attached to the water soluble linker at the ω group. In still another embodiment, the ω group is selected from the group consisting of: hydroxyl, amino, thio, and carboxyl.

In one embodiment of the present invention, an aforementioned fatty acid derivative is provided wherein the fatty acid is 16-hydroxyhexadecanoic acid.

In another embodiment, a fatty acid derivative is provided wherein the fatty acid ester is selected from the group consisting of: methyl ester and ethyl ester. In one embodiment, the fatty acid ester is 16-hydroxyhexadecanoic acid methyl ester.

Various water soluble linkers are contemplated in the present invention. In one embodiment, an aforementioned fatty acid derivative is provided wherein the water soluble linker comprises a water soluble polymer and at least one functional group attached to the therapeutic protein. In one embodiment, the functional group attached to the therapeutic protein has the ability to impart a negative or positive charge, thereby making the linker water soluble. In still another embodiment, the functional group is selected from the group consisting of a sulfo group, carboxyl group, hydroxyl group, amino group, amido group, maleimido group, aminooxy group and hydrazide group. In one embodiment, the functional group is an aminooxy group.

Numerous water soluble polymers are contemplated in the present invention. In one embodiment, an aforementioned fatty acid derivative is provided wherein the water soluble polymer, which is integral part of the linker, is selected from the group consisting of: polyethylene glycol (PEG), branched PEG, polysialic acid (PSA), hydroxyalkyl starch (HAS), hydroxyethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC). In still another embodiment, the water soluble polymer is PEG. Various lengths of water soluble polymers are also contemplated herein. In one embodiment, a fatty acid derivative is provided wherein the water soluble polymer comprises a chain length selected from the group consisting of O3, O5, O7, O9, O11, O13 and O15.

In one embodiment, a fatty acid derivative is provided wherein the water soluble linker is selected from the group consisting of:

3-oxapentane-1,5-dioxyamine

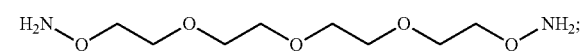 [SMILES: NOCCOCCOCCOCCON]

3,6,9-triaoxaundecane-1,11-dioxyamine

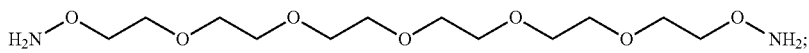

3,6,9,12,15-penatoxaheptadecane-1,17-dioxyamine;

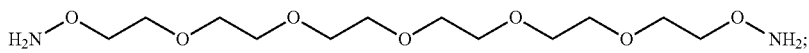

and
3,6,9,12,15,18,21-heptaoxatricosane-1,23-dioxyamine

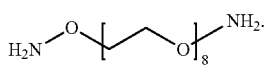

In another embodiment of the invention, a fatty acid derivative is provided wherein the fatty acid derivative is stably attached to the therapeutic protein by an oxime linkage. In another embodiment, the oxime linkage is formed between an oxime group on the water soluble linker and an aldehyde group of an oxidized carbohydrate on the therapeutic protein.

In yet another embodiment of the invention, a fatty acid derivative is provided wherein the fatty acid derivative is stably attached to the therapeutic protein by a maleimide group on the water soluble linker to a free sulfhydryl group on the therapeutic protein. In still another embodiment, the fatty acid derivative is stably attached to the therapeutic protein by an N-hydroxysuccinimide ester on the water soluble linker to a free amino group on the therapeutic protein.

In one embodiment of the invention, a fatty acid derivative is provided wherein the fatty acid derivative is selected from the group consisting of:

a) 16-(2-(2-(2-(2-Aminooxyethoxy)-ethoxy)-ethoxy)-ethoxyimino)-hexadecanoic acid sodium salt of the formula:

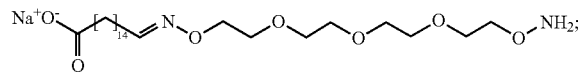

and
b) 16-(2-(2-(2-(2-Aminooxyethoxy)-ethoxy)-ethoxy)-ethoxyamino)-hexadecanoic acid methyl ester,

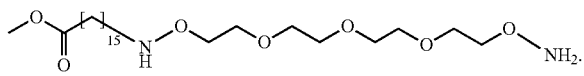

Various therapeutic proteins are contemplated in the present invention. In one embodiment, an aforementioned fatty acid derivative is provided wherein the therapeutic protein is selected from the group consisting of: Factor IX (FIX), Factor V111 (FVIII), Factor VIIa (FVIIa), von Willebrand Factor (VWF), Factor FV (FV), Factor X (FX), Factor XI (FXI), Factor XII (FXII), thrombin (FH), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), a protein in Table 1, or a biologically active fragment, derivative or variant thereof. In another embodiment, the therapeutic protein is FVIIa. In yet another embodiment, the therapeutic protein is FVIII. In still another embodiment, the therapeutic protein is FIX.

Methods of preparing fatty acid derivatives are also contemplated herein. In one embodiment, a method of preparing a fatty acid derivative described herein is provided comprising: a) oxidizing a ω-hydroxy group on a fatty acid to generate an aldehyde group on the fatty acid; and b) coupling a water soluble linker comprising an active aminooxy group to the aldehyde group to form a stable oxime linkage, wherein the fatty acid derivative is water soluble. In one embodiment, the aforementioned method is provided wherein the ω-hydroxy group is oxidized by an oxidation reagent selected from the group consisting of: Dess Martin periodinane reagent, Tempo reagent, Swern oxidation with oxalyl chloride/DMSO, tetrapropylammoniumperruthenate (TPAP), chrome VI reagents such as Collins reagent, pyridinium chloro chromate (PCC), and pyridinium dichromate. In still another embodiment, the oxidation reagent is Dess Martin periodinane.

In another embodiment, an aforementioned method is provided wherein the fatty acid is a saturated fatty acid or unsaturated fatty acid. In still another embodiment, the fatty acid is a saturated fatty acid.

In yet another embodiment of the invention, an aforementioned method is provided wherein the fatty acid is a branched chain fatty acid.

According to another embodiment, an aforementioned method is also provided wherein the fatty acid comprises a chain length between C10 and C24, including synthetic fatty acids with odd carbon numbers. In one embodiment, an aforementioned fatty acid derivative is provided wherein the fatty acid comprises a chain length selected from the group consisting of: C10, C12, C14, C16, C18, C20, C20, C22 and C24. In another embodiment, the fatty acid has a chain length selected from the group consisting of C14, C16 and C18. In still another the fatty acid has a chain length selected from the group consisting of C13, C15 and C17.

In yet another embodiment, an aforementioned method is provided wherein the water soluble linker is 3,6,9-triaoxaundecane-1,11-dioxyamine of the formula:

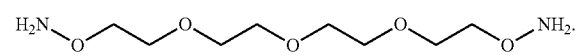

In still another embodiment, an aforementioned method is provided wherein the water soluble linker is 3,6,9,12,15-penatoxaheptadecane-1,17-dioxyamine of the formula:

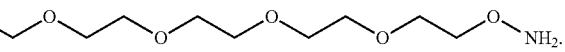

In still another embodiment, an aforementioned method is provided wherein the water soluble linker comprises a water soluble polymer and at least one aminooxy group.

Numerous water soluble polymers are contemplated in the present invention for use in an aforementioned method. In one embodiment, an aforementioned method is provided wherein the water soluble polymer is selected from the group consisting of: polyethylene glycol (PEG), branched PEG, polysialic acid (PSA), hydroxyalkyl starch (HAS), hydroxyethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glcol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC). In one embodiment, the water soluble polymer is PEG.

Various lengths of water soluble polymers are also contemplated. In one embodiment, an aforementioned method is provided wherein the water soluble polymer comprises a chain length selected from the group consisting of O5, O7, O9, O11, O13 and O15.

In still another embodiment, an aforementioned method is provided wherein the water soluble linker is selected from the group consisting of:

a) 3-oxapentane-1,5-dioxyamine of the formula:

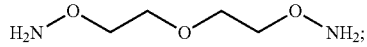

b) 3,6,9-triaoxaundecane-1,1'-dioxyamine of the formula:

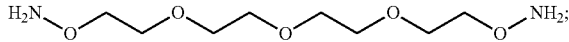 [SMILES: NOCCOCCOCCOCCON]

c) 3,6,9,12,15-penatoxaheptadecane-1,17-dioxyamine of the formula:

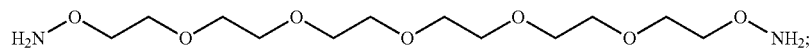

and
d) 3,6,9,12,15,18,21-heptaoxatricosane-1,23-dioxyamine of the formula:

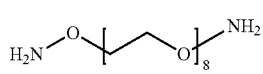

Still other methods for making the fatty acid derivatives are contemplated herein. In one embodiment, a method of preparing an aforementioned fatty acid derivative is provided comprising: a) esterifying a carboxyl group on a fatty acid to generate an ester on the fatty acid; b) activating a ω-hydroxy group on a fatty acid by introduction of a mesyl group on the fatty acid of step a); and c) coupling a water soluble linker comprising an active aminooxy group by substituting the mesyl group of step b) thereby forming a stable oxyamine-methylene bond; wherein the fatty acid derivative is water soluble.

In one embodiment, the aforementioned is provided wherein the carboxyl group is esterified by an esterifying agent selected from the group consisting of: acetyl chloride, methanol in the presence of acid, ethanol in the presence of acid, diazomethane, and methyliodide. In another embodiment, the esterifying agent is acetyl chloride.

In still another embodiment, the aforementioned is provided wherein the co-hydroxy group is activated by an activating agent selected from the group consisting of: mesyl chloride, tosyl chloride and nosyl chloride. In one embodiment, the activating agent is mesyl chloride.

Various fatty acids are contemplated for use in the aforementioned method. In one embodiment, the aforementioned is provided wherein the fatty acid is a saturated fatty acid or unsaturated fatty acid. In another embodiment, the fatty acid is a saturated fatty acid. In yet another embodiment, the fatty acid is a branched chain fatty acid.

In still another embodiment, the aforementioned method is provided wherein the fatty acid comprises a chain length between C10 and C24, including synthetic fatty acids with odd carbon numbers. In one embodiment, an aforementioned fatty acid derivative is provided wherein the fatty acid comprises a chain length selected from the group consisting of: C10, C12, C14, C16, C18, C20, C20, C22 and C24. In another embodiment, the fatty acid has a chain length selected from the group consisting of C14, C16 and C18. In still another the fatty acid has a chain length selected from the group consisting of C13, C15 and C17.

Various water soluble polymers are also contemplated for the use in the aforementioned method. In one embodiment, the aforementioned method is provided wherein the water soluble linker comprises a water soluble polymer and at least one aminooxy group. In another embodiment, the water soluble polymer is selected from the group consisting of: polyethylene glycol (PEG), branched PEG, polysialic acid (PSA), hydroxyalkyl starch (HAS), hydroxyethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC). In another embodiment, the water soluble polymer is PEG.

In still another embodiment of the invention, an aforementioned method is provided wherein the water soluble polymer comprises a chain length selected from the group consisting of O3, O5, O7, O9, O11, O13 and O15. In another embodiment, the water soluble linker is selected from the group consisting of:[0050]

Methods of preparing conjugated proteins are also contemplated in the present invention. In one embodiment, a method of preparing a conjugated therapeutic protein is provided comprising contacting an oxidized carbohydrate moiety on the therapeutic protein with an aforementioned fatty acid derivative (or a water soluble polymer as described herein) under conditions that allow conjugation; the carbohydrate moiety oxidized by incubation with a buffer comprising an oxidizing agent selected from the group consisting of sodium periodate (NaIO4), lead tetraacetate (Pb(OAc)4) and potassium peruthenate (KRuO4); wherein an oxime linkage is formed between the oxidized carbohydrate moiety and the active aminooxy group on the fatty acid derivative; and wherein the oxime linkage formation is catalyzed by a nucleophilic catalyst selected from the group consisting of o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

In another embodiment, the aforementioned method is provided wherein the therapeutic protein is selected from the group consisting of: Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor $\alpha 1$, glial cell line-derived neutrophic factor receptor $\alpha 2$, growth related protein, growth related protein $\alpha$, growth related protein $\beta$, growth related protein $\gamma$, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor (SCF), stem cell factor receptor, TNF, TNF0, TNF1, TNF2, transforming growth factor $\alpha$, transforming growth factor $\beta$, transforming growth factor $\beta 1$, transforming growth factor $\beta 1.2$, transforming growth factor $\beta 2$, transforming growth factor $\beta 3$, transforming growth factor $\beta 5$, latent transforming growth factor $\beta 1$, transforming growth factor $\beta$ binding protein I, transforming growth factor $\beta$ binding protein II, transforming growth factor $\beta$ binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, $\alpha$-galactosidase, $\beta$-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), a protein in Table 1, or a biologically active fragment, derivative or variant thereof.

In another embodiment, the aforementioned method is provided wherein the therapeutic protein is FVIIa. In still yet another embodiment, the aforementioned method is provided wherein the therapeutic protein is FVIII. In yet another embodiment, the aforementioned method is provided wherein the therapeutic protein is FIX.

In still another embodiment, the aforementioned method is provided wherein the oxidizing agent is sodium periodate (NaIO4). In another embodiment, the aforementioned method is provided wherein the nucleophilic catalyst is m-toluidine.

In yet another embodiment, the aforementioned method is provided further comprising purifying the conjugated therapeutic protein.

In still another embodiment, the aforementioned method is provided wherein the fatty acid derivative is prepared by a method as described herein.

Still other methods of preparing fatty acid derivatives are contemplated in the present invention. In one embodiment, a method of preparing an aforementioned fatty acid derivative is provided comprising: a) esterifying a carboxyl group on a fatty acid to generate an ester on the fatty acid; and b) coupling a water soluble linker comprising an active maleimide group to a free sulfhydryl (SH) group, thereby forming a stable thioether bond; wherein the fatty acid derivative is water soluble.

In still another embodiment, a method of preparing an aforementioned fatty acid derivative is provided comprising: a) esterifying a carboxyl group on a fatty acid to generate fatty acid ester; b) reacting the fatty acid resulting from step a) with an azide reagent thereby producing a corresponding fatty acid azide; c) hydrogenating the fatty acid azide of step b) to produce a corresponding fatty acid amine; and d) coupling a water soluble linker comprising an active NHS group to a free amine group, thereby forming a stable bond; wherein the fatty acid derivative is water soluble.

In another embodiment, a method of conjugating a water soluble polymer to an oxidized carbohydrate moiety of a blood coagulation protein is provided comprising contacting the oxidized carbohydrate moiety with an activated water soluble polymer under conditions that allow conjugation; the blood coagulation protein selected from the group consisting of Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease or a biologically active fragment, derivative or variant thereof; the water soluble polymer containing an active aminooxy group and is selected from the group consisting of polyethylene glycol (PEG), branched PEG, polysialic acid (PSA), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC); and the carbohydrate moiety oxidized by incubation with a buffer comprising an oxidizing agent selected from the group consisting of sodium periodate (NaIO4), lead tetraacetate (Pb(OAc)$_4$) and potassium peruthenate (KRuO$_4$); wherein an oxime linkage is formed between the oxidized carbohydrate moiety and the active aminooxy group on the water soluble polymer.

FIGURES

FIG. 1 shows the synthesis of the water soluble linker 3-oxapentane-1,5-dioxyamine.

DETAILED DESCRIPTION OF THE INVENTION

The pharmacological and immunological properties of therapeutic proteins can be improved by chemical modification and conjugation with polymeric compounds such as fatty acids and fatty acid derivatives according to the present invention.

The addition of a water soluble fatty acid derivative as described herein is one approach to improve the properties of therapeutic proteins such as the blood coagulation proteins Factor DC (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, tPA, PAI-1, tissue factor (TF) or ADAMTS 13 protease, as well as other known proteins or biologically/therapeutically active fragments thereof.

Therapeutic Proteins

In certain embodiments of the invention, the aforementioned polypeptides and polynucleotides are exemplified by the following therapeutic proteins: enzymes, antigens, antibodies, receptors, blood coagulation proteins, growth factors, hormones, and ligands. In certain embodiments, the therapeutic protein is a blood coagulation protein such as Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, EPA, PAI-1, tissue factor (TF) or ADAMTS 13 protease.

In certain embodiments, the therapeutic protein is immunoglobulins, cytokines such IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), angiopoietins, for example Ang-1, Ang-2, Ang-4, Ang-Y, the human angiopoietin-like polypeptides ANGPTL1 through 7, vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, vascular endothelial growth factor, and chimeric proteins and biologically or immunologically active fragments thereof.

In certain embodiments, the therapeutic protein is alpha-, beta-, and gamma-interferons, colony stimulating factors including granulocyte colony stimulating factors, fibroblast growth factors, platelet derived growth factors, phospholipase-activating protein (PUP), insulin, plant proteins such as lectins and ricins, tumor necrosis factors and related alleles, soluble forms of tumor necrosis factor receptors, interleukin receptors and soluble forms of interleukin receptors, growth factors such as tissue growth factors, such as TGFαs or TGFβs and epidermal growth factors, hormones, somatomedins, pigmentary hormones, hypothalamic releasing factors, antidiuretic hormones, prolactin, chorionic gonadotropin, follicle-stimulating hormone, thyroid-stimulating hormone, tissue plasminogen activator, and immunoglobulins such as IgG, IgE, IgM, IgA, and IgD, a galactosidase, α-galactosidase, β-galactosidase, DNAse, fetuin, leutinizing hormone, estrogen, corticosteroids, insulin, albumin, lipoproteins, fetoprotein, transferrin, thrombopoietin, urokinase, DNase, integrins, thrombin, hematopoietic growth actors, leptin, glycosidases, Humira (adalimumab), Prolia (denosumab), Enbrel (etanercept), and fragments thereof, or any fusion proteins comprising any of the above mentioned proteins or fragments thereof. In addition to the aforementioned proteins, the following Table 1 provides therapeutic proteins contemplated by the present invention:

TABLE 1

| | | |
|---|---|---|
| Follicular dendritic cell secreted peptide | Angiotensin-converting enzyme | Interleukin-1 family member 6 | Herstatin |
| Dermokine | Antithrombin-III | Prostate and testis expressed protein 2 | Leucine-rich repeat-containing protein 28 |
| Secreted frizzled-related protein 1 | Apolipoprotein B-100 | Group XIIA secretory phospholipase A2 | LRRN4 C-terminal-like protein |
| Ectodysplasin-A | Apolipoprotein D | Collagen alpha-3(V) chain | Ly6/PLAUR domain-containing protein 2 |
| Secreted frizzled-related protein 2 | Apolipoprotein E | Alpha-2-macroglobulin-like protein 1 | Transmembrane protein 81 |
| Resistin | Beta-1,4-galactosyltransferase 1 | Dermatopontin | Myelin protein zero-like protein 3 |
| Osteopontin | Bone morphogenetic protein 7 | Cartilage-associated protein | Protein notum homolog |
| Secreted frizzled-related protein 5 | Complement C1q subcomponent subunit B | Desert hedgehog protein | UDP-glucuronosyltransferase 3A2 |
| Secreted frizzled-related protein 4 | C4b-binding protein alpha chain | Extracellular matrix protein 2 | Protocadherin alpha-1 |
| Secreted phosphoprotein 24 | Calreticulin | Gastric intrinsic factor | Phospholipase D4 |
| Glypican-6 | Corticosteroid-binding globulin | Interleukin-33 | Retinol dehydrogenase 10 |
| Secreted frizzled-related protein 3 | Carboxypeptidase A1 | Bone morphogenetic protein 2 | Sialic acid-binding Ig-like lectin 14 |
| C-C motif chemokine 4 | Carboxypeptidase A2 | Bone morphogenetic protein 6 | Transmembrane protein 161A |
| Melanocyte protein Pmel 17 | Eotaxin | Uncharacterized protein KIAA0564 | Transmembrane protein 161B |
| Secreted Ly-6/uPAR-related protein 1 | C-C motif chemokine 13 | Cerberus | Transmembrane protein 182 |
| Beta-microseminoprotein | C-C motif chemokine 18 | Carbohydrate sulfotransferase 8 | Protein FAM24B |
| Glypican-4 | C-C motif chemokine 20 | Contactin-associated protein-like 3 | Transmembrane protein 52 |
| Tumor necrosis factor ligand superfamily member 15 | Triggering receptor expressed on myeloid cells 2 | Group XIIB secretory phospholipase A2-like protein | Major facilitator superfamily domain-containing protein 4 |
| Resistin-like beta | C-C motif chemokine 2 | Corticoliberin | UDP-glucuronosyltransferase 2A3 |
| Tumor necrosis factor ligand superfamily member 12 | Transforming growth factor-beta-induced protein ig-h3 | A disintegrin and metalloproteinase with thrombospondin motifs 19 | Odontogenic ameloblast-associated protein |
| SPARC | CD40 ligand | UPF0556 protein C19orf10 | Neurosecretory protein VGF |
| Glypican-5 | Comeodesmosin | C—X—C motif chemokine 3 | Secreted phosphoprotein 2, 24 kDa |
| Anterior gradient protein 2 homolog | Complement factor D | Cystatin-M | Protein FAM150B |
| Protein canopy homolog 2 | Chromogranin-A | Defensin-5 | Growth/differentiation factor 9 |
| von Willebrand factor A domain-containing protein 2 | Collagen alpha-1(I) chain | Defensin-6 | Clusterin-like protein 1 |
| WNT1-inducible-signaling pathway protein 1 | Disintegrin and metalloproteinase domain-containing protein 18 | A disintegrin and metalloproteinase with thrombospondin motifs 18 | Transmembrane and immunoglobulin domain-containing protein 2 |
| C-C motif chemokine 1 | Cysteine-rich secretory protein LCCL domain-containing 1 | A disintegrin and metalloproteinase with thrombospondin motifs 3 | C-type lectin domain-containing protein UNQ5810/PRO19627 |
| SPARC-related modular calcium-binding protein 2 | Collagen alpha-4(IV) chain | Dickkopf-related protein 4 | Epididymal-specific lipocalin-10 |
| C-type lectin domain family 11 member A | Keratinocyte differentiation-associated protein | A disintegrin and metalloproteinase with thrombospondin motifs 5 | Epididymal-specific lipocalin-8 |
| Secreted Ly-6/uPAR-related protein 2 | Complement C4-B | Mammalian ependymin-related protein 1 | Basic proline-rich peptide P-E |
| Glypican-3 | Collagen alpha-2(V) chain | Fibrillin-3 | Putative uncharacterized protein C10orf99 |
| Secreted and transmembrane protein 1 | Complement C5 | Fetuin-B | Uncharacterized protein C17orf77 |
| Testis-expressed sequence 264 protein | Collagen alpha-1(VII) chain | Fibroblast growth factor 6 | Arylacetamide deacetylase-like 2 |
| Glypican-2 | Complement component C7 | Keratinocyte growth factor | Epididymal-specific lipocalin-12 |
| Serine protease 23 | Complement component C8 beta chain | Growth/differentiation factor 8 | B melanoma antigen 2 |
| 39S ribosomal protein L55, mitochondrial | Complement component C8 gamma chain | Gastric inhibitory polypeptide | B melanoma antigen 3 |
| Protein NipSnap homolog 3A | Collagen alpha-1(XV) chain | Glycoprotein hormone beta-5 | Bovine seminal plasma protein homolog 1 |
| Fibronectin | Collagen alpha-1(XVI) chain | Granzyme M | Complement C1q-like protein 3 |
| Neudesin | Collagen alpha-1(XVIII) chain | Gastrin-releasing peptide | UPF0565 protein C2orf69 |
| Fibroblast growth factor receptor 2 | Collagen alpha-1(XIX) chain | Serine protease HTRA1 | UPF0669 protein C6orf120 |
| Carbonic anhydrase 6 | Cartilage oligomeric matrix protein | Interferon alpha-4 | Colipase-like protein C6orf127 |
| Deleted in malignant brain tumors 1 protein | C-reactive protein | Interferon alpha-5 | Uncharacterized protein C7orf69 |
| SPARC-related modular calcium-binding protein 1 | Granulocyte colony-stimulating factor | Interferon alpha-7 | Platelet-derived growth factor receptor-like protein |
| Amyloid beta A4 protein | Granulocyte-macrophage colony-stimulating factor | A disintegrin and metalloproteinase with thrombospondin motifs 7 | Chondroadherin-like protein |
| | Protein CYR61 | Immunoglobulin superfamily member 10 | |

TABLE 1-continued

| | | |
|---|---|---|
| Tumor necrosis factor receptor superfamily member 6 | Complement component receptor 1-like protein | Protease-associated domain-containing protein of 21 kDa |
| Gamma-aminobutyric acid type B receptor subunit 1 | Stem cell growth factor; lymphocyte secreted C-type lectin | Abhydrolase domain-containing protein FAM108A1 |
| Pro-neuregulin-1, membrane-bound isoform | CMP-N-acetylneuraminate-beta-galactosamide-alpha-2,3-sialyltransferase | A disintegrin and metalloproteinase with thrombospondin motifs 9 |
| Glycoprotein hormone alpha-2 | Dipeptidyl peptidase 4 | Interleukin-9 receptor |
| Membrane metallo-endopeptidase-like 1 | Dentin sialophosphoprotein | Interleukin-9 |
| Fc receptor-like A | Endothelin-1 | Inhibin beta B chain |
| C-C motif chemokine 4-like | Ephrin-B1 | Serine protease inhibitor Kazal-type 2 |
| Epithelial discoidin domain-containing receptor 1 | Epidermis-specific serine protease-like protein | BMP-binding endothelial regulator protein |
| Mucin-1 | EMILIN-1 | Keratinocyte-associated protein 2 |
| Vascular endothelial growth factor A | Endoplasmin | Laminin subunit alpha-1 |
| Fibulin-1 | Ephrin type-A receptor 3 | Leukocyte cell-derived chemotaxin-2 |
| Prolactin receptor | Ephrin type-B receptor 6 | Gastric triacylglycerol lipase |
| Proprotein convertase subtilisin/kexin type 6 | Glycosyltransferase 1 domain-containing protein 1 | Leucine-rich repeat and calponin homology domain-containing protein 3 |
| CD209 antigen | Coagulation factor X | Pancreatic lipase-related protein 2 |
| Collagen alpha-2(XI) chain | Coagulation factor VIII | Epididymis-specific alpha-mannosidase |
| Granulocyte-macrophage colony-stimulating factor receptor subunit alpha | Complement C1q tumor necrosis factor-related protein 7 | Fibronectin type III domain-containing protein 7 |
| Elastin | Fibrillin-2 | Microfibrillar-associated protein 5 |
| Interleukin-15 receptor subunit alpha | Alpha-2-HS-glycoprotein | Muellerian-inhibiting factor |
| Midkine | Fibroblast growth factor 10 | Matrix metalloproteinase-21 |
| Integrin alpha-7 | Fibrinogen alpha chain | Matrix metalloproteinase-17 |
| Mucin-4 | Fibrinogen beta chain | Matrix metalloproteinase-20 |
| Peptidyl-glycine alpha-amidating monooxygenase | Long palate, lung and nasal epithelium carcinoma-associated protein 1 | N-acetylglucosamine-1-phosphotransferase subunit gamma |
| Apolipoprotein A-I | Gastrin | Multimerin-2 |
| Proteoglycan 4 | Glycoprotein hormones alpha chain | Promotilin |
| Tumor necrosis factor receptor superfamily member 25 | N-acetylglucosamine-1-phosphotransferase subunits alpha/beta | FRAS1-related extracellular matrix protein 3 |
| Attractin | Granzyme A | Protein kinase C-binding protein NELL1 |
| Prostate-associated microseminoprotein | Hepatocyte growth factor-like protein | Protein kinase C-binding protein NELL2 |
| Alpha-amylase 1 | Insulin-like growth factor-binding protein 1 | Neurotrypsin |
| Brain-derived neurotrophic factor | Insulin-like growth factor-binding protein 2 | Neuroserpin |
| C-type lectin domain family 4 member M | Insulin-like growth factor-binding protein 4 | Nidogen-2 |
| Granulocyte colony-stimulating factor receptor | Tumor necrosis factor receptor superfamily member 12A | Abhydrolase domain-containing protein FAM108B1 |
| Insulin-like growth factor II | Interferon alpha-1/13 | Neurotrophin-4 |
| Carcinoembryonic antigen-related cell adhesion molecule 1 | Interferon-induced helicase C domain-containing protein 1 | Epididymal secretory glutathione peroxidase |
| C-type lectin domain family 7 member A | Interferon alpha-2 | Group 10 secretory phospholipase A2 |
| CMRF35-like molecule 1 | Interferon beta | Group IID secretory phospholipase A2 |
| Choline transporter-like protein 4 | Interferon gamma | Lactoperoxidase |
| Pulmonary surfactant-associated protein A1 | Insulin-like growth factor IB | p53 apoptosis effector related to PMP-22 |
| Spermine oxidase | Indian hedgehog protein | Placenta-specific protein 1 |
| CMP-N-acetylneuraminate-beta-1,4-galactoside alpha-2,3-sialyltransferase | Neural cell adhesion molecule L1-like protein | Tuberoinfundibular peptide of 39 residues |
| Kallikrein-8 | Interleukin-13 | Prolargin |
| Tissue-type plasminogen activator | Interleukin-2 | Secretogranin-2 |
| Peroxisomal N(-)-acetyl- | Chymotrypsin-like elastase family | Endonuclease domain-containing 1 |
| | | Putative uncharacterized protein UNQ6490/PRO21339 |
| | | Putative uncharacterized protein UNQ6493/PRO21345 |
| | | Putative uncharacterized protein UNQ5815/PRO19632 |
| | | Cystatin-A |
| | | Peptidase inhibitor R3HDML |
| | | Cystatin-9 |
| | | DAN domain family member 5 |
| | | Insulin-like growth factor-binding protein-like 1 |
| | | Epididymal sperm-binding protein 1 |
| | | Elafin |
| | | Protein FAM55A |
| | | Growth/differentiation factor 6 |
| | | Glucose-fructose oxidoreductase domain-containing protein 1 |
| | | Erythropoietin |
| | | Glutathione peroxidase 6 |
| | | Uncharacterized protein UNQ511/PRO1026 |
| | | Beta-defensin 128 |
| | | Interleukin-31 |
| | | Interleukin-34 |
| | | Plasma kallikrein-like protein 4 |
| | | Epididymal-specific lipocalin-9 |
| | | cDNA FLJ60957, highly similar to Secreted frizzled-related protein 4 |
| | | Lipase member M |
| | | CLECSF12 |
| | | Putative inactive group IIC secretory phospholipase A2 |
| | | Serine protease MPN2 |
| | | Netrin-5 |
| | | NHL repeat-containing protein 3 |
| | | Olfactomedin-like protein 2B |
| | | Ovochymase-2 |
| | | Putative uncharacterized protein UNQ3029/PRO9830 |
| | | Ovochymase-1 |
| | | Putative pregnancy-specific beta-1-glycoprotein 7 |
| | | Ovostatin homolog 2 |
| | | Orexigenic neuropeptide QRFP |
| | | Lymphocyte antigen 6K |
| | | Prostate and testis expressed protein 1 |
| | | Putative phospholipase B-like 1 |
| | | Putative uncharacterized protein FLJ42147 |
| | | Otogelin |
| | | Ribonuclease 8 |
| | | Nuclear pore complex-interacting protein- |

TABLE 1-continued

| | |
|---|---|
| spermine/spermidine oxidase | member 2A |
| Probable palmitoyltransferase ZDHHC4 | Inhibin beta-A chain |
| Cholesteryl ester transfer protein | Pancreatic secretory trypsin inhibitor |
| HLA class I histocompatibility antigen, A-2 alpha chain | Tumor necrosis factor receptor superfamily member 21 |
| Collagen alpha-1(II) chain | Inter-alpha-trypsin inhibitor heavy chain H1 |
| Pro-interleukin-16 | Inter-alpha-trypsin inhibitor heavy chain H2 |
| Leptin receptor | Inter-alpha-trypsin inhibitor heavy chain H3 |
| Decorin | Prostate-specific antigen |
| Stromal cell-derived factor 1 | Kallikrein-4 |
| Tenascin | Plasma kallikrein |
| Disintegrin and metalloproteinase domain-containing protein 12 | Calcium-activated chloride channel regulator 4 |
| A disintegrin and metalloproteinase with thrombospondin motifs 13 | Bactericidal/permeability-increasing protein-like 1 |
| T-cell surface glycoprotein CD8 alpha chain | Leptin |
| EGFR-coamplified and overexpressed protein | A disintegrin and metalloproteinase with thrombospondin motifs 4 |
| Autophagy-related protein 16-1 | Hepatic triacylglycerol lipase |
| Breast cancer anti-estrogen resistance protein 3 | Lymphocyte antigen 6 complex locus protein G6c |
| Cadherin-23 | Eosinophil lysophospholipase |
| Macrophage colony-stimulating factor 1 | Lutropin subunit beta |
| Folate receptor alpha | Microfibrillar-associated protein 1 |
| Low-density lipoprotein receptor-related protein 8 | Mesencephalic astrocyte-derived neurotrophic factor |
| E3 ubiquitin-protein ligase LRSAM1 | Matrix Gla protein |
| Neural cell adhesion molecule 1 | 72 kDa type IV collagenase |
| Neuroligin-4, X-linked | Stromelysin-1 |
| Netrin-G1 | Neutrophil collagenase |
| GPI transamidase component PIG-T | Mesothelin |
| Kit ligand | Mucin-5AC |
| Seizure 6-like protein | Mucin-6 |
| SLAM family member 7 | Norrin |
| Tumor necrosis factor | Oxytocin-neurophysin 1 |
| Uromodulin | Beta-nerve growth factor |
| Tumor necrosis factor ligand superfamily member 13 | Tumor necrosis factor ligand superfamily member 18 |
| Protein CREG1 | Neurotrophin-3 |
| EGF-like domain-containing protein 8 | Platelet-derived growth factor subunit A |
| Aminoacyl tRNA synthetase complex-interacting multifunctional protein 1 | Phosphopantothenoylcysteine decarboxylase |
| ADAMTS-like protein 4 | Plasminogen activator inhibitor 1 |
| Coagulation factor XI | Plasminogen activator inhibitor 2 |
| Interleukin-22 receptor subunit alpha-2 | Procollagen C-endopeptidase enhancer 1 |
| Deformed epidermal autoregulatory factor 1 homolog | Transmembrane and ubiquitin-like domain-containing protein 2 |
| Prostaglandin-H2 D-isomerase | Protein disulfide-isomerase |
| Alpha-1-antitrypsin | Pigment epithelium-derived factor |
| Alpha-1-antichymotrypsin | Pepsin A |
| Acyl-CoA-binding protein | Gastricsin |
| Complement factor B | Sonic hedgehog protein |
| Choriogonadotropin subunit beta | Peptidoglycan recognition protein I-alpha |
| protein | Semaphorin-3B |
| like 2 | Proactivator polypeptide-like 1 |
| | Protein spinster homolog 2 |
| Somatostatin | von Willebrand factor C domain-containing protein 2-like |
| Dehydrogenase/reductase SDR family member 4-like 2 | Urotensin-2B |
| Transcobalamin-1 | Tetraspanin-18 |
| Trefoil factor 2 | UPF0514 membrane protein FAM159A |
| Testican-1 | Latherin |
| Serum paraoxonase/lactonase 3 | Methyltransferase-like protein 7B |
| Tolloid-like protein 2 | Protein TEX261 |
| Trypsin-2 | Alkylated DNA repair protein alkB homolog 7 |
| RING finger and SPRY domain-containing protein 1 | Transmembrane emp24 domain-containing protein 6 |
| Calcium-binding and coiled-coil domain-containing protein 1 | XK-related protein 5 |
| Protein Wnt-2 | Putative V-set and immunoglobulin domain-containing protein 7 |
| Ectonucleoside triphosphate diphosphohydrolase 8 | Insulin growth factor-like family member 3 |
| Protein Wnt-8b | Nuclear pore complex-interacting protein-like 1 |
| UDP-GlcNAc:betaGal beta-1,3-N-acetylglucosaminyltransferase 4 | Secreted phosphoprotein 1 |
| EMI domain-containing protein 1 | Collagen alpha-5(VI) chain |
| Uncharacterized protein C6orf15 | B melanoma antigen 5 |
| Collectin-10 | WAP four-disulfide core domain protein 10A |
| Long-chain-fatty-acid--CoA ligase ACSBG2 | UPF0369 protein C6orf57 |
| Oncoprotein-induced transcript 3 protein | Putative uncharacterized protein C10orf31 |
| Peptidase inhibitor 15 | Putative uncharacterized protein C11orf45 |
| Proline-rich acidic protein 1 | Uncharacterized protein C12orf28 |
| Urocortin | Uncharacterized protein C17orf67 |
| Trypsin-X3 (EC 3.4.21.4) | Beta-defensin 121 |
| HHIP-like protein 2 | Beta-defensin 130 |
| Fractalkine | Histidine triad nucleotide-binding protein 2 |
| Protein Wnt-11 | Apelin |
| Protein Wnt-7a | Placenta-specific protein 9 |
| FCH and double SH3 domains protein 1 | Hepatocellular carcinoma-associated protein TD26 |
| Hepatoma-derived growth factor-related protein 2 | Persephin |
| Interleukin-12 subunit alpha | Regulated endocrine-specific protein 18 |
| UPF0577 protein KIAA1324 | Complement C1q tumor necrosis factor-related protein 8 |
| Complement C1q tumor necrosis factor-related protein 9 | Bone morphogenetic protein 8A |
| Mucin-17 | Protein Wnt-8a |
| Lysosomal protein NCU-G1 | Ig-like domain-containing protein ENSP00000270642 |
| Prolyl 4-hydroxylase subunit alpha-3 | Ribonuclease-like protein 9 |
| Peptidyl-prolyl cis-trans isomerase SDCCAG10 | Abhydrolase domain-containing protein 15 |
| Peptidase inhibitor 16 | Uncharacterized protein C2orf66 |
| Poliovirus receptor-related protein 4 | Uncharacterized protein C17orf99 |
| Solute carrier family 22 member 15 | Protein FAM150A |
| GPI inositol-deacylase | Placenta-specific 1-like protein |
| Transmembrane protein 43 | |
| Angiopoietin-related protein 2 | |

TABLE 1-continued

| Column 1 | Column 2 | Column 3 |
|---|---|---|
| Versican core protein | Biglycan | Angiopoietin-related protein 6 | Uncharacterized protein C18orf20 |
| Epidermal growth factor receptor | Prolactin-inducible protein | Arylsulfatase K | Beta-defensin 110 |
| Ecto-NOX disulfide-thiol exchanger 2 | Platelet factor 4 | Augurin | Neuritin-like protein |
| Hyaluronidase-1 | Plasminogen | Brain-specific serine protease 4 | Histidine-rich carboxyl terminus protein 1 |
| Interleukin-1 receptor antagonist protein | Serum paraoxonase/arylesterase 1 | DBH-like monooxygenase protein 1 | C-type lectin domain family 2 member A |
| Interleukin-6 receptor subunit beta | Alkaline phosphatase, placental type | Uncharacterized protein C1orf56 | Leucine-rich repeat-containing protein 70 |
| Interleukin-1 receptor-like 1 | Peptidyl-prolyl cis-trans isomerase B | Cerebellin-3 | Serpin A13 |
| Insulin | Bone marrow proteoglycan | Cerebellin-4 | BTB/POZ domain-containing protein 17 |
| Glycodelin | Basic salivary proline-rich protein 1 | Colipase-like protein C6orf126 | Uncharacterized protein C12orf53 |
| Parathyroid hormone-related protein | Pulmonary surfactant-associated protein C | Uncharacterized protein C11orf83 | C-type lectin domain family 9 member A |
| Nurim | Parathyroid hormone | Uncharacterized protein C16orf89 | Complement C1q-like protein 4 |
| Prolyl 4-hydroxylase subunit alpha-2 | Serum amyloid P-component | Carboxypeptidase-like protein X2 | CMRF35-like molecule 4 |
| CD276 antigen | Secretogranin-1 | Cystatin-9-like | Protein FAM151B |
| Cysteine-rich with EGF-like domain protein 1 | Basement membrane-specific heparan sulfate proteoglycan core protein | Dehydrogenase/reductase SDR family member 13 | Abhydrolase domain-containing protein FAM108A2/A3 |
| CUB and sushi domain-containing protein 1 | Antileukoproteinase | Beta-defensin 123 | Osteocrin |
| Ficolin-2 | Stabilin-1 | Beta-defensin 132 | Transmembrane protease, serine 11E2 |
| Fc receptor-like protein 5 | Extracellular superoxide dismutase [Cu—Zn] | Cytokine-like protein 1 | Transmembrane protein 14E |
| Protein GPR89 | Somatotropin | Dickkopf-related protein 2 | Transmembrane protein 207 |
| Junctional adhesion molecule A | Serpin B5 | Dickkopf-like protein 1 | TOMM20-like protein 1 |
| Leucine-rich repeat-containing protein 8A | Spondin-1 | Epididymal secretory protein E3-beta | Uncharacterized protein C3orf41 |
| Multiple inositol polyphosphate phosphatase 1 | Structural maintenance of chromosomes protein 3 | EGF-like repeat and discoidin I-like domain-containing protein 3 | Submaxillary gland androgen-regulated protein 3A |
| Neuropilin-1 | Syntaxin-1A | Protein FAM55D | B melanoma antigen 1 |
| Plexin-A4 | Tetranectin | Fibroblast growth factor 17 | Inactive carboxylesterase 4 |
| Plexin-B1 | Transforming growth factor beta-1 | Fibroblast growth factor 22 | Four-jointed box protein 1 |
| Periostin | Thyroglobulin | Fibroblast growth factor-binding protein 2 | Protein HSN2 |
| Protein RIC-3 | Metalloproteinase inhibitor 1 | Growth/differentiation factor 3 | Humanin |
| SLIT and NTRK-like protein 2 | Metalloproteinase inhibitor 2 | GLIPR1-like protein 1 | Kielin/chordin-like protein |
| Sulfatase-modifying factor 1 | Metalloproteinase inhibitor 3 | Serine protease inhibitor Kazal-type 6 | UPF0624 protein C6orf186 |
| Sulfatase-modifying factor 2 | Urokinase-type plasminogen activator | Interleukin-17B | Putative neurofibromin 1-like protein 4/6 |
| Transmembrane protease, serine 6 | Lactotransferrin | Interleukin-17C | Peroxidasin-like protein |
| Lymphotoxin-alpha | Trypsin-1 | Interleukin-17D | SCO-spondin |
| Tumor necrosis factor receptor superfamily member 10B | Submaxillary gland androgen-regulated protein 3B | Hyaluronan and proteoglycan link protein 3 | Putative uncharacterized protein UNQ9165/PRO28630 |
| Urokinase plasminogen activator surface receptor | Tumor necrosis factor receptor superfamily member 1A | Vitelline membrane outer layer protein 1 homolog | Calcium-activated chloride channel regulator family member 3 |
| V-set domain-containing T-cell activation inhibitor 1 | Vascular endothelial growth factor receptor 1 | Choriogonadotropin subunit beta variant 1 | Probable serine protease UNQ9391/PRO34284 |
| Glucagon | Vitamin D-binding protein | Lysozyme-like protein 1 | Uncharacterized protein C4orf26 |
| N-acetylmuramoyl-L-alanine amidase | Vitronectin | Matrix metalloproteinase-28 | Uncharacterized protein C4orf40 |
| Sulfhydryl oxidase 1 | von Willebrand factor | Nephronectin | Uncharacterized protein C5orf55 |
| Dehydrogenase/reductase SDR family member 4 | Lymphocyte antigen 6 complex locus protein G5c | WAP four-disulfide core domain protein 12 | Putative macrophage-stimulating protein MSTP9 |
| Interleukin-18-binding protein | Zinc-alpha-2-glycoprotein | Olfactomedin-like protein 1 | Uncharacterized protein C15orf61 |
| Kin of IRRE-like protein 2 | Uncharacterized protein C14orf93 | Olfactomedin-like protein 2A | Chymotrypsinogen B2 |
| Myeloid-associated differentiation marker | Retinoschisin | Serine protease 27 | Beta-defensin 108A |
| Chordin | Alpha-1,3-mannosyltransferase ALG2 | Secretoglobin family 3A member 2 | Beta-defensin 111 |
| 1-acyl-sn-glycerol-3-phosphate acyltransferase gamma | C-type lectin domain family 11, member A, isoform CRA_b | A disintegrin and metalloproteinase with thrombospondin motifs 2 | Putative V-set and immunoglobulin domain-containing protein 6 |
| Advanced glycosylation end product-specific receptor | Major facilitator superfamily domain-containing protein 7 | Disintegrin and metalloproteinase domain-containing protein 28 | Serine protease inhibitor Kazal-type 5-like 3 |
| NLR family CARD domain-containing | Leucine-rich repeat transmembrane | Bactericidal/permeability-increasing | Putative serine protease inhibitor Kazal- |

TABLE 1-continued

| | |
|---|---|
| protein 4 | protein-like 2 |
| Pro-neuregulin-2, membrane-bound isoform | Acid sphingomyelinase-like phosphodiesterase 3b |
| Sperm-associated antigen 11A | Serine protease inhibitor Kazal-type 7 |
| Oocyte-secreted protein 1 homolog | Neurexophilin-4 |
| Serum albumin | Protein Wnt-9b |
| Cochlin | Zymogen granule protein 16 homolog B |
| Plasma protease C1 inhibitor | Semaphorin-3D |
| Interleukin-7 receptor subunit alpha | Apolipoprotein L4 |
| Inter-alpha-trypsin inhibitor heavy chain H5 | Transmembrane protease, serine 11D |
| Platelet-derived growth factor D | Scrapie-responsive protein 1 |
| Protein S100-A7 | Putative annexin A2-like protein |
| Sialic acid-binding Ig-like lectin 10 | Bone morphogenetic protein 10 |
| Tubulointerstitial nephritis antigen-like | Secretogranin-3 |
| Tumor necrosis factor ligand superfamily member 13B | Complement C1q tumor necrosis factor-related protein 4 |
| Long-chain-fatty-acid—CoA ligase 5 | Uncharacterized protein C1orf54 |
| Claudin-14 | Carboxypeptidase A6 |
| Leucine-rich repeat-containing protein 20 | C-C motif chemokine 19 |
| Interleukin-1 family member 7 | C-C motif chemokine 25 |
| Lymphocyte antigen 6 complex locus protein G5b | Chymotrypsin-like elastase family member 2B |
| Acetylcholinesterase | Protein CEI |
| Amelogenin, X isoform | Uncharacterized protein C6orf |
| Angiogenin | Uncharacterized protein C7orf34 |
| Anthrax toxin receptor 2 | Keratinocyte-associated protein 3 |
| Annexin A2 | Uncharacterized protein C9orf47 |
| Apolipoprotein C-III | Collagen alpha-1(VIII) chain |
| Apolipoprotein L1 | Uncharacterized protein C18orf54 |
| Complement C1q subcomponent subunit A | Cystatin-like 1 |
| Complement C1q subcomponent subunit C | C2 domain-containing protein 2 |
| Calcitonin | DDRGK domain-containing protein 1 |
| Soluble calcium-activated nucleotidase 1 | Protein FAM55C |
| C-C motif chemokine 15 | Collagen alpha-1(XXVI) chain |
| CD97 antigen ( | Protein FAM19A2 |
| Contactin-4 | Protein FAM5B |
| Complement C2 | Fibroblast growth factor 5 |
| Collagen alpha-6(IV) chain | Probable serine protease HTRA3 |
| Collagen alpha-2(VI) chain | Interleukin-1 family member 8 |
| Collagen alpha-1(XI) chain | Serine protease inhibitor Kazal-type 4 |
| Crumbs homolog 1 | Otospiralin |
| Cystatin-C | Liver-expressed antimicrobial peptide 2 |
| Neutrophil defensin 1 | Lysyl oxidase homolog 1 |
| Endothelin-3 | Lysyl oxidase homolog 2 |
| Low affinity immunoglobulin epsilon Fc receptor | Long palate, lung and nasal epithelium carcinoma-associated protein 4 |
| Fibroblast growth factor receptor 3 | Lysozyme g-like protein 2 |
| Fibroblast growth factor receptor 4 | Endomucin |
| Growth arrest-specific protein 6 | Neuropeptide B |
| Growth hormone receptor | Kinesin-like protein KIF7 |
| Bifunctional UDP-N-acetylglucosamine 2-epimerase/N-acetylmannosamine kinase | Leukocyte-associated immunoglobulin-like receptor 2 |
| Immunoglobulin superfamily member 8 | Calcium-dependent phospholipase A2 |
| neuronal protein 1 | type 5-like 2 |
| NADH dehydrogenase [ubiquinone] 1 beta subcomplex subunit 11, mitochondrial | Dehydrogenase/reductase SDR family member 7C |
| UPF0546 membrane protein C1orf91 | Beta-defensin 131 |
| Carbonic anhydrase-related protein 10 | Beta-defensin 134 |
| Cholecystokinin | Beta-defensin 136 |
| Codanin-1 | Beta-defensin 116 |
| Uncharacterized protein C6orf89 | Protein FAM132A |
| Chondroitin sulfate glucuronyltransferase | Protein FAM132B |
| Chitinase domain-containing protein 1 | Beta-defensin 115 |
| Transmembrane protein C9orf7 | Beta-defensin 114 |
| CMRF35-like molecule 9 | Serine protease inhibitor Kazal-type 9 |
| Cytochrome P450 2S1 | Lipase member N |
| Crumbs protein homolog 3 | Pancreatic lipase-related protein 3 |
| Dehydrogenase/reductase SDR family member 7 | Testis, prostate and placenta-expressed protein |
| Protein ENED | Neuromedin-S |
| Complement factor H-related protein 4 | Neuropeptide S |
| Leucine-rich repeat LGI family member 3 | Neuronal pentraxin-like protein C16orf38 |
| Gliomedin | Otolin-1 |
| Glycerophosphodiester phosphodiesterase domain-containing protein 5 | Iron/zinc purple acid phosphatase-like protein |
| Probable G-protein coupled receptor 113 | Ovostatin homolog 1 |
| Probable G-protein coupled receptor 114 | Plasminogen-related protein A |
| Glycerol-3-phosphate acyltransferase 4 | Polyserase-3 |
| Gremlin-1 | Putative peptide YY-2 |
| Potassium channel subfamily K member 17 | Putative peptide YY-3 |
| KDEL motif-containing protein 2 | Ribonuclease-like protein 10 |
| Layilin | Ribonuclease-like protein 12 |
| Leucine-rich repeat-containing protein 8B | Ribonuclease-like protein 13 |
| Leucine-rich repeat-containing protein 8D | Serpin A11 |
| Sialic acid-binding Ig-like lectin 15 | Kunitz-type protease inhibitor 4 |
| Pregnancy-specific beta-1-glycoprotein 2 | Meteorin-like protein |
| Ly6/PLAUR domain-containing protein 1 | Putative testis serine protease 2 |
| Ly6/PLAUR domain-containing protein 5 | Beta-defensin 112 |
| MLN64 N-terminal domain homolog | Uncharacterized protein FLJ37543 |
| Macrophage migration inhibitory factor | Protein FAM24A |
| 2-acylglycerol O-acyltransferase 3 | Secreted frizzled-related protein 4 |
| Mitochondrial carrier homolog 1 | Complement C1q-like protein 2 |
| Apolipoprotein L6 | Putative uncharacterized protein C17orf69 |
| Protocadherin alpha-6 | Putative cystatin-13 |
| Protocadherin gamma-A12 | Beta-defensin 109 |
| R-spondin-4 | Beta-defensin 113 |
| Voltage-gated hydrogen channel 1 | Beta-defensin 135 |
| All-trans-retinol 13,14-reductase | Peptidase S1 domain-containing protein LOC136242 |
| Long-chain fatty acid transport protein 3 | Growth/differentiation factor 7 |
| Vesicle-trafficking protein SEC22c | IgA-inducing protein homolog |
| Claudin-1 | Putative lipocalin 1-like protein 1 |
| Leucine-rich repeats and immunoglobulin-like domains protein 3 | Putative serine protease 29 |
| SLAM family member 9 | Putative scavenger receptor cysteine-rich domain-containing protein LOC619207 |
| | Secretoglobin-like protein |

TABLE 1-continued

| | | |
|---|---|---|
| Interleukin-4 receptor alpha chain | Transthyretin | Proapoptotic caspase adapter protein | Putative stereocilin-like protein |
| Kallikrein-14 | Serine/threonine-protein kinase 32B | Integrin beta-like protein 1 | Insulin growth factor-like family member 2 |
| Kallikrein-6 | Platelet-derived growth factor subunit B | Tolloid-like protein 1 | KIR2DL4 |
| Laminin subunit beta-3 | Noggin | Kunitz-type protease inhibitor 3 | Putative zinc-alpha-2-glycoprotein-like 1 |
| Leucyl-cystinyl aminopeptidase | Tryptase alpha-1 | Protein TMEM155 | Insulin growth factor-like family member 4 |
| Mannan-binding lectin serine protease 1 | Tetratricopeptide repeat protein 14 | Prosalusin | Uncharacterized protein C2orf72 |
| Mannan-binding lectin serine protease 2 | XTP3-transactivated gene B protein | Protein amnionless | Replication initiation-like protein |
| Neutrophil gelatinase-associated lipocalin | Palmitoyltransferase ZDHHC15 | Protein WFDC10B | Prostate and testis expressed protein 3 |
| Neuropeptide Y | Zona pellucida sperm-binding protein 3 | WAP four-disulfide core domain protein 8 | B melanoma antigen 4 |
| Aggrecan core protein | Leucine-rich repeat-containing protein 39 | Protein Wnt-5b | Putative uncharacterized protein C1orf191 |
| Pulmonary surfactant-associated protein B | Pancreatic triacylglycerol lipase | Protein Wnt-7b | Beta-defensin 108B-like |
| Poliovirus receptor-related protein 1 | Transmembrane protein 139 | Zona pellucida-binding protein 2 | Uncharacterized protein FLJ90687 |
| Renin | Leukemia inhibitory factor | SH3 domain-binding protein 5-like | Secreted frizzled-related protein 2 |
| Ribonuclease pancreatic | Galectin-1 | Adipocyte adhesion molecule | Basic proline-rich peptide IB-1 |
| Semenogelin-1 | C-C motif chemokine 21 | Uncharacterized protein C12orf59 | Fibroblast growth factor 16 |
| Signaling lymphocytic activation molecule | CD5 antigen-like | Apolipoprotein A-I-binding protein | Serine protease inhibitor Kazal-type 8 |
| Tissue factor pathway inhibitor | Carbohydrate sulfotransferase 9 | Claudin-17 | Uncharacterized protein KIAA0495 |
| Usherin | Lipopolysaccharide-binding protein | Inactive caspase-12 | Platelet basic protein-like 2 |
| Fibroblast growth factor 23 | Cysteine-rich motor neuron 1 protein | Uncharacterized protein C7orf58 | Serpin E3 |
| Interleukin-23 subunit alpha | Connective tissue growth factor | Collagen alpha-1(XXVIII) chain | CR1 receptor |
| Epididymal secretory protein E1 | Protein eyes shut homolog | Dentin matrix protein 4 | Secreted phosphoprotein 1 |
| ADAMTS-like protein 1 | Mucin-like protein 1 | Uncharacterized protein C16orf48 | Stress induced secreted protein 1 |
| Chemokine-like factor | Fibroblast growth factor 19 | Carboxylesterase 3 | Protein Wnt |
| EGF-like domain-containing protein 7 | Follistatin-related protein 3 | Protein FAM20B | Protein Wnt (Fragment) |
| Tectonic-1 | Hedgehog-interacting protein | GPN-loop GTPase 3 | Putative serine protease LOC138652 |
| Transmembrane protein 25 | Interleukin-17 receptor B | GRAM domain-containing protein 1B | TOM1 |
| UDP-GalNAc:beta-1,3-N-acetylgalactosaminyltransferase 1 | FXYD domain-containing ion transport regulator 5 | Phosphatidylinositol glycan anchor biosynthesis class U protein | Putative uncharacterized protein FLJ46089 |
| Interleukin-15 (IL-15) | Endothelial lipase | Interleukin-27 subunit alpha | Putative uncharacterized protein C1orf134 |
| Multiple epidermal growth factor-like domains 11 | EGF-containing fibulin-like extracellular matrix protein 2 | Pro-neuregulin-4, membrane-bound isoform | UDP-GlcNAc:betaGal beta-1,3-N-acetylglucosaminyltransferase 9 |
| Mucin and cadherin-like protein | Otoraplin | Leucine-rich repeat neuronal protein 3 | Uncharacterized protein C11orf44 |
| Ribonuclease 4 | Group 3 secretory phospholipase A2 | NMDA receptor-regulated protein 2 | Uncharacterized protein C12orf73 |
| SH2 domain-containing protein 3C | Group XV phospholipase A2 | NADH-cytochrome b5 reductase 1 | Putative cystatin-9-like 2 |
| CMP-N-acetylneuraminate-beta-galactosamide-alpha-2,3-sialyltransferase | Tumor necrosis factor ligand superfamily member 14 | Parkinson disease 7 domain-containing protein 1 | Putative abhydrolase domain-containing protein FAM108A5 |
| Transmembrane protein 9 | Plexin-A2 | FK506-binding protein 11 | Beta-defensin 133 |
| WAP four-disulfide core domain protein 2 | Papilin | C-type lectin domain family 12 member B | Fibrosin-1 |
| Adenosine A3 receptor | Prokineticin-1 | Solute carrier family 35 member F5 | Probable folate receptor delta |
| Gamma-secretase subunit APH-1A | Ribonuclease 7 | Sialic acid-binding Ig-like lectin 12 | RPE-spondin |
| Basigin | Kunitz-type protease inhibitor 1 | Protein FAM19A3 | NPIP-like protein ENSP00000346774 |
| Baculoviral IAP repeat-containing protein 7 | Spondin-2 | WD repeat-containing protein 82 | Putative testis-specific prion protein |
| Calumenin | Testican-2 | Adipocyte enhancer-binding protein 1 | Proline-rich protein 1 |
| Alpha-S1-casein | Inactive serine protease PAMR1 | ADAMTS-like protein 3 | Putative uncharacterized protein FP248 |
| Cyclin-L1 | Torsin-2A | Coiled-coil domain-containing protein 80 | UPF0670 protein C8orf55 |
| Complement factor H | Vasohibin-1 | Ecto-NOX disulfide-thiol exchanger 1 | Putative zinc-alpha-2-glycoprotein-like 2 |
| Chorionic somatomammotropin hormone | Vasorin | Neuronal growth regulator 1 | SPARC protein |
| Coxsackievirus and adenovirus receptor | Xylosyltransferase 1 | Interphotoreceptor matrix proteoglycan 1 | Otopetrin-1 |
| Ectonucleotide pyrophosphatase/phosphodiesterase family member 6 | Ectonucleotide pyrophosphatase/phosphodiesterase family member 2 | cDNA FLJ36603 fis, clone TRACH2015180, highly similar to Secreted frizzled-related protein 2 | cDNA FLJ55667, highly similar to Secreted protein acidic and rich in cysteine |
| ERO1-like protein alpha | Oncostatin-M | Lipase member H | Lipase member K |
| Coagulation factor IX | Derlin-1 | Mucin-19 (MUC-19) | C-type lectin domain family 18 member C |

TABLE 1-continued

| | |
|---|---|
| Low affinity immunoglobulin gamma Fc region receptor III-B | HERV-FRD_6p24.1 provirus ancestral Env polyprotein |
| Ficolin-3 | Prostasin |
| Fc receptor-like protein 2 | Transmembrane protease, serine 11E |
| Leucine-rich repeat transmembrane protein 1 | HLA class I histocompatibility antigen, Cw-16 alpha chain |
| FLRT3 | Wnt inhibitory factor 1 |
| Gelsolin | C-type natriuretic peptide |
| Granulysin | Angiopoietin-2 |
| Transmembrane glycoprotein NMB | Deoxyribonuclease gamma |
| Granulins | Carboxypeptidase A5 |
| Heparanase | C-C motif chemokine 14 |
| Ig mu chain C region | Interleukin-5 |
| Interleukin-1 alpha | Interleukin-10 |
| Interleukin-31 receptor A | C—X—C motif chemokine 2 |
| Junctional adhesion molecule B | C—X—C motif chemokine 5 |
| Lipocalin-1 | A disintegrin and metalloproteinase with thrombospondin motifs 6 |
| Leucine-rich repeat-containing G-protein coupled receptor 6 | Polypeptide |
| Latent-transforming growth factor beta-binding protein 1 | N-acetylgalactosaminyltransferase 1 |
| Matrilin-3 | Fibulin-2 |
| Myelin protein zero-like protein 1 | Ficolin-1 |
| Neurobeachin-like protein 2 | SL cytokine |
| Nicastrin | Follistatin |
| ADP-ribose pyrophosphatase, mitochondrial | FRAS1-related extracellular matrix protein 1 |
| Protocadherin-15 | Enamelin |
| Placenta growth factor | Hyaluronan and proteoglycan link protein 1 |
| Protein O-linked-mannose beta-1,2-N-acetylglucosaminyltransferase 1 | Leukocyte immunoglobulin-like receptor subfamily A member 3 |
| Probable hydrolase PNKD | Interleukin-17F |
| Pleiotrophin | Interleukin-1 receptor accessory protein |
| Poliovirus receptor | Serine protease inhibitor Kazal-type 5 |
| Reticulon-4 receptor | Kallikrein-15 |
| Serum amyloid A protein | Interferon alpha-14 |
| Sex hormone-binding globulin | Pregnancy-specific beta-1-glycoprotein 4 |
| SLAM family member 6 | Collagenase 3 |
| Sarcolemmal membrane-associated protein | Matrix metalloproteinase-16 |
| Sushi, von Willebrand factor type A, EGF and pentraxin domain-containing protein 1 | Pituitary adenylate cyclase-activating polypeptide |
| Thyroxine-binding globulin | Prokineticin-2 |
| Transmembrane and coiled-coil domain-containing protein 1 | Latent-transforming growth factor beta-binding protein 3 |
| Transmembrane protease, serine 3 | Somatoliberin |
| Tumor necrosis factor receptor superfamily member 10C | Thrombospondin type-1 domain-containing protein 1 |
| Tumor necrosis factor receptor superfamily member 11B | Angiogenic factor with G patch and FHA domains 1 |
| Serotransferrin | TGF-beta receptor type III |
| Tryptase beta-2 | Thyrotropin subunit beta |
| Protein YIPF5 | Uncharacterized protein C19orf36 |
| Vesicle-associated membrane protein-associated protein B/C | Complement C1q tumor necrosis factor-related protein 2 |
| Psoriasis susceptibility 1 candidate gene 2 protein | Putative uncharacterized protein UNQ6125/PRO20090 |
| Integral membrane protein 2A | Complement C3 |
| Vesicle transport protein SFT2B | Collagen alpha-2(IV) chain |
| von Willebrand factor A domain-containing protein 3A | Uncharacterized protein UNQ6126/PRO20091 |
| Protein shisa-2 homolog | Serpin-like protein HMSD |
| Signal peptidase complex subunit 3 | Prostate and testis expressed protein 4 |
| CD164 sialomucin-like 2 protein | Collagen alpha-1(XXII) chain |
| Cadherin-16 | Putative uncharacterized protein C13orf28 |
| Cadherin-19 | Cystatin-S |
| Cerebellin-2 | R-spondin-1 |
| Transmembrane protein C3orf1 | C8orf2 |
| Sperm equatorial segment protein 1 | Odorant-binding protein 2a |
| Uncharacterized protein C6orf72 | Opiorphin |
| Uncharacterized protein C11orf24 | Kidney androgen-regulated protein |
| Acyl-CoA synthetase family member 2, mitochondrial | Putative uncharacterized protein UNQ5830/PRO19650/PRO19816 |
| Probable UDP-sugar transporter protein SLC35A5 | Putative uncharacterized protein UNQ6975/PRO21958 |
| C-type lectin domain family 1 member A | Tachykinin-3 |
| C-type lectin domain family 3 member A | Secreted phosphoprotein 1 |
| C-type lectin domain family 4 member E | Sclerostin |
| C-type lectin domain family 4 member G | ADAMTS-like protein 2 |
| Probable cation-transporting ATPase 13A4 | Scavenger receptor cysteine-rich domain-containing protein LOC284297 |
| UPF0480 protein C15orf24 | Tryptase beta-1 |
| Zona pellucida sperm-binding protein 4 | Tryptase delta |
| Endoplasmic reticulum resident protein ERp27 | Putative cat eye syndrome critical region protein 9 |
| Transmembrane protein C16orf54 | Plexin domain-containing protein 1 |
| Cytochrome P450 4F12 | MC51L-53L-54L homolog (Fragment) |
| Cytochrome P450 4X1 | COBW-like placental protein (Fragment) |
| Cytochrome P450 4Z1 | Cytokine receptor-like factor 2 |
| Protein CREG2 | Beta-defensin 103 |
| DnaJ homolog subfamily B member 9 | Beta-defensin 106 |
| Dipeptidase 3 | Hyaluronidase-3 |
| Membrane protein FAM174A | Interleukin-28 receptor alpha chain |
| Thioredoxin domain-containing protein 15 | Glycosyltransferase 54 domain-containing protein |
| Protein FAM19A4 | Chordin-like protein 1 |
| Adenosine monophosphate-protein transferase FICD | Putative uncharacterized protein UNQ9370/PRO34162 |
| Prenylcysteine oxidase-like | Netrin receptor UNC5B |
| Phytanoyl-CoA hydroxylase-interacting protein-like | Fibroblast growth factor receptor FGFR-1 secreted form protein (Fragment) |
| FXYD domain-containing ion transport regulator 4 | Uncharacterized protein ENSP00000244321 |
| Growth/differentiation factor 11 | ECE2 |
| Cerebral dopamine neurotrophic factor | EPA6 |
| GPN-loop GTPase 2 | Putative abhydrolase domain-containing protein FAM108A6 |
| Growth hormone-inducible transmembrane protein | |

TABLE 1-continued

| | | |
|---|---|---|
| cDNA, FLJ96669, highly similar to Homo sapiens secreted protein, acidic, cysteine-rich (osteonectin)(SPARC), mRNA | Ectonucleotide pyrophosphatase/phosphodiesterase family member 5 | Glycerophosphodiester phosphodiesterase domain-containing protein 2 | Putative V-set and immunoglobulin domain-containing-like protein ENSP00000030034 |
| cDNA FLJ77519, highly similar to Homo sapiens secreted frizzled related protein mRNA | Polypeptide N-acetylgalactosaminyltransferase-like protein 2 | WAP, kazal, immunoglobulin, kunitz and NTR domain-containing protein 1 | B cell maturation antigen transcript variant 4 (Tumor necrosis factor receptor superfamily member 17) |
| T-cell differentiation antigen CD6 | Slit homolog 1 protein | KDEL motif-containing protein 1 | UPF0672 protein C3orf58 |
| Pikachurin | Growth hormone variant | Adipophilin | Methylthioribose-1-phosphate isomerase |
| Fibrinogen-like protein 1 | Angiopoietin-related protein 3 | Lactase-like protein | 17-beta hydroxysteroid dehydrogenase 13 |
| Interleukin-32 | Angiopoietin-related protein 7 | Chondromodulin-1 | Aminopeptidase B |
| Matrilin-4 | Ecto-ADP-ribosyltransferase 5 | Collagen alpha-6(VI) chain | Dermcidin |
| Sperm-associated antigen 11B | Carbonic anhydrase-related protein 11 | Leucine-rich repeat-containing protein 33 | Meteorin |
| Coagulation factor XII | Probable ribonuclease 11 | MANSC domain-containing protein 1 | Methyltransferase-like protein 7A |
| Hepcidin | Probable carboxypeptidase X1 | Lipocalin-15 | NL3 |
| Klotho | Protein FAM3D | Arylsulfatase I | N-acetyltransferase 15 |
| Serglycin | C—X—C motif chemokine 14 | Mesoderm development candidate 2 | Ephrin-A4 |
| Tomoregulin-2 | Beta-defensin 127 | Dickkopf-related protein 1 | Protein Plunc |
| Chordin-like protein 2 | Beta-defensin 129 | Podocan | Kallikrein-11 |
| Tumor necrosis factor receptor superfamily member 6B | Cysteine-rich secretory protein LCCL domain-containing 2 | Fibronectin type III domain-containing protein 1 | WNT1 induced secreted protein 1 splice variant x (Fragment) |
| UPF0414 transmembrane protein C20orf30 | Fibroblast growth factor 21 | Neurotrimin | Interleukin-1 family member 10 |
| C-type lectin domain family 4 member C | Plasma alpha-L-fucosidase | Olfactory receptor 10W1 | PLA2G2D |
| UPF0317 protein C14orf159, mitochondrial | Gastrokine-1 | Protein PARM-1 | Proteoglycan 3 |
| Netrin-G2 | Gastrokine-2 | PDZ domain-containing protein 2 | Insulin-like peptide INSL5 |
| Metalloreductase STEAP2 | Glutathione peroxidase 7 | Proepiregulin | Olfactomedin-like protein 3 |
| Sushi domain-containing protein 4 | HHIP-like protein 1 | Polycystic kidney disease protein 1-like 1 | Extracellular glycoprotein lacritin |
| Protein YIF1B | Interferon kappa | WLPL514 | Retinol dehydrogenase 13 |
| Apolipoprotein M | Apolipoprotein C-I | Matrix metalloproteinase-26 | Neutrophil defensin 3 |
| C4b-binding protein beta chain | Procollagen C-endopeptidase enhancer 2 | REIT-like protein 2 | GLGQ3807 |
| T-cell surface glycoprotein CD8 beta chain | Left-right determination factor 1 | Solute carrier family 35 member E3 | TUFT1 |
| C-C motif chemokine 3-like 1 | Leucine-rich repeat LGI family member 4 | Zinc transporter ZIP9 | DRLY8200 |
| Fibroblast growth factor 8 | BRCA1-A complex subunit Abraxas | Noelin-2 | IDLW5808 |
| Sialomucin core protein 24 | Leucine zipper protein 2 | Seizure 6-like protein 2 | UBAP2 |
| Programmed cell death 1 ligand 2 | Secretoglobin family 3A member 1 | Semaphorin-3A | C1q/TNF-related protein 8 |
| Secreted and transmembrane 1 | Tsukushin | Semaphorin-4C | KIR2DL4 (Fragment) |
| Complement C1q tumor necrosis factor-related protein 6 | Osteomodulin | Abhydrolase domain-containing protein 14A | Chemokine-like factor super family 2 transcript variant 2 |
| EGF-like module-containing mucin-like hormone receptor-like 3 | Claudin-2 (SP82) | Ankyrin repeat domain-containing protein 36 | Keratinocytes associated transmembrane protein 1 |
| Noelin-3 | Complement factor H-related protein 2 | Protein shisa-4 | GKGM353 |
| Odorant-binding protein 2b | Kazal-type serine protease inhibitor domain-containing protein 1 | Neuromedin-U | MATL2963 |
| Urotensin-2 | Immunoglobulin superfamily containing leucine-rich repeat protein | Nodal homolog | NINP6167 |
| Vitrin | Sperm acrosome membrane-associated protein 3 | Synaptogyrin-2 | POM121-like |
| WNT1-inducible-signaling pathway protein 3 | Leucine-rich repeat and immunoglobulin-like domain-containing nogo receptor-interacting protein 1 | Brain-specific angiogenesis inhibitor 1-associated protein 2-like protein 2 | RTFV9368 (SLE-dependent upregulation 1) |
| cDNA FLJ75759, highly similar to Homo sapiens follistatin-like 3 (secreted glycoprotein) (FSTL3), mRNA | Kin of IRRE-like protein 3 | Coiled-coil domain-containing protein 104 | Leucine-rich repeat and immunoglobulin-like domain-containing nogo receptor-interacting protein 4 |
| Angiotensin-converting enzyme 2 | Hematopoietic cell signal transducer | Transmembrane 4 L6 family member 20 | KCNQ2 |
| Adiponectin | Follitropin subunit beta | Transmembrane protein 107 | ELCV5929 |
| Angiopoietin-related protein 4 | Melanoma inhibitory activity protein 3 | Transmembrane protein 143 | KVVM3106 |
| Apolipoprotein A-V | Leucine-rich repeat-containing protein 4 | Transmembrane protein 178 | ISPF6484 |
| Asporin | | Transmembrane protein 205 | LKHP9428 |

TABLE 1-continued

| Name | Name | Code |
|---|---|---|
| Bactericidal permeability-increasing protein | Zinc transporter 5 | Transmembrane protein 41A | VNFT9373 |
| CUB domain-containing protein 1 | Leucine-rich repeat neuronal protein 1 | Transmembrane protein 50A | ACAH3104 |
| Cartilage intermediate layer protein 1 | Apical endosomal glycoprotein | Transmembrane protein 50B | RVLA1944 |
| Beta-Ala-His dipeptidase | Serum amyloid A-4 protein | Interleukin-28B | Wpep3002 |
| Collagen alpha-1(V) chain | Probetacellulin | Neuronal pentraxin-2 | ZDHHC11 |
| Collagen alpha-1(XXV) chain | Beta-1,4-galactosyltransferase 7 | Collectrin | AGLW2560 |
| Estradiol 17-beta-dehydrogenase 11 | 3-hydroxybutyrate dehydrogenase type 2 | Transmembrane protein 92 | TSSP3028 |
| DnaJ homolog subfamily C member 10 | C1GALT1-specific chaperone 1 | Transmembrane protein 95 | RFVG5814 |
| EGF-like domain-containing protein 6 | Beta-casein | Transmembrane protein 9B | SHSS3124 |
| Coagulation factor XIII A chain | Kappa-casein | Probable carboxypeptidase PM20D1 | MMP19 |
| Glucose-6-phosphate isomerase | Transmembrane protein C2orf18 | Tetraspanin-12 | GSQS6193 |
| Appetite-regulating hormone | Carboxypeptidase N catalytic chain | Tetraspanin-13 | VGPW2523 |
| Interleukin-12 subunit beta | CD320 antigen | Tetraspanin-15 | LMNE6487 |
| Interleukin-22 | Chondroitin sulfate synthase 1 | UPF0513 transmembrane protein | ALLA2487 |
| Intelectin-1 | Chondroitin sulfate synthase 2 | Mitochondrial uncoupling protein 4 | GALI1870 |
| Leucine-rich glioma-inactivated protein 1 | CMRF35-like molecule 7 | Polyserase-2 | FRSS1829 |
| Lymphocyte antigen 96 | Protein canopy homolog 3 | Probable palmitoyltransferase ZDHHC24 | MRSS6228 |
| Matrilysin | Short-chain dehydrogenase/reductase 3 | Zona pellucida sperm-binding protein 1 | GRPR5811 |
| Mucin-20 | Delta-like protein 4 | Zona pellucida sperm-binding protein 2 | AVLL5809 |
| Proprotein convertase subtilisin/kexin type 9 | Delta and Notch-like epidermal growth factor-related receptor | Conserved oligomeric Golgi complex subunit 7 | CR1 C3b/C4b receptor SCR9 (or 16) C-term. exon SCR = short consensus repeat |
| Peptidoglycan recognition protein | Dolichol kinase | Adiponectin receptor protein 2 | PIKR2786 |
| Interferon-induced 17 kDa protein | Endothelin-converting enzyme-like 1 | Inhibin beta C chain | S100 calcium binding protein A7-like 3 |
| Protein Wnt-4 | Integral membrane protein 2B | Brorin | GTWW5826 (LP5085 protein) |
| Allograft inflammatory factor 1-like | Insulin-like growth factor-binding protein 5 | Semaphorin-3C | KTIS8219 (HCG202043) |
| Armadillo repeat-containing X-linked protein 3 | Endothelial cell-selective adhesion molecule | Heparan sulfate glucosamine 3-O-sulfotransferase 2 | Hyaluronan and proteoglycan link protein 4 |
| Chondroitin sulfate N-acetylgalactosaminyltransferase 1 | Signal peptide, CUB and EGF-like domain-containing protein 1 | Leptin receptor overlapping transcript-like 1 | Micronovel |
| Chitotriosidase-1 | Complement factor H-related protein 3 | SPARC-like protein 1 | SAMK3000 |
| Claudin domain-containing protein 1 | Prorelaxin H1 | Fibulin-7 | VFLL3057 |
| Erlin-2 | Follistatin-related protein 1 | Protein HEG homolog 1 | CVWG5837 |
| Glycosyltransferase 8 domain-containing protein 1 | Globoside alpha-1,3-N-acetylgalactosaminyltransferase 1 | Fibrinogen C domain-containing protein 1 | VGSA5840 |
| Golgi membrane protein 1 | Gamma-glutamyl hydrolase | Phospholipase A1 member A | GHPS3125 |
| Probable G-protein coupled receptor 125 | Cadherin-24 | Basic salivary proline-rich protein 2 | GRTR3118 |
| Interleukin-20 receptor alpha chain | Glycerol-3-phosphate acyltransferase 3 | Spermatogenesis-associated protein 6 | PAMP6501 |
| Galectin-7 | G-protein coupled receptor 56 | Sushi repeat-containing protein SRPX2 | LTLL9335 |
| NKG2D ligand 4 | Hyaluronan-binding protein 2 | Twisted gastrulation protein homolog 1 | VCEW9374 |
| L-amino-acid oxidase | Proheparin-binding EGF-like growth factor | Torsin-1B | AHPA9419 |
| Prolyl 3-hydroxylase 1 | Histidine-rich glycoprotein | Protein Wnt-5a | MDHV1887 |
| GPI ethanolamine phosphate transferase 2 | Carbohydrate sulfotransferase 14 | Acrosin-binding protein | HSAL5836 |
| GPI ethanolamine phosphate transferase 3 | Interleukin-20 receptor beta chain | C-type lectin domain family 18 member B | LHLC1946 |
| Calcium-binding mitochondrial carrier protein SCaMC-2 (Small calcium-binding mitochondrial carrier protein 2) | Ectonucleotide pyrophosphatase/phosphodiesterase family member 3 | Lysosomal-associated transmembrane protein 4A | Long palate, lung and nasal epithelium carcinoma-associated protein 3 (Ligand-binding protein RYA3) |
| Pulmonary surfactant-associated protein A2 | Insulin-like growth factor-binding protein 7 | Semaphorin-3E | LPPA601 |
| Splicing factor, arginine/serine-rich 16 | Kallistatin | Ameloblastin | PINK1 |
| Alpha-N-acetylgalactosaminide alpha-2,6-sialyltransferase 6 | Fibronectin type III domain-containing protein 3B | Major facilitator superfamily domain-containing protein 5 | SERH2790 |
| Single Ig IL-1-related receptor | Leukemia inhibitory factor receptor | Angiopoietin-1 | FLFF9364 |
| Tectonic-3 | Lin-7 homolog B | Angiopoietin-4 | APELIN |
| Tumor necrosis factor ligand superfamily | Thioredoxin-related transmembrane | Multiple epidermal growth factor-like | GLSH6409 |

TABLE 1-continued

| | | |
|---|---|---|
| member 11 | protein 1 | domains 9 |
| Tumor necrosis factor receptor superfamily member 19 | Disintegrin and metalloproteinase domain-containing protein 32 | Acid sphingomyelinase-like phosphodiesterase 3a | SFVP2550 |
| Palmitoyltransferase ZDHHC9 | Ly6/PLAUR domain-containing protein 3 | ADAMTS-like protein 5 | RRLF9220 |
| Fibulin-5 | C-type lectin domain family 14 member A | Spexin | PTML5838 |
| Protein Z-dependent protease inhibitor | Protein cornichon homolog | Putative trypsin-6 | VLGN1945 |
| Alpha-2-macroglobulin | Protein FAM151A | Proto-oncogene protein Wnt-1 | AVPC1948 |
| Agouti-related protein | FK506-binding protein 14 | Bone morphogenetic protein 3b | AWQG2491 |
| Pancreatic alpha-amylase | Neuropilin and tolloid-like protein 2 | Bone morphogenetic protein 5 | PSVL6168 |
| Natriuretic peptides B | Protocadherin beta-13 | Bone morphogenetic protein 8B | LCII3035 |
| Atrial natriuretic factor | Prenylcysteine oxidase 1 | Protein FAM26D | PPRR6495 |
| Neutral ceramidase | Peflin | C1q-related factor | RLSC6348 |
| Beta-2-microglobulin | Peptidyl-prolyl cis-trans isomerase-like 1 | WAP four-disulfide core domain protein 1 | CSRP2BP |
| Bone morphogenetic protein 4 | Prostate stem cell antigen | Cerebellin-1 | GLLV3061 |
| Biotinidase | Protein patched homolog 2 | Carboxypeptidase O | GWSI6489 |
| Scavenger receptor cysteine-rich type 1 protein M130 | Chitobiosyldiphosphodolichol beta-mannosyltransferase | Myelin protein zero-like protein 2 (Epithelial V-like antigen 1) | cDNA FLJ53955, highly similar to Secreted frizzled-related protein 4 |
| Carboxypeptidase B2 | Protein sel-1 homolog 1 | Serine protease 1-like protein 1 | PPIF |
| Carboxypeptidase Z | ProSAAS | Coiled-coil domain-containing protein 70 | VSSW1971 |
| C-C motif chemokine 5 | Sialic acid-binding Ig-like lectin 9 | C-C motif chemokine 28 | KLIA6249 |
| C-C motif chemokine 7 | SLIT and NTRK-like protein 1 | Uncharacterized protein C4orf29 | ALLW1950 |
| C-C motif chemokine 8 | Statherin | CUB domain-containing protein 2 | GVEI466 |
| CD59 glycoprotein | Testisin | Trem-like transcript 4 protein | ESFI5812 |
| Complement factor I | Transmembrane channel-like protein 5 | Uncharacterized protein C6orf58 | GNNC2999 |
| Clusterin | Transmembrane protease, serine 4 | Chondroadherin | AAGG6488 |
| Collagen alpha-2(I) chain | Metastasis-suppressor KiSS-1 | Cartilage intermediate layer protein 2 | HHSL751 |
| Collagen alpha-1(III) chain | Islet amyloid polypeptide | Uncharacterized protein C10orf25 | Beta-defensin 108B |
| Collagen alpha-1(IV) chain | Trem-like transcript 2 protein | Isthmin-1 | Beta-defensin 118 |
| Collagen alpha-3(IV) chain | Thioredoxin domain-containing protein 12 | Cystatin-8 | Beta-defensin 124 |
| Collagen alpha-5(IV) chain | Vascular endothelial growth factor B | Cardiotrophin-1 (CT-1) | Beta-defensin 125 |
| Collagen alpha-3(VI) chain | Vascular endothelial growth factor C | Chymotrypsinogen B | Beta-defensin 126 |
| Complement component C6 | Reticulocalbin-3 | C—X—C motif chemokine 9 | Deoxyribonuclease-1-like 2 |
| Collagen alpha-1(IX) chain | Fibrillin-1 | C—X—C motif chemokine 13 | Stanniocalcin-2 |
| Collagen alpha-1(X) chain | Protein FAM3A | EMILIN-3 | Endothelial cell-specific molecule 1 |
| Collagen alpha-1(XVII) chain | Protein G7c | Secretagogin | Carboxylesterase 7 |
| Collagen alpha-1(XXI) chain | Neuropilin and tolloid-like protein 1 | Epididymal secretory protein E3-alpha | Protein NOV homolog |
| Coatomer subunit alpha | Pregnancy-specific beta-1-glycoprotein 11 | Epiphycan | UPF0528 protein FAM172A |
| Complement receptor type 1 | Serpin B4 | Protein FAM5C | Interleukin-27 subunit beta |
| Cystatin-SN | ADAM DEC1 | Fibroblast growth factor 20 | Protein FAM3C |
| Deoxyribonuclease-1 | ADP-dependent glucokinase | Fibroblast growth factor-binding protein 3 | Stromal cell-derived factor 2-like protein 1 |
| Extracellular matrix protein 1 | Alpha-amylase 2B | Transmembrane protein 204 | Butyrophilin subfamily 1 member A1 |
| Glial cell line-derived neurotrophic factor | UDP-GlcNAc:betaGal beta-1,3-N-acetylglucosaminyltransferase 3 | Phosphatidylethanolamine-binding protein 4 | Keratinocyte-associated transmembrane protein 2 |
| Insulin-like growth factor-binding protein 3 | Calcitonin gene-related peptide 2 | Coagulation factor V | Immunoglobulin alpha Fc receptor |
| Insulin-like growth factor IA | Carboxypeptidase E | Coagulation factor VII | EMILIN-2 |
| Fc region receptor III-A | Cardiotrophin-like cytokine factor 1 | Pro-MCH | Ephrin type-A receptor 10 |
| Alpha-fetoprotein | Collagen alpha-2(VIII) chain | Folate receptor gamma | Exostosin-like 2 |
| Heparin-binding growth factor 2 | Crumbs homolog 2 | Mucin-7 | Follistatin-related protein 4 |
| Fibrinogen gamma chain | Dentin matrix acidic phosphoprotein 1 | Galanin-like peptide | Follistatin-related protein 5 |
| Growth/differentiation factor 5 | Down syndrome cell adhesion molecule | Hemicentin-1 | Transmembrane protein 66 |
| Ig gamma-1 chain C region | Immunoglobulin superfamily member 1 | Interleukin-6 | Growth/differentiation factor 2 |
| Ig gamma-2 chain C region | Interleukin-4 | Embryonic growth/differentiation factor 1 | GDNF family receptor alpha-4 |
| Ig gamma-3 chain C region | Interleukin-6 receptor subunit alpha | Interleukin-8 | Ig gamma-4 chain C region |

TABLE 1-continued

| | | |
|---|---|---|
| Insulin-like 3 | Interleukin-24 | Lymphocyte antigen 86 |
| Inter-alpha-trypsin inhibitor heavy chain | Ladinin-1 | Inhibin beta E chain |
| UPF0378 protein KIAA0100 | Lipase member I | GRAM domain-containing protein 1C |
| Kininogen-1 | Pancreatic lipase-related protein 1 | Interferon alpha-10 |
| Laminin subunit alpha-2 | Leucine-rich alpha-2-glycoprotein | Interferon alpha-16 |
| Laminin subunit alpha-4 | Matrix-remodeling-associated protein 5 | Interferon alpha-6 |
| Protein-lysine 6-oxidase | Netrin-4 | Immunoglobulin superfamily member 21 |
| Multimerin-1 | Hepatocyte growth factor receptor | Agrin |
| Vasopressin-neurophysin 2-copeptin | C-C motif chemokine 22 | Prolactin |
| Nidogen-1 | Nyctalopin | Kelch-like protein 11 |
| Phospholipase A2, | Osteocalcin | Protein Wnt-16 |
| Perforin-1 | Basic salivary proline-rich protein 3 | Properdin |
| Phosphatidylinositol-glycan-specific phospholipase D | Pregnancy-specific beta-1-glycoprotein 10 | Kallikrein-13 |
| Fibrocystin | Leucine-rich repeat transmembrane protein FLRT2 | 1-acyl-sn-glycerol-3-phosphate acyltransferase delta |
| Phospholipid transfer protein | R-spondin-3 | Kallikrein-9 |
| Prostatic acid phosphatase | Sialoadhesin | Vitamin K-dependent protein S |
| Vitamin K-dependent protein Z | Trypsin-3 | Butyrophilin-like protein 8 |
| Salivary acidic proline-rich phosphoprotein 1/2 | Dipeptidase 2 | Laminin subunit beta-4 |
| Pregnancy zone protein | Collagen and calcium-binding EGF domain-containing protein 1 | Lymphatic vessel endothelial hyaluronic acid receptor 1 |
| Prorelaxin H2 | Germ cell-specific gene 1-like protein | Cystatin-SA |
| Semaphorin-4D | Leucine-rich repeat-containing protein 31 | Transmembrane protein 59 |
| Slit homolog 2 protein | Apolipoprotein O | Apolipoprotein(a)-like protein 2 |
| Alpha-tectorin | Dystroglycan | Lysozyme-like protein 2 |
| Tenascin-X | Neutrophil defensin 4 | Lysozyme-like protein 4 |
| Trefoil factor 3 | Amphoterin-induced protein 3 | Reelin |
| Transferrin receptor protein 1 | Gamma-secretase subunit APH-1B | Retinol-binding protein 4 |
| Protransforming growth factor alpha | Apolipoprotein C-IV | Carbonic anhydrase 14 |
| Transforming growth factor beta-2 | Arylsulfatase G | Tubulointerstitial nephritis antigen |
| Tumor necrosis factor ligand superfamily member 6 | Glia-activating factor | Neuropeptide W |
| | Caspase recruitment domain-containing protein 18 | Alpha-1,3-mannosyl-glycoprotein 4-beta-N-acetylglucosaminyltransferase B |
| Tumor necrosis factor receptor superfamily member 1B | Heparan sulfate glucosamine 3-O-sulfotransferase 3A1 | Transmembrane emp24 domain-containing protein 5 |
| Tumor necrosis factor receptor superfamily member 5 | Thyrotropin-releasing hormone-degrading ectoenzyme | Complement C1q tumor necrosis factor-related protein 3 |
| Thrombopoietin | Guanylin | Podocan-like protein 1 |
| VIP peptides | Choline transporter-like protein 3 | Pregnancy-specific beta-1-glycoprotein 5 |
| Acidic mammalian chitinase | 17-beta-hydroxysteroid dehydrogenase 14 | Keratocan |
| Cysteine-rich secretory protein 2 | Immunoglobulin lambda-like polypeptide 1 | Group IIE secretory phospholipase A2 |
| Haptoglobin-related protein | DnaJ homolog subfamily B member 14 | Left-right determination factor 2 |
| C-C motif chemokine 26 | F-box only protein 8 | NKG2D ligand 2 |
| Collectin-11 | Fibroleukin | Macrophage metalloelastase |
| Cysteine-rich with EGF-like domain protein 2 | Methionine-R-sulfoxide reductase B3, mitochondrial | Triggering receptor expressed on myeloid cells 1 |
| C—X—C motif chemokine 16 | Leucine-rich repeat LGI family member 2 | Cytokine receptor-like factor 1 |
| Fibroblast growth factor-binding protein 1 | Vesicle transport protein GOT1B | Secretin |
| Interleukin-1 family member 5 | Integral membrane protein GPR177 | Stromal cell-derived factor 2 |
| Interleukin-1 family member 9 | Probable G-protein coupled receptor 78 | Lysozyme-like protein 6 |
| Kallikrein-5 | HEPACAM family member 2 | Serpin A9 |
| Matrilin-2 | Interleukin-27 receptor subunit alpha | Sclerostin domain-containing protein 1 |
| Cell surface glycoprotein CD200 receptor 1 | Proenkephalin-A | Lysocardiolipin acyltransferase 1 |
| | Gremlin-2 | |
| | Stromelysin-2 | |
| | Probable G-protein coupled receptor 171 | |
| | Pappalysin-2 | |
| | Microfibril-associated glycoprotein 4 | |
| | Neuromedin-B | |
| | Mimecan | |
| | Matrix metalloproteinase-19 | |
| | Interleukin-11 | |
| | Interleukin-17A | |
| | Interleukin-18 | |
| | Interleukin-26 | |
| | Interleukin-28A | |
| | Transmembrane emp24 domain-containing protein 3 | |
| | Interleukin-29 | |
| | Insulin-like peptide INSL6 | |
| | Protein Wnt-2b | |
| | Pregnancy-specific beta-1-glycoprotein 1 | |
| | Sperm acrosome membrane-associated protein 4 | |
| | Laminin subunit gamma-3 | |
| | Lysyl oxidase homolog 3 | |
| | Neurotensin/neuromedin N | |
| | MAM domain-containing protein 2 | |
| | Microfibrillar-associated protein 2 | |
| | Melanoma inhibitory activity protein 2 | |
| | Matrix metalloproteinase-24 | |
| | Matrix metalloproteinase-25 | |
| | Netrin-1 | |
| | Netrin-3 | |
| | Alpha-N-acetylgalactosaminide alpha-2,6-sialyltransferase 1 | |
| | Alpha-N-acetylgalactosaminide alpha-2,6-sialyltransferase 3 | |
| | Melanoma-derived growth regulatory protein | |
| | FMRFamide-related peptides | |
| | Otoconin-90 | |
| | Neurturin | |
| | Neurexophilin-1 | |
| | Neurexophilin-2 | |
| | Platelet factor 4 variant | |
| | Nociceptin | |
| | V-set and transmembrane domain-containing protein 1 | |
| | Proline-rich protein 4 | |
| | Prolactin-releasing peptide | |
| | Serine protease 33 | |
| | Pregnancy-specific beta-1-glycoprotein 8 | |
| | Retbindin | |
| | FMRFamide-related peptides | |
| | Ribonuclease K6 | |

TABLE 1-continued

| | | | |
|---|---|---|---|
| Lysophosphatidic acid phosphatase type 6 | Integrin alpha-10 | Ribonuclease T2 | Plasma glutamate carboxypeptidase |
| Nucleotide exchange factor SIL1 | KTEL motif-containing protein 1 | Repetin | Slit homolog 3 protein |
| Thrombospondin type-1 domain-containing protein 4 | Leukocyte immunoglobulin-like receptor subfamily A member 5 | Complement C1r subcomponent-like protein | C3 and PZP-like alpha-2-macroglobulin domain-containing protein 8 |
| WNT1-inducible-signaling pathway protein 2 | Leucine-rich repeat and fibronectin type-III domain-containing protein 3 | Uncharacterized glycosyltransferase AER61 | Retinoic acid receptor responder protein 2 |
| Bromodomain-containing protein 9 | Uteroglobin | Semaphorin-3G | Cartilage acidic protein 1 |
| CD99 antigen-like protein 2 | Netrin-G1 ligand | Secretoglobin family 1C member 1 | Stanniocalcin-1 |
| Uncharacterized protein C1orf159 | Pannexin-1 | Secretoglobin family 1D member 1 | Beta-tectorin |
| Carbohydrate sulfotransferase 12 | Protocadherin-12 | Secretoglobin family 1D member 2 | Post-GPI attachment to proteins factor 3 |
| Probable serine carboxypeptidase CPVL | Protocadherin alpha-10 | Serpin A12 | Germ cell-specific gene 1 protein |
| Mucin-3A | Protocadherin beta-10 | Serpin I2 | Interleukin-21 receptor |
| CUB and zona pellucida-like domain-containing protein 1 | Osteopetrosis-associated transmembrane protein 1 | von Willebrand factor C and EGF domain-containing protein | V-set and immunoglobulin domain-containing protein 4 |
| Polypeptide N-acetylgalactosaminyltransferase 14 | Beta-galactoside alpha-2,6-sialyltransferase 1 | A disintegrin and metalloproteinase with thrombospondin motifs 15 | Scavenger receptor cysteine-rich domain-containing group B protein |
| Galectin-9 | GPI transamidase component PIG-S | Sodium channel subunit beta-2 | Prohyroliberin |
| Leucine-rich repeat-containing protein 17 | Proline-rich transmembrane protein 3 | Metalloproteinase inhibitor 4 | Semaphorin-4A |
| Leucine-rich repeat neuronal protein 2 | Sulfhydryl oxidase 2 | T-cell immunomodulatory protein | |
| Bifunctional heparan sulfate N-deacetylase/N-sulfotransferase 3 | A disintegrin and metalloproteinase with thrombospondin motifs 16 | A disintegrin and metalloproteinase with thrombospondin motifs 10 | Tumor necrosis factor receptor superfamily member 27 |
| Tuftelin | SH2 domain-containing protein 3A | Thymic stromal lymphopoietin | Toll-like receptor 7 |
| Brain mitochondrial carrier protein | SHC-transforming protein 4 | Transmembrane protein 130 | |
| Signal peptide, CUB and EGF-like domain-containing protein 3 | Disintegrin and metalloproteinase domain-containing protein 23 | Unique cartilage matrix-associated protein | Thioredoxin domain-containing protein 16 |
| 14-3-3 protein sigma | Transducin beta-like protein 2 | Urocortin-2 | Alpha-2-antiplasmin |
| Alpha-1-acid glycoprotein 1 | Tudor domain-containing protein 10 | Urocortin-3 ( | WAP four-disulfide core domain protein 3 |
| Alpha-1-acid glycoprotein 2 | Transmembrane 9 superfamily member 3 | Protein AMBP | Protein WFDC9 |
| von Willebrand factor A domain-containing protein 1 | Von Willebrand factor D and EGF domain-containing protein | Complement C1q tumor necrosis factor-related protein 9-like | A disintegrin and metalloproteinase with thrombospondin motifs 14 |
| Disintegrin and metalloproteinase domain-containing protein 9 | A disintegrin and metalloproteinase with thrombospondin motifs 17 | Growth inhibition and differentiation-related protein 88 | Adipocyte plasma membrane-associated protein |
| Angiotensinogen | Transmembrane channel-like protein 2 | Protein Wnt-10a | Peroxidasin homolog |
| Apolipoprotein A-II (Apo-AII) (ApoA-II) | Pregnancy-specific beta-1-glycoprotein 3 | Protein Wnt-3a | Progressive ankylosis protein homolog |
| Apolipoprotein A-IV (Apo-AIV) (ApoA-IV) | Tenomodulin | Proto-oncogene protein Wnt-3 | Chitinase-3-like protein 1 |
| Apolipoprotein C-II (ApoC-II) (ApoC-II) | Tetraspanin-6 | Protein Wnt-9a | UPF0672 protein CXorf36 |
| Beta-2-glycoprotein 1 | Thioredoxin domain-containing protein 5 | Protein Wnt-9a | Arylsulfatase J |
| Apoptosis-related protein 3 | Vascular endothelial growth factor D | Cytokine SCM-1 beta | Cortistatin |
| Beta-secretase 2 | Pregnancy-specific beta-1-glycoprotein 9 | Zymogen granule membrane protein 16 | Ceruloplasmin |
| Histo-blood group ABO system transferase | Semaphorin-3F | Zona pellucida-binding protein 1 | Angiopoietin-related protein 5 |
| Cathepsin L2 | Acid phosphatase-like protein 2 | Anterior gradient protein 3 homolog | Coiled-coil domain-containing protein 126 |
| C-C motif chemokine 3 | Apolipoprotein O-like | Amelotin | CD177 antigen |
| C-type lectin domain family 1 member B | Beta-defensin 119 | Uncharacterized protein C5orf46 | Protein canopy homolog 4 |
| Calcium-activated chloride channel regulator 1 | A disintegrin and metalloproteinase with thrombospondin motifs 12 | Uncharacterized aarF domain-containing protein kinase 1 | Fibronectin type-III domain-containing protein C4orf31 |
| Chymase | Protein FAM131A | Draxin | Protein FAM180A |
| Collagen alpha-1(VI) chain | Protein FAM3B | Fibroblast growth factor 18 | Platelet basic protein |
| Complement component C8 alpha chain | Beta-galactosidase-1-like protein | C—X—C motif chemokine 11 | Interferon epsilon |
| Complement component C9 | Lysozyme g-like protein 1 | Ly6/PLAUR domain-containing protein 6 | Intelectin-2 |

TABLE 1-continued

| | | |
|---|---|---|
| Glucose-fructose oxidoreductase domain-containing protein 2 | Inter-alpha-trypsin inhibitor heavy chain H5-like protein | Chymotrypsin-like elastase family member 1 |
| DnaJ homolog subfamily B member 11 | Sperm acrosome-associated protein 5 | Erythropoietin receptor |
| Ectonucleotide pyrophosphatase/phosphodiesterase family member 7 | Leucine-rich repeat and immunoglobulin-like domain-containing nogo receptor-interacting protein 2 | MAM domain-containing glycosylphosphatidylinositol anchor protein 2 |
| Endoplasmic reticulum aminopeptidase 1 | Surfactant-associated protein 2 | Matrix metalloproteinase-27 |
| Receptor tyrosine-protein kinase erbB-3 | Adiponectin receptor protein 1 | Inactive serine protease 35 |
| Endoplasmic reticulum resident protein ERp44 | Multiple epidermal growth factor-like domains 6 | Coiled-coil domain-containing protein 134 |
| IgGFc-binding protein | Neuroendocrine protein 7B2 | Suprabasin |
| Complement factor H-related protein 1 | Alpha-1B-glycoprotein | Secretoglobin family 1D member 4 |
| Polypeptide N-acetylgalactosaminyltransferase 2 | WAP, kazal, immunoglobulin, kunitz and NTR domain-containing protein 2 | V-set and transmembrane domain-containing protein 2A |
| Hemopexin | Arylacetamide deacetylase-like 1 | ADM |
| Hepatocyte growth factor activator | Histatin-3 | Uncharacterized protein C2orf82 |
| Major histocompatibility complex class I-related gene protein | Pro-neuregulin-3, membrane-bound isoform | Insulin growth factor-like family member 1 |
| Insulin-like growth factor-binding protein 6 | Agouti-signaling protein | Cadherin-like protein 29 |
| Ig delta chain C region | Claudin-8 | Bone morphogenetic protein 15 |
| Interleukin-1 beta | UPF0454 protein C12orf49 | Plasma serine protease inhibitor |
| Low-density lipoprotein receptor-related protein 10 | von Willebrand factor A domain-containing protein 5B1 | Carcinoembryonic antigen-related cell adhesion molecule 21 |
| Junctional adhesion molecule C | Cadherin-6 | Alpha-lactalbumin |
| Uncharacterized protein KIAA0319 | Cathelicidin antimicrobial peptide | Sister chromatid cohesion protein DCC1 |
| Laminin subunit alpha-5 | Carboxypeptidase N subunit 2 | Galectin-3-binding protein |
| Fibronectin type III domain-containing protein 4 | Dehydrogenase/reductase SDR family member 7B | Dynein heavy chain domain-containing protein 1 |
| Lipoprotein lipase | C-C motif chemokine 16 | C-C motif chemokine 17 |
| Interstitial collagenase | C-C motif chemokine 24 | Fatty acyl-CoA reductase 1 |
| Matrix metalloproteinase-9 | HEAT repeat-containing protein C7orf27 | Fin bud initiation factor homolog |
| Mucin-16 | Collagen alpha-2(IX) chain | Polymeric immunoglobulin receptor |
| Mucin-2 | Collagen alpha-3(IX) chain | Prion-like protein doppel |
| Mucin-5B | Colipase | C—X—C motif chemokine 6 |
| Myocilin | Collagen alpha-1(XXVII) chain | C—X—C motif chemokine 10 |
| Oxidized low-density lipoprotein receptor 1 | Carboxypeptidase N subunit 2 | Beta-defensin 1 |
| Prostate tumor overexpressed gene 1 protein | Leucine-rich repeat transmembrane neuronal protein 4 | Hyaluronan and proteoglycan link protein 2 |
| Receptor-interacting serine/threonine-protein kinase 2 | Collagen triple helix repeat-containing protein 1 | Disintegrin and metalloproteinase domain-containing protein 30 |
| Equilibrative nucleoside transporter 3 | Endothelin-2 | Suppressor of fused homolog |
| Selenoprotein P | Fibromodulin | Folate receptor beta |
| Pulmonary surfactant-associated protein D | Fc receptor-like B | Extracellular sulfatase Sulf-2 |
| Stimulated by retinoic acid gene 6 protein homolog | Zinc finger RAD18 domain-containing protein C1orf124 | Tumor necrosis factor receptor superfamily member 14 |
| Trefoil factor 1 | Growth/differentiation factor 15 | Artemin |
| Tissue factor pathway inhibitor 2 | Glia-derived nexin | Collagen alpha-1(XII) chain |
| Prothrombin | Progonadoliberin-1 | Collagen alpha-1(XIV) chain |
| Toll-like receptor 9 | Granzyme K | Beta-defensin 2 |
| Alpha-1,3-mannosyl-glycoprotein 4-beta-N-acetylglucosaminyltransferase A | | |
| Matrix extracellular phosphoglycoprotein | | |
| cDNA FLJ77863, highly similar to *Homo sapiens* secreted and transmembrane 1 (SECTM1), mRNA | | |
| Epididymal-specific lipocalin-6 | | |
| Afamin | | |
| Probable cation-transporting ATPase 13A5 | | |
| Glutathione peroxidase 3 | | |
| Claudin-18 | | |
| Putative killer cell immunoglobulin-like receptor like protein KIR3DP1 | | |
| Secretory phospholipase A2 receptor | | |
| Haptoglobin | | |
| Carcinoembryonic antigen-related cell adhesion molecule 20 | | |
| Bone morphogenetic protein 3 | | |
| Bone marrow stromal antigen 2 | | |
| Cytochrome P450 20A1 | | |
| Bactericidal/permeability-increasing protein-like 3 | | |
| Protein dpy-19 homolog 2 | | |
| Group IIF secretory phospholipase A2 | | |
| Carboxypeptidase B | | |
| Glycosyltransferase 8 domain-containing protein 2 | | |
| Protein FAM19A1 | | |
| GDNF family receptor alpha-like | | |
| Probable glutathione peroxidase 8 | | |
| Cystatin-D | | |
| Cystatin-F | | |
| Platelet-activating factor acetylhydrolase | | |
| Pappalysin-1 | | |
| Solute carrier family 22 member 12 | | |
| Choriogonadotropin hormone-like 1 | | |
| Regulator of microtubule dynamics protein 3 | | |
| Retinol dehydrogenase 14 | | |
| Galanin | | |
| Transcobalamin-2 | | |
| Catechol-O-methyltransferase domain-containing protein 1 | | |
| Tripeptidyl-peptidase 1 | | |
| Trem-like transcript 1 protein | | |
| Guanylate cyclase activator 2B | | |
| Inducible T-cell costimulator | | |

TABLE 1-continued

| | |
|---|---|
| Intercellular adhesion molecule 4 | Interleukin-21 |
| Interleukin-19 | Interleukin-3 |
| Isthmin-2 | Interleukin-7 |
| Kin of IRRE-like protein 1 | Inhibin alpha chain |
| Kallikrein-10 | Laminin subunit alpha-3 |
| Interferon alpha-17 | Notch homolog 2 N-terminal-like protein |
| Interferon alpha-21 | Laminin subunit beta-2 |
| Interferon alpha-8 | Neuropilin-2 |
| Interferon omega-1 | EGF-containing fibulin-like extracellular matrix protein 1 |
| Early placenta insulin-like peptide | Receptor-type tyrosine-protein phosphatase kappa |
| Latent-transforming growth factor beta-binding protein 4 | Dehydrogenase/reductase SDR family member on chromosome X |
| EGF, latrophilin and seven transmembrane domain-containing protein 1 | Regenerating islet-derived protein 4 |
| Paired immunoglobulin-like type 2 receptor alpha | FXYD domain-containing ion transport regulator 6 |
| Fibronectin type 3 and ankyrin repeat domains protein 1 | Tachykinin-4 |
| Regenerating islet-derived protein 3 alpha | Serine incorporator 2 |
| E3 ubiquitin-protein ligase RNF5 | Stromelysin-3 |
| Lysyl oxidase homolog 4 | Matrix metalloproteinase-23 |
| Protachykinin-1 | Secreted phosphoprotein 1 |
| Lumican | Complement C1q tumor necrosis factor-related protein 5 |
| Secreted frizzled-related protein 1, isoform CRA_a | Adropin |
| Plasminogen-related protein B | Leucine-rich repeat transmembrane protein FLRT1 |
| Probable palmitoyltransferase ZDHHC16 | Nucleobindin-2 |
| Angiopoietin-related protein 1 | Galectin-3 |
| UPF0510 protein C19orf63 | Opticin |
| Scavenger receptor cysteine-rich type 1 protein M160 | Phospholipase A2 |
| ER degradation-enhancing alpha-mannosidase-like 2 | Proenkephalin-B |
| Beta-galactosidase-1-like protein 2 | Pancreatic prohormone |
| Interleukin-17 receptor E | Pregnancy-specific beta-1-glycoprotein 6 |
| Interleukin-20 | Peptidoglycan recognition protein 1-beta |
| Interleukin-25 | Pre-small/secreted glycoprotein |
| PDZ domain-containing protein 11 | Pentraxin-related protein PTX3 |
| Relaxin-3 | Dickkopf-related protein 3 |
| Retinoid-inducible serine carboxypeptidase | Carboxylesterase 8 |
| Short palate, lung and nasal epithelium carcinoma-associated protein 2 | Immunoglobulin superfamily containing leucine-rich repeat protein 2 |
| WAP four-disulfide core domain protein 5 | V-set and immunoglobulin domain-containing protein 2 |
| Platelet-derived growth factor C | Thioredoxin-related transmembrane protein 4 |
| Disintegrin and metalloproteinase domain-containing protein 33 | Peptide YY |
| BSD domain-containing protein 1 | Retinol-binding protein 3 |
| Cell adhesion molecule 3 | Major facilitator superfamily domain-containing protein 2 |
| CDC45-related protein | Atherin |
| Chondrolectin | Translocation protein SEC63 homolog |
| Diacylglycerol O-acyltransferase 2 | Transforming growth factor beta-3 |
| 3-keto-steroid reductase | Protein Wnt-10b |
| Interleukin-17 receptor C | Renalase |
| Interleukin-17 receptor D | Proprotein convertase subtilisin/kexin type 4 |
| Integrator complex subunit 1 | Kallikrein-12 |
| Junctional adhesion molecule-like | Carboxypeptidase A4 |
| E3 ubiquitin-protein ligase LNX | Olfactomedin-4 |
| Leucine-rich repeat transmembrane neuronal protein 3 | Insulin-like growth factor-binding protein complex acid labile chain |
| Methionine adenosyltransferase 2 | Amelogenin, Y isoform |
| | Brevican core protein |
| | Porimin |
| | Torsin-1A |
| | Arylsulfatase F |
| | C-C motif chemokine 23 |
| | Choriogonadotropin subunit beta variant 2 |
| | Testican-3 |
| | Beta-defensin 104 |
| | Basic salivary proline-rich protein 4 |
| | Beta-defensin 105 |
| | Tumor necrosis factor receptor superfamily member 18 |
| | Beta-defensin 107 |
| | Brother of CDO |
| | Protein WFDC11 |
| | Beta-1,4-galactosyltransferase 4 |
| | WAP four-disulfide core domain protein 6 |
| | Dehydrogenase/reductase SDR family member 9 |
| | Epigen |
| | Eppin |
| | Protein FAM19A5 |
| | Otoancorin |
| | Claudin-6 |
| | Tenascin-R |
| | Carcinoembryonic antigen-related cell adhesion molecule 19 | Growth factor |
| | Fibroblast growth factor receptor-like 1 |
| | Protein TSPEAR |
| | GDNF family receptor alpha-3 |
| | Hephaestin |
| | Platelet receptor Gi24 |
| | Butyrophilin-like protein 3 |
| | Progonadoliberin-2 |
| | Butyrophilin-like protein 9 |
| | Kallikrein-7 |
| | Laminin subunit gamma-2 |
| | Apolipoprotein F |
| | Protein LMBR1L |
| | Protein CASC4 |
| | Mucin-21 |
| | VIP36-like protein |
| | Endoplasmic reticulum mannosyl-oligosaccharide 1,2-alpha-mannosidase |
| | Magnesium transporter protein 1 |
| | Amiloride-sensitive amine oxidase [copper-containing] |
| A disintegrin and metalloproteinase 2 | DNA damage-regulated autophagy |
| | Pancreatic secretory granule membrane |
| | Ephrin-A1 |
| | R-spondin-2 |
| | Transmembrane and coiled-coil domain-containing protein 3 |
| | VEGF co-regulated chemokine 1 |
| | ADM2 |
| | Hydroxysteroid 11-beta-dehydrogenase 1-like protein |
| | Delta-like protein 1 |
| | Bone sialoprotein 2 |
| | Lymphotactin |
| | Growth-regulated alpha protein |
| | Mucin-15 |
| | Semenogelin 2 |
| | RING finger protein 43 |
| | Regenerating islet-derived protein 3 gamma |
| | Serine beta-lactamase-like protein LACTB, mitochondrial |

TABLE 1-continued

| | | | |
|---|---|---|---|
| subunit beta | thrombospondin motifs 1 | modulator protein 2 | major glycoprotein GP2 |
| Podocalyxin-like protein 2 | Protein COQ10A, mitochondrial | Transmembrane protein C17orf87 | Semaphorin-4B |
| Prominin-2 | Uncharacterized protein C19orf41 | Complement factor H-related protein 5 | Semaphorin-5B |
| Plexin domain-containing protein 2 | Uncharacterized protein C21orf63 | FK506-binding protein 7 | Epsilon-sarcoglycan |
| Roundabout homolog 4 | Protein delta homolog 2 | Serine incorporator 1 | Guanylate-binding protein 5 |
| Lactosylceramide alpha-2,3-sialyltransferase | Cocaine- and amphetamine-regulated transcript protein | Transmembrane and ubiquitin-like domain-containing protein 1 | Ectonucleoside triphosphate diphosphohydrolase 6 |
| SID1 transmembrane family member 2 | Lipoma HMGIC fusion partner-like 1 protein | Protein ERGIC-53-like | Serpin B3 |
| Sushi domain-containing protein 1 | Leucine-rich repeat-containing protein 18 | Toll-like receptor 10 | Protein RMD5 homolog B |
| Serine/threonine-protein kinase TAO2 | Leucine-rich repeat-containing protein 25 | Toll-like receptor 8 | Scavenger receptor class A member 5 |
| Transmembrane protease, serine 2 | Leucine-rich repeat-containing protein 3B | Selenoprotein T | Semaphorin-6B |
| UDP-glucuronic acid decarboxylase 1 | Leucine-rich repeat-containing protein 3 | Sialic acid-binding Ig-like lectin 11 | Transmembrane protein 108 |
| Uncharacterized protein C10orf58 | Ly6/PLAUR domain-containing protein 4 | Sorting nexin-24 | Sushi domain-containing protein 3 |
| Thioredoxin-related transmembrane protein 2 | Vitamin K epoxide reductase complex subunit 1 | Complement C1q tumor necrosis factor-related protein 1 | Latent-transforming growth factor beta-binding protein 2 |
| CMP-N-acetylneuraminate-beta-galactosamide-alpha-2,3-sialyltransferase | A disintegrin and metalloproteinase with thrombospondin motifs 20 | Putative uncharacterized protein UNQ6494/PRO21346 | Putative uncharacterized protein UNQ6190/PRO20217 |
| Putative uncharacterized protein ENSP00000380674 | Putative uncharacterized protein ENSP00000381830 | Secreted and transmembrane 1 precursor variant | Secreted and transmembrane 1 precursor variant |
| Transmembrane protein 119 | Cat eye syndrome critical region protein 1 | C-type lectin domain family 18 member A | Collagen alpha-1(XX) chain |
| Transmembrane protein 98 | Testis-expressed protein 101 | Cysteine-rich secretory protein 3 | Netrin receptor UNC5D |
| Pre-B lymphocyte protein 3 | Xylosyltransferase 2 | Complement C4-A | Mucin-13 |
| Putative uncharacterized protein C14orf144 | Protein FAM20A | Putative uncharacterized protein PRO2829 | ATP-dependent metalloprotease YME1L1 |
| Membrane-bound transcription factor site-1 protease | Transmembrane and immunoglobulin domain-containing protein 1 | Calcium-activated chloride channel regulator 2 | Proprotein convertase subtilisin/kexin type 5 |
| Ficolin (Collagen/fibrinogen domain containing) 3 (Hakata antigen) (NL3) (Ficolin (Collagen/fibrinogen domain containing) 3 (Hakata antigen), isoform CRA_b) | Putative killer cell immunoglobulin-like receptor-like protein KIR3DX1 (Leukocyte receptor cluster member 12) | Neuroblastoma suppressor of tumorigenicity 1 | |

The therapeutic proteins provided herein should not be considered to be exclusive. Rather, as is apparent from the disclosure provided herein, the methods of the invention are applicable to any protein wherein attachment of a water soluble fatty acid derivative is desired according to the invention. For example, therapeutic proteins are described in US 2007/0026485, incorporated herein by reference in its entirety.

Blood Coagulation Proteins

In one aspect, the starting material of the present invention is a blood coagulation protein, which can be derived from human plasma, or produced by recombinant engineering techniques, as described in patents U.S. Pat. Nos. 4,757,006; 5,733,873; 5,198,349; 5,250,421; 5,919,766; and EP 306 968.

Therapeutic polypeptides such as blood coagulation proteins including Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, tPA, PAI-1, tissue factor (TF) and ADAMTS 13 protease are rapidly degraded by proteolytic enzymes and neutralized by antibodies. This reduces their half-life and circulation time, thereby limiting their therapeutic effectiveness. Relatively high doses and frequent administration are necessary to reach and sustain the desired therapeutic or prophylactic effect of these coagulation proteins. As a consequence, adequate dose regulation is difficult to obtain and the need of frequent intravenous administrations imposes restrictions on the patient's way of living.

As described herein, blood coagulation proteins including, but not limited to, Factor IX (FIX), Factor VIII (FVIII), Factor VIIa (FVIIa), von Willebrand Factor (VWF), Factor FV (FV), Factor X (FX), Factor XI, Factor XII (FXII), thrombin (FII), protein C, protein S, tPA, PAI-1, tissue factor (TF) and ADAMTS 13 protease are contemplated by the invention. As used herein, the term "blood coagulation protein" refers to any Factor IX (FIX), Factor VIII (FVIII), Factor VIIa (FVIIa), von Willebrand Factor (VWF), Factor FV (FV), Factor X (FX), Factor XII (FXII), thrombin (FII), protein C, protein S, tPA, PAI-1, tissue factor (TF) and ADAMTS 13 protease which exhibits biological activity that is associated with that particular native blood coagulation protein.

The blood coagulation cascade is divided into three distinct segments: the intrinsic, extrinsic, and common pathways (Schenone et al., Curr Opin Hematol. 2004; 11:272-7). The cascade involves a series of serine protease enzymes (zymogens) and protein cofactors. When required, an inactive zymogen precursor is converted into the active form, which consequently converts the next enzyme in the cascade.

The intrinsic pathway requires the clotting factors VIII, IX, X, XI, and XII. Initiation of the intrinsic pathway occurs when prekallikrein, high-molecular-weight kininogen, factor XI (FXI) and factor XII (FXII) are exposed to a negatively charged surface. Also required are calcium ions and phospholipids secreted from platelets.

The extrinsic pathway is initiated when the vascular lumen of blood vessels is damaged. The membrane glycoprotein tissue factor is exposed and then binds to circulating factor VII (FVII) and to small preexisting amounts of its activated form FVIIa. This binding facilitates full conversion of FVII to FVIIa and subsequently, in the presence of calcium and phospholipids, the conversion of factor IX (FIX) to factor IXa (FIXa) and factor X (FX) to factor Xa (FXa). The association of FVIIa with tissue factor enhances the proteolytic activity by bringing the binding sites of FVII for the substrate (FIX and FX) into closer proximity and by inducing a conformational change, which enhances the enzymatic activity of FVIIa.

The activation of FX is the common point of the two pathways. Along with phospholipid and calcium, factors Va (FVa) and Xa convert prothrombin to thrombin (prothrombinase complex), which then cleaves fibrinogen to form fibrin monomers. The monomers polymerize to form fibrin strands. Factor XIIIa (FXIIIa) covalently bonds these strands to one another to form a rigid mesh.

Conversion of FVII to FVIIa is also catalyzed by a number of proteases, including thrombin, FIXa, FXa, factor XIa (FXIa), and factor XIIa (FXIIa). For inhibition of the early phase of the cascade, tissue factor pathway inhibitor targets FVIIa/tissue factor/FXa product complex.

Factor VIIa

FVII (also known as stable factor or proconvertin) is a vitamin K-dependent serine protease glycoprotein with a pivotal role in hemostasis and coagulation (Eigenbrot, Curr Protein Pept Sci. 2002; 3:287-99).

FVII is synthesized in the liver and secreted as a single-chain glycoprotein of 48 kD. FVII shares with all vitamin K-dependent serine protease glycoproteins a similar protein domain structure consisting of an amino-terminal gamma-carboxyglutamic acid (Gla) domain with 9-12 residues responsible for the interaction of the protein with lipid membranes, a carboxy-terminal serine protease domain (catalytic domain), and two epidermal growth factor-like domains containing a calcium ion binding site that mediates interaction with tissue factor. Gamma-glutamyl carboxylase catalyzes carboxylation of Gla residues in the amino-terminal portion of the molecule. The carboxylase is dependent on a reduced form of vitamin K for its action, which is oxidized to the epoxide form. Vitamin K epoxide reductase is required to convert the epoxide form of vitamin K back to the reduced form.

The major proportion of FVII circulates in plasma in zymogen form, and activation of this form results in cleavage of the peptide bond between arginine 152 and isoleucine 153. The resulting activated FVIIa consists of a $NH_2$-derived light chain (20 kD) and a COOH terminal-derived heavy chain (30 kD) linked via a single disulfide bond (Cys 135 to Cys 262). The light chain contains the membrane-binding Gla domain, while the heavy chain contains the catalytic domain.

The plasma concentration of FVII determined by genetic and environmental factors is about 0.5 mg/mL (Pinotti et al., Blood. 2000; 95:3423-8). Different FVII genotypes can result in several-fold differences in mean FVII levels. Plasma FVII levels are elevated during pregnancy in healthy females and also increase with age and are higher in females and in persons with hypertriglyceridemia. FVII has the shortest half-life of all procoagulant factors (3-6 h). The mean plasma concentration of FVIIa is 3.6 ng/mL in healthy individuals and the circulating half-life of FVIIa is relatively long (2.5 h) compared with other coagulation factors.

Hereditary FVII deficiency is a rare autosomal recessive bleeding disorder with a prevalence estimated to be 1 case per 500,000 persons in the general population (Acharya et al., J Thromb Haemost. 2004; 2248-56). Acquired FVII deficiency from inhibitors is also very rare. Cases have also been reported with the deficiency occurring in association with drugs such as cephalosporins, penicillins, and oral anticoagulants. Furthermore, acquired FVII deficiency has been reported to occur spontaneously or with other conditions, such as myeloma, sepsis, aplastic anemia, with interleukin-2 and antithymocyte globulin therapy.

Reference polynucleotide and polypeptide sequences include, e.g., GenBank Accession Nos. J02933 for the genomic sequence, M13232 for the cDNA (Hagen et al. PNAS 1986; 83: 2412-6), and P08709 for the polypeptide sequence (references incorporated herein in their entireties). A variety of polymorphisms of FVII have been described, for example see Sabater-Lleal et al. (Hum Genet. 2006; 118:741-51) (reference incorporated herein in its entirety).

Factor IX

FIX is a vitamin K-dependent plasma protein that participates in the intrinsic pathway of blood coagulation by converting FX to its active form in the presence of calcium ions, phospholipids and FVIIIa. The predominant catalytic capability of FIX is as a serine protease with specificity for a particular arginine-isoleucine bond within FX. Activation of FIX occurs by FXIa which causes excision of the activation peptide from FIX to produce an activated FIX molecule comprising two chains held by one or more disulphide bonds. Defects in FIX are the cause of recessive X-linked hemophilia B.

Hemophilia A and B are inherited diseases characterized by deficiencies in FVIII and FIX polypeptides, respectively. The underlying cause of the deficiencies is frequently the result of mutations in FVIII and FIX genes, both of which are located on the X chromosome. Traditional therapy for hemophilias often involves intravenous administration of pooled plasma or semi-purified coagulation proteins from normal individuals. These preparations can be contaminated by pathogenic agents or viruses, such as infectious prions, HIV, parvovirus, hepatitis A, and hepatitis C. Hence, there is an urgent need for therapeutic agents that do not require the use of human serum.

The level of the decrease in FIX activity is directly proportional to the severity of hemophilia B. The current treatment of hemophilia B consists of the replacement of the missing protein by plasma-derived or recombinant FIX (so-called FIX substitution or replacement treatment or therapy).

Polynucleotide and polypeptide sequences of FIX can be found for example in the UniProtKB/Swiss-Prot Accession No. P00740, and U.S. Pat. No. 6,531,298.

Factor VIII

Coagulation factor VIII (FVIII) circulates in plasma at a very low concentration and is bound non-covalently to von Willebrand factor (VWF). During hemostasis, FVIII is separated from VWF and acts as a cofactor for activated factor IX (FIXa)-mediated FX activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma (e.g., "plasma-derived" or "plasmatic"), FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assays. This activation and inactivation coincides with specific limited proteolysis both in the heavy and the light chains, which alter the availability of different binding epitopes in FVIII, e.g. allowing FVIII to dissociate from VWF and bind to a phospholipid surface or altering the binding ability to certain monoclonal antibodies.

The lack or dysfunction of FVIII is associated with the most frequent bleeding disorder, hemophilia A. The treatment of choice for the management of hemophilia A is replacement therapy with plasma derived or rFVIII concentrates. Patients with severe haemophilia A with FVIII levels below 1%, are generally on prophylactic therapy with the aim of keeping FVIII above 1% between doses. Taking into account the average half-lives of the various FVIII products in the circulation, this result can usually be achieved by giving FVIII two to three times a week.

Reference polynucleotide and polypeptide sequences include, e.g., UniProtKB/Swiss-Prot P00451 (FA8_HUMAN); Gitschier J et al., Characterization of the human Factor VIII gene, Nature, 312(5992): 326-30 (1984); Vehar G H et al., Structure of human Factor VIII, Nature, 312(5992):337-42 (1984); Thompson A R. Structure and Function of the Factor VIII gene and protein, Semin Thromb Hemost, 2003:29; 11-29 (2002).

Von Willebrand Factor

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates initial platelet adhesion to the sub-endothelium of the damaged vessel wall. Only the larger multimers exhibit hemostatic activity. It is assumed that endothelial cells secrete large polymeric forms of VWF and those forms of VWF which have a low molecular weight (low molecular weight VWF) arise from proteolytic cleavage. The multimers having large molecular masses are stored in the Weibel-Pallade bodies of endothelial cells and liberated upon stimulation.

VWF is synthesized by endothelial cells and megakaryocytes as prepro-VWF that consists to a large extent of repeated domains. Upon cleavage of the signal peptide, pro-VWF dimerizes through disulfide linkages at its C-terminal region. The dimers serve as protomers for multimerization, which is governed by disulfide linkages between the free end termini. The assembly to multimers is followed by the proteolytic removal of the propeptide sequence (Leyte et al., Biochem. J. 274 (1991), 257-261).

The primary translation product predicted from the cloned cDNA of VWF is a 2813-residue precursor polypeptide (prepro-VWF). The prepro-VWF consists of a 22 amino acid signal peptide and a 741 amino acid propeptide, with the mature VWF comprising 2050 amino acids (Ruggeri Z. A., and Ware, J., FASEB J., 308-316 (1993).

Defects in VWF are causal to von Willebrand disease (VWD), which is characterized by a more or less pronounced bleeding phenotype. VWD type 3 is the most severe form in which VWF is completely missing, and VWD type 1 relates to a quantitative loss of VWF and its phenotype can be very mild. VWD type 2 relates to qualitative defects of VWF and can be as severe as VWD type 3. VWD type 2 has many sub forms, some being associated with the loss or the decrease of high molecular weight multimers. Von Willebrand disease type 2a (VWD-2A) is characterized by a loss of both intermediate and large multimers. VWD-2B is characterized by a loss of highest-molecular-weight multimers. Other diseases and disorders related to VWF are known in the art.

The polynucleotide and amino acid sequences of prepro-VWF are available at GenBank Accession Nos. NM_000552 and NP_000543, respectively.

Other blood coagulation proteins according to the present invention are described in the art, e.g. Mann K G, Thromb Haemost, 1999; 82:165-74.

A. Polypeptides

In one aspect, the starting material of the present invention is a protein or polypeptide. As described herein, the term therapeutic protein refers to any therapeutic protein molecule which exhibits biological activity that is associated with the therapeutic protein. In one embodiment of the invention, the therapeutic protein molecule is a full-length protein.

Therapeutic protein molecules contemplated include full-length proteins, precursors of full length proteins, biologically active subunits or fragments of full-length proteins, as well as biologically active derivatives and variants of any of these forms of therapeutic proteins. Thus, therapeutic protein include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids, to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

According to the present invention, the term "recombinant therapeutic protein" includes any therapeutic protein obtained via recombinant DNA technology. In certain embodiments, the term encompasses proteins as described herein.

As used herein, "endogenous therapeutic protein" includes a therapeutic protein which originates from the mammal intended to receive treatment. The term also includes therapeutic protein transcribed from a transgene or any other foreign DNA present in said mammal. As used herein, "exogenous therapeutic protein" includes a blood coagulation protein which does not originate from the mammal intended to receive treatment.

As used herein, "plasma-derived blood coagulation protein" or "plasmatic" includes all forms of the protein found in blood obtained from a mammal having the property participating in the coagulation pathway.

As used herein "biologically active derivative" or "biologically active variant" includes any derivative or variant of a molecule having substantially the same functional and/or biological properties of said molecule, such as binding properties, and/or the same structural basis, such as a peptidic backbone or a basic polymeric unit.

An "analog," "variant" or "derivative" is a compound substantially similar in structure and having the same biological activity, albeit in certain instances to a differing degree, to a naturally-occurring molecule. For example, a polypeptide variant refers to a polypeptide sharing substantially similar structure and having the same biological activity as a reference polypeptide. Variants or analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence. By way of example, a "derivative" refers to a polypeptide sharing the same or substantially similar structure as a reference polypeptide that has been modified, e.g., chemically.

In various embodiments, analogs, variants or derivatives are designed to allow, for example, conjugation of another molecule to the protein analog, variant or derivative, thereby forming a conjugated protein according to the present invention.

Variant or analog polypeptides include insertion variants, wherein one or more amino acid residues are added to a therapeutic protein amino acid sequence of the invention. Insertions may be located at either or both termini of the protein, and/or may be positioned within internal regions of the therapeutic protein amino acid sequence. Insertion variants, with additional residues at either or both termini, include for example, fusion proteins and proteins including amino acid tags or other amino acid labels. In one aspect, the blood coagulation protein molecule optionally contains an N-terminal Met, especially when the molecule is expressed recombinantly in a bacterial cell such as E. coli.

In deletion variants, one or more amino acid residues in a therapeutic protein polypeptide as described herein are removed. Deletions can be effected at one or both termini of the therapeutic protein polypeptide, and/or with removal of one or more residues within the therapeutic protein amino acid sequence. Deletion variants, therefore, include fragments of a therapeutic protein polypeptide sequence.

In substitution variants, one or more amino acid residues of a therapeutic protein polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 7'-77] and are set out immediately below.

| CONSERVATIVE SUBSTITUTIONS | |
|---|---|
| SIDE CHAIN CHARACTERISTIC | AMINO ACID |
| Non-polar (hydrophobic): | |
| A. Aliphatic | A L I V P |
| B. Aromatic | F W |
| C. Sulfur-containing | M |
| D. Borderline | G |
| Uncharged-polar: | |
| A. Hydroxyl | S T Y |
| B. Amides | N Q |
| C. Sulfhydryl | C |
| D. Borderline | G |
| Positively charged (basic) | K R H |
| Negatively charged (acidic) | D E |

Alternatively, exemplary conservative substitutions are set out immediately below.

| CONSERVATIVE SUBSTITUTIONS II | |
|---|---|
| ORIGINAL RESIDUE | EXEMPLARY SUBSTITUTION |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

B. Polynucleotides

Nucleic acids encoding a therapeutic protein of the invention include, for example and without limitation, genes, pre-mRNAs, mRNAs, cDNAs, polymorphic variants, alleles, synthetic and naturally-occurring mutants.

Polynucleotides encoding a therapeutic protein of the invention also include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 1218 nucleotides of the mature protein), to a reference nucleic acid sequence as described herein. Exemplary "stringent hybridization" conditions include hybridization at 42° C. in 50% formamide, 5×SSC, 20 mM Na.PO4, pH 6.8; and washing in 1×SSC at 55° C. for 30 minutes. It is understood that variation in these exemplary conditions can be made based on the length and GC nucleotide content of the sequences to be hybridized. Formulas standard in the art are appropriate for determining appropriate hybridization conditions. See Sambrook et al., Molecular Cloning: A Laboratory Manual (Second ed., Cold Spring Harbor Laboratory Press, 1989) §§9.47-9.51.

A "naturally-occurring" polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention can be recombinant molecules (e.g., heterologous and encoding the wild type sequence or a variant thereof, or non-naturally occurring).

C. Production of Therapeutic Proteins

Production of a therapeutic protein includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing therapeutic protein, e.g. constitutively or upon induction, and (v) isolating said blood coagulation protein, e.g. from the culture medium or by harvesting the transformed cells, in order to obtain purified therapeutic protein.

In other aspects, the therapeutic protein is produced by expression in a suitable prokaryotic or eukaryotic host system characterized by producing a pharmacologically acceptable blood coagulation protein molecule. Examples of eukaryotic cells are mammalian cells, such as CHO, COS, HEK 293, BHK, SK-Hep, and HepG2.

A wide variety of vectors are used for the preparation of the therapeutic protein and are selected from eukaryotic and prokaryotic expression vectors. Examples of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and β-actin.

In various embodiments of the invention, therapeutic proteins are modified by conjugating water soluble fatty acid derivatives or water soluble linkers to one or more carbohydrates on the therapeutic protein. Thus, in one embodiment, the therapeutic protein is a glycoprotein and is purified from a host cell that allows glycosylation (i.e., the protein is glycosylated in vivo and subsequently purified as a glycoprotein.). In various embodiments, the therapeutic protein is or is not a glycoprotein and is glycosylated in vitro following purification from a host cell. In vitro glycosylation methods are well known in the art (See, e.g., Meynial-Salles I and Combes D, Journal of Biotechnology 1996, 46:1-14; /Solá R J and Griebenow K, BioDrugs 2010, 24:9-21). Of course, one of skill in the art could (1) purify the therapeutic protein; (2) modify the therapeutic protein to allow for in vitro, optionally site-specific, glycosylation (e.g., amino acid deletions/insertion/substitutions); and (3) glycosylate the modified protein in vitro according to procedures known in the art.

D. Administration

In one embodiment a conjugated therapeutic protein of the present invention may be administered by injection, such as intravenous, intramuscular, or intraperitoneal injection.

To administer compositions comprising a conjugated therapeutic protein of the present invention to human or test animals, in one aspect, the compositions comprise one or more pharmaceutically acceptable carriers. The terms "pharmaceutically" or "pharmacologically acceptable" refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

As used herein, "effective amount" includes a dose suitable for treating a disease or disorder or ameliorating a symptom of a disease or disorder. In one embodiment, "effective amount" includes a dose suitable for treating a mammal having a bleeding disorder as described herein.

The compositions may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions can be carried out with the dose levels and pattern being selected by the treating physician. For the prevention or treatment of disease, the appropriate dosage will depend on the type of disease to be treated, as described above, the severity and course of the disease, whether drug is administered for preventive or therapeutic purposes, previous therapy, the patient's clinical history and response to the drug, and the discretion of the attending physician.

The present invention also relates to a pharmaceutical composition comprising an effective amount of a conjugated therapeutic protein as defined herein. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. Solutions of the pharmaceutical composition may be subjected to any suitable lyophilization process. As an additional aspect, the invention includes kits which comprise a composition of the invention packaged in a manner which facilitates its use for administration to subjects. In one embodiment, such a kit includes a compound or composition described herein (e.g., a composition comprising a conjugated therapeutic protein), packaged in a container such as a sealed bottle or vessel, with a label affixed to the container or included in the package that describes use of the compound or composition in practicing the method. In one embodiment, the kit contains a first container having a composition comprising a conjugated therapeutic protein and a second container having a physiologically acceptable reconstitution solution for the composition in the first container. In one aspect, the compound or composition is packaged in a unit dosage form. The kit may further include a device suitable for administering the composition according to a specific route of administration. Preferably, the kit contains a label that describes use of the therapeutic protein or peptide composition.

Fatty Acids, Fatty Acid Derivatives, and Protein-Fatty Acid Derivative Conjugates In one aspect, a therapeutic protein derivative (i.e., a conjugated therapeutic protein) molecule provided herein is bound to a water-soluble fatty acid derivative. As used herein, a "water soluble fatty acid derivative" comprises a fatty acid (i.e., a carboxylic acid) conjugated to a water soluble linker (e.g., an aminooxy linker) as described herein. Such fatty acid derivatives, according to the invention, are stable (i.e., are not released from the protein), water soluble, and capable of binding to human serum albumin.

A. Fatty acids

Fatty acids (i.e., FA or FAs) include, but are not limited to, saturated fatty acids, unsaturated fatty acids, branched chain fatty acids (Mukheriji et al., Prog Lipid Res 2003; 42:359-76) and derivatives thereof that are capable of binding human serum albumin according to the present invention.

By way of example, fatty acids have the following general structure:

Saturated FA: general structure

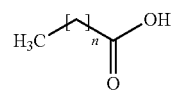

Saturated FA methyl ester: general structure

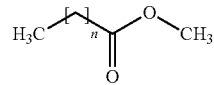

Saturated FA ethyl ester: general structure

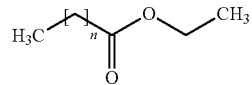

Fatty acids, according to various embodiments of the present invention, also comprise various alternative structures (e.g. methyl- or ethyl esters) or other structures such as containing terminal groups in ω-position (e.g. hydroxyl, amino, thio and carboxyl groups).

In one embodiment, the fatty acid is a naturally-occurring fatty acid. In various embodiments, the fatty acid is a short chain fatty acid (e.g., less than six carbons), a medium chain fatty acid (e.g., 6-12 carbons), long chain fatty acids (e.g., longer than 12 carbons), or a very long chain fatty acid (e.g., longer than 22 carbons). In another embodiment, the fatty acid has between 4 and 28 carbons. In one embodiment, the fatty acid is in the cis configuration. In still another embodiment, the fatty acid is in the trans configuration.

In one embodiment, the fatty acid is a saturated fatty acid between 12 and 20 carbons in length. Such fatty acids are known in the art, e.g., C12 (Dodecanoic acid, Lauric acid), C14 (Tetradecanoic acid, Myristic acid), C16 (Hexadecanoic acid, Palmitic acid), C18 (Octadecanoic acid, Stearic acid) and C20 (Eicosanoic acid, Arachidic acid). Examples of unsaturated fatty acids are Myristoleic acid (C14:1), Palmitoleic acid (C16:1), Oleic acid (C18:1), Linoleic acid (C18:2) and Arachidonic acid (C20:4). Most of the fatty acids are commercially available and can be prepared by different chemical methods (Recent Developments in the Synthesis of Fatty Acid Derivatives, Editors: Knothe G and Derksen JTB, AOCS Press 1999, ISBN 1-893997-00-6.)

In various embodiments of the present invention, the fatty acid comprises 4, 6, 8, 10, 12, 14, 16, 18, 20, 22, 24, 26, 28, 30, 32, 34, 36, 38, 40, 42, 44, 46, 48, or 50 carbons.

B. Fatty Acid Derivatives

The present invention provides the preparation of a novel class of activated fatty acid derivatives (FA derivatives) which can bind human serum albumin. The FA derivatives contain a water soluble spacer or linker, which allows the handling and manipulation of FA derivatives in aqueous solution (i.e., the fatty acid derivatives according to the present invention are water soluble, unlike the corresponding fatty acids from which they are derived). In one embodiment, the FA derivatives contain an active aminooxy group, which allows the coupling of the FA derivative to an oxidized carbohydrate moiety (predominantly N-glycans) of therapeutic proteins to form stable oxime linkages. As used herein, a "stable" linkage means that a covalent bond is formed which is "non-releasable" or non-hydrolyzable.

The chemical modification via carbohydrates might be the preferred option for coagulation proteins like FVIII, FIX and FVIIa to form conjugates with high residual activity.

By way of example and without limitation, the following strategy represents one embodiment according to the present invention to prepare a water soluble FA derivative containing an active aminooxy group.

Strategy 1:

The ω-hydroxy group of a FA derivative (e.g. 16-hydroxyhexadecanoic acid) is subjected to oxidation with Dess Martin periodinane to generate an aldehyde group. In the next step a diaminooxy linker containing a water soluble PEG chain (e.g. 3,6,9-trioxaundecane-1,11-dioxyamine) is coupled to this aldehyde group to form a stable oxime linkage. The following schematic represents one example according to Strategy 1:

Step 1: 16-hydroxystearic acid was selectively oxidized with Dess-Martin reagent to yield 16-oxostearic acid. The crude product was purified by chromatography using silica gel as separating agent.

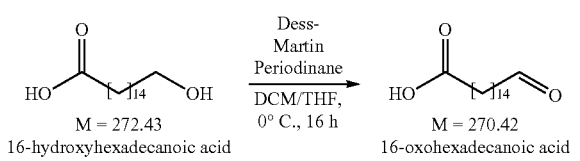

Step 2: The 16-oxo moiety of 16-oxostearic acid sodium salt was reacted with 3,6,9-trioxaundecane-1,11-dioxyamine. The crude product was purified by chromatography using silica gel as separating agent.

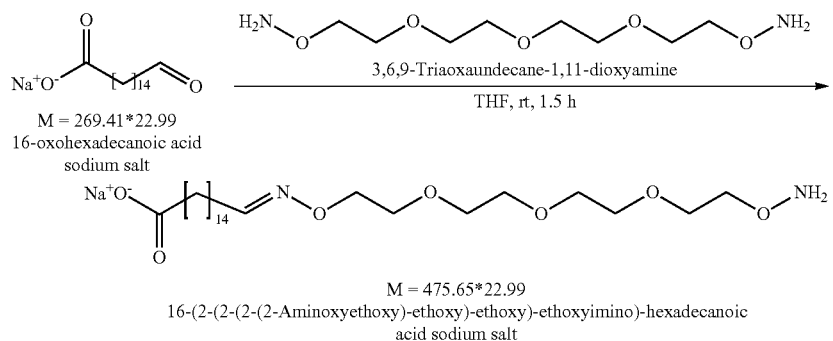

The following schematic represents one example according to Strategy 2:

Step 1: The carboxylic acid moiety of 16-hydroxyhexadecanoic acid was protected by forming the methyl ester using acetyl chloride as the methylation reagent.

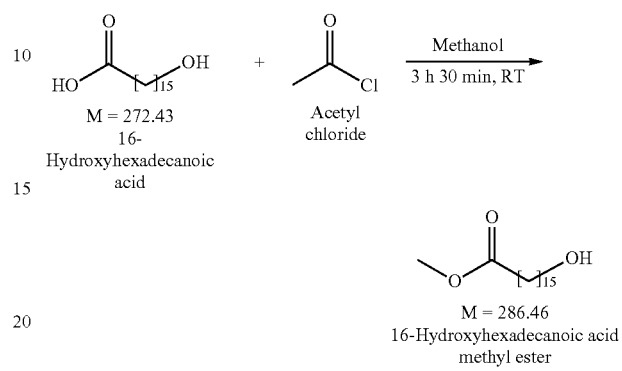

Step 2: The 16-hydroxy moiety of 16-hydroxyhexadecanoic acid methyl ester was activated by substituting the hydroxyl group with mesyl, which is the better leaving group.

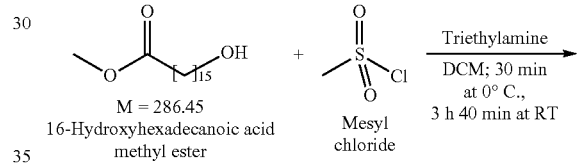

Alternatively, another embodiment, the following strategy is employed to prepare a water soluble FA derivatives containing an active aminooxy group.

Strategy 2:

The carboxyl group of a ω-hydroxy fatty acid (e.g. 16-hydroxyhexadecanoic acid) is esterified with acetyl chloride. The ω-hydroxy group of this methyl ester derivative is activated with mesyl chloride to introduce a better leaving group. Then the mesyl group is reacted with a diaminooxy linker containing a water soluble PEG chain (e.g. 3,6,9-trioxaundecane-1,11-dioxyamine) to form a stable aminooxy-methylene bond. Optionally the methyl ester can be hydrolyzed in alkaline solution to generate a free carboxyl group.

-continued

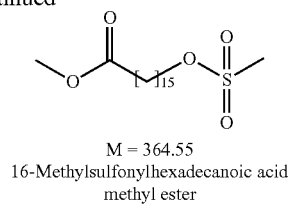

Step 3: The 16-mesyl moiety of 16-methylsulfonylhexadecanoic acid methyl ester was substituted by one aminooxy moiety of the bifunctional 3,6,9-trioxaundecane-1,11-dioxyamine. The crude product is purified by chromatography using silica gel as separating agent.

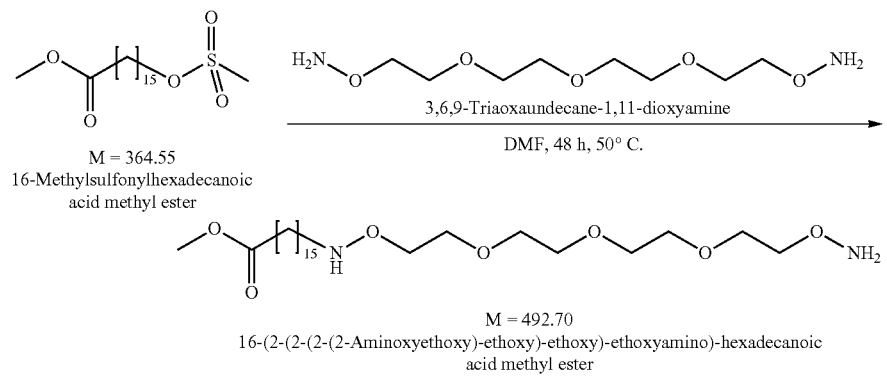

Additional strategies are also contemplated by the present invention. The present invention, for example, is not restricted to aminooxy chemistry for coupling to the aldehyde groups of oxidized carbohydrate residues. As described herein, the use of other chemistries including, but not limited to hydrazides for coupling to aldehyde groups, NHS esters for coupling to amino groups and maleimides for coupling to free SH-groups of therapeutic proteins are also contemplated.

By way of example, a fatty acid methyl ester prepared as described above is reacted with a commercially-available MAL-PEG-COOH (mal-PEG(12)-COOH/IRIS Biotech GmbH, Marktredwitz, Germany) as described herein. By way of still another example, a fatty acid ester with a reactive amino group is reacted with a commercially available NHS-PEG-NHS (NHS-dPEG(4)-NHS/IRIS Biotech GmbH, Marktredwitz, Germany) as described herein.

Water soluble linkers include, but are not limited to, water soluble polymers (e.g. PEG). The linker can consist of any chemical structure containing one or more functional groups, which increase its water solubility. These functional groups could have the ability to form a negative or positive charge, thereby making the linker water soluble. In one embodiment this functional group includes, but is not limited to a sulfo or carboxyl group. In addition any polar functional group can be used, which makes the linker more water soluble. Examples for this are hydroxyl, amino, amido, maleimido, aminooxy and hydrazide groups as well as N-hydroxy succinimide (NHS) esters and sulfo NHS esters.

In various embodiments, the water soluble polymer includes, but is not limited to, polyethylene glycol (PEG), branched PEG, polysialic acid (PSA), hydroxyalkyl starch (HAS), hydroxyethyl starch (HES), carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC).

In one embodiment, the water soluble polymer is PEG. In various embodiments of the invention, the water soluble polymer comprises a chain length of between approximately 3 to 25 oxygens. For example, the water soluble polymer comprises 3, 5, 7, 9, 11, 13, 15, 17, 19, 21, 23, or 25 oxygens, in various embodiments according the present invention.

C. Protein-Fatty Acid Derivative Conjugates

Aminooxy linker systems (i.e., wherein a water soluble fatty acid derivative comprises an aminooxy linker) are contemplated by the present invention. For example, in one embodiment of the invention, the reaction of hydroxylamine or hydroxylamine derivatives with aldehydes (e.g., on a carbohydrate moiety following oxidation by sodium periodate) to form an oxime group is applied to the preparation of protein conjugates. For example, a glycoprotein (e.g., a therapeutic protein according to the present invention) is first oxidized with an oxidizing agent such as sodium periodate (NaIO4) (Rothfus J A et Smith E L., J Biol Chem 1963, 238, 1402-10; and Van Lenten L and Ashwell G., J Biol Chem 1971, 246, 1889-94). The periodate oxidation of glycoproteins is based on the classical Malaprade reaction described in 1928, the oxidation of vicinal diols with periodate to form an active aldehyde group (Malaprade L., Analytical application, Bull Soc Chim France, 1928, 43, 683-96). Additional examples for such an oxidizing agent are lead tetraacetate (Pb(OAc)4), manganese acetate (MnO(Ac)3), cobalt acetate (Co(OAc)2), thallium acetate (TlOAc), cerium sulfate (Ce(SO4)2) (U.S. Pat. No. 4,367,309) or potassium perruthenate (KRuO4) (Marko et al., J Am Chem Soc 1997,119, 12661-2). By "oxidizing agent" a mild oxidizing compound which is capable of oxidizing vicinal diols in carbohydrates, thereby generating active aldehyde groups under physiological reaction conditions is meant.

The second step is the coupling of the polymer (e.g., fatty acid derivative) containing an aminooxy group to the oxidized carbohydrate moiety to form an oxime linkage. In one embodiment of the invention, this step can be carried out in the presence of catalytic amounts of the nucleophilic catalyst aniline or aniline derivatives (Dirksen A et Dawson P E, Bioconjugate Chem. 2008; Zeng Y et al., Nature Methods 2009; 6:207-9). The aniline catalysis dramatically accelerates the oxime ligation allowing the use of very low concentrations of the reagents. In another embodiment of the invention the oxime linkage is stabilized by reduction with NaCNBH3 to form an alkoxyamine linkage. Additional catalysts are described below. In another embodiment, this step is carried out in the presence of m-toluidine.

In one embodiment of the invention, the reaction steps to conjugate a water soluble linker (e.g., fatty acid derivative) to a protein are carried out separately and sequentially (i.e., starting materials (e.g., therapeutic protein, water soluble linker, etc), reagents (e.g., oxidizing agents, aniline, etc) and reaction products (e.g., oxidized carbohydrate on a therapeutic protein, activated aminooxy water soluble linker, etc) are separated between individual reaction steps). In another embodiment, the starting materials and reagents necessary to complete a conjugation reaction according to the present invention is carried out in a single vessel. In one embodiment the native protein is mixed with the aminooxy-polymer reagent. Subsequently the oxidizing reagent is added and the conjugation reaction is performed.

Additional information on aminooxy technology can be found in the following references, each of which is incorporated in their entireties: EP 1681303A1 (HASylated erythropoietin); WO 2005/014024 (conjugates of a polymer and a protein linked by an oxime linking group); WO96/40662 (aminooxy-containing linker compounds and their application in conjugates); WO 2008/025856 (Modified proteins); Peri F et ar., Tetrahedron 1998, 54, 12269-78; Kubler-Kielb J and Pozsgay V., J Org Chem 2005, 70, 6887-90; Lees A et al., Vaccine 2006, 24(6), 716-29; and Heredia K L et al., Macromolecules 2007, 40(14), 4772-9.

The coupling of the water soluble linker can be carried out by direct coupling to the protein, e.g., via a free sulfhydryl group or free amino group on the protein) or via a linker molecule described herein. The conjugation is in one aspect performed by direct coupling (or coupling via linker systems) of the water soluble linker to a therapeutic protein under formation of stable bonds.

Thus, in various embodiments of the invention, the fatty acid derivatives described herein are designed to allow conjugation to a therapeutic protein. For example, the fatty acid derivatives are designed to include various terminal reactive groups, as described herein.

In certain aspects, therapeutic proteins are conjugated to a water soluble fatty acid derivatives by any of a variety of chemical methods (Roberts J M et al., Advan Drug Delivery Rev 2002; 54:459-76). For example, in one embodiment a therapeutic protein is modified by the conjugation of fatty acid derivatives to free amino groups of the protein using N-hydroxysuccinimide (NHS) esters. In another embodiment the water soluble fatty acid derivative is coupled to free SH groups using maleimide chemistry. In another embodiment the water soluble fatty acid derivative is coupled by use of hydrazide or aminooxy chemistry to the carbohydrate moieties of the therapeutic protein after prior oxidation.

In one embodiment of the invention, a therapeutic protein is modified via lysine residues by use of water soluble fatty acid derivatives containing an active N-hydroxysuccinimide (NHS) ester. This derivative reacts with the lysine residues of the therapeutic protein under mild conditions by forming a stable amide bond.

In another embodiment of the invention, linkage through a peptide bond between a carboxyl group on one of either the protein or fatty acid derivative and an amine group of the protein or fatty acid derivative, or an ester linkage between a carboxyl group of the protein or fatty acid derivative and a hydroxyl group of the therapeutic protein or fatty acid derivative, is contemplated. Another linkage by which the therapeutic protein is covalently bonded to the fatty acid derivative is via a Schiff base, e.g., between a free amino group on the protein being reacted with an aldehyde group formed at a terminal end of a fatty acid. The generated Schiff base is in one aspect stabilized by specific reduction with NaCNBH3 to form a secondary amine. An alternative approach is the generation of terminal free amino groups in the fatty acid derivative by reductive amination with NH4Cl after prior oxidation. Bifunctional reagents can be used for linking two amino or two hydroxyl groups. For example, a fatty acid derivative containing an amino group is coupled to amino groups of the protein with reagents like BS3 (Bis(sulfosuccinimidyl)suberate/Pierce, Rockford, Ill.). In addition heterobifunctional cross linking reagents like Sulfo-EMCS(N-ϵ-Maleimidocaproyloxy) sulfosuccinimide ester/Pierce) are used for instance to link amine and thiol groups.

In another approach, a fatty acid derivative with an active hydrazide group is prepared and coupled to the carbohydrate moiety of the protein after prior oxidation and generation of aldehyde functions.

As described above, a free amine group of the therapeutic protein reacts with the 1-carboxyl group of a fatty acid derivative to form a peptidyl bond or an ester linkage is formed between the 1-carboxylic acid group and a hydroxyl or other suitable active group on a protein.

In various embodiments, the therapeutic protein is linked to or associated with the fatty acid derivative in stoichiometric amounts (e.g., 1:1, 1:2, 1:3, 1:4, 1:5, 1:6, 1:7, 1:7, 1:8, 1:9, or 1:10, etc.). In various embodiments, 1-6, 7-12 or 13-20 fatty acid derivatives are linked to the protein. In still other embodiments, 1, 2, 3, 4, 5, 6, 7, 8, 9, 10, 11, 12, 13, 14, 15, 16, 17, 18, 19, 20 or more fatty acid derivatives are linked to the protein.

In various embodiments, the therapeutic protein is modified to introduce glycosylation sites (i.e., sites other than the native glycosylation sites). Such modification may be accomplished using standard molecular biological techniques known in the art. Moreover, the therapeutic protein, prior to conjugation to a water soluble linker via one or more carbohydrate moieties, may be glycosylated in vivo or in vitro. These glycosylated sites can serve as targets for conjugation of the proteins with water soluble linkers (US Patent Application No. 20090028822, US Patent Application No. 2009/0093399, US Patent Application No. 2009/0081188, US Patent Application No. 2007/0254836, US Patent Application No. 2006/0111279, and DeFrees S. et al., Glycobiology, 2006, 16, 9, 833-43).

In one embodiment, the conjugated protein retains the full functional activity of native therapeutic protein products, and provides an extended half-life in vivo, as compared to native therapeutic protein products. In another embodiment, the conjugated protein retains at least 20, 21, 22, 23, 24, 25, 26, 27, 28, 29, 30, 31, 32, 33, 34, 35, 36, 37, 38, 39, 40, 41, 42, 43, 44. 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native protein.

In a related aspect, the biological activities of the conjugated protein and native blood coagulation protein are determined by the ratios of chromogenic activity to blood coagulation factor antigen value (blood coagulation factor:Chr: blood coagulation factor:Ag).

In still another embodiment of the invention, the half-life of the conjugated protein is decreased or increased 0.5, 0.6, 0.7, 0.8, 0.9, 1.0, 1.1, 1.2, 1.3, 1.4, 1.5, 2, 3, 4, 5, 6, 7, 8, 9, or 10-fold relative to the in vivo half-life of native therapeutic protein.

Nucleophilic Catalysts

As described herein, the conjugation of water soluble fatty acid derivatives to therapeutic proteins can be catalyzed by aniline. Aniline strongly catalyzes aqueous reactions of aldehydes and ketones with amines to form stable imines such as hydrazones and oximes. The following diagram compares an uncatalyzed versus the aniline-catalyzed oxime ligation reaction (adapted from Kohler J J, ChemBioChem 2009; 10:2147-50).

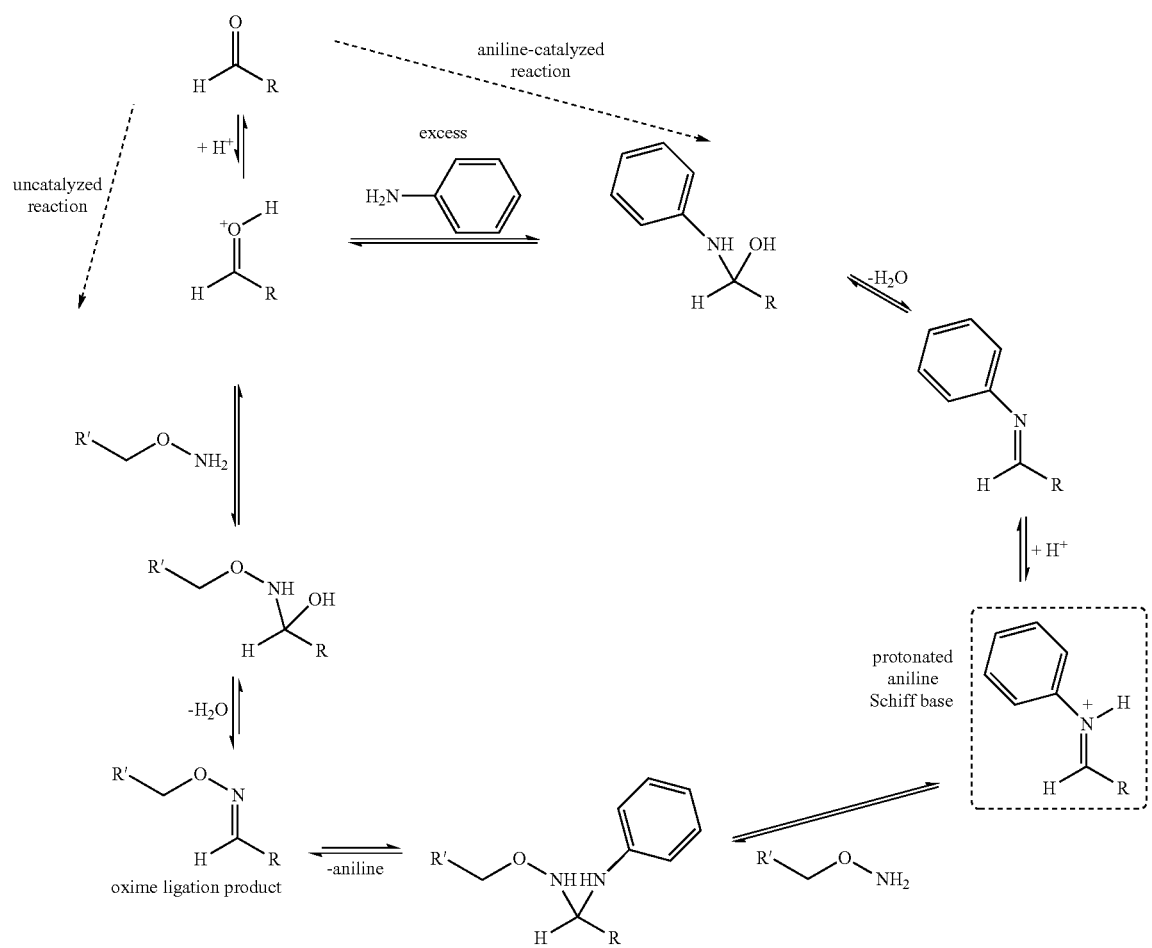

However, considering the numerous health risks associated with aniline; alternative catalysts are desirable. The present invention provides aniline derivatives as alternative oxime ligation catalysts. Such aniline derivatives include, but are not limited to, o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine. The following diagram compares an uncatalyzed versus the m-toluidine-catalyzed oxime ligation reaction (PCT/US2011/45873):

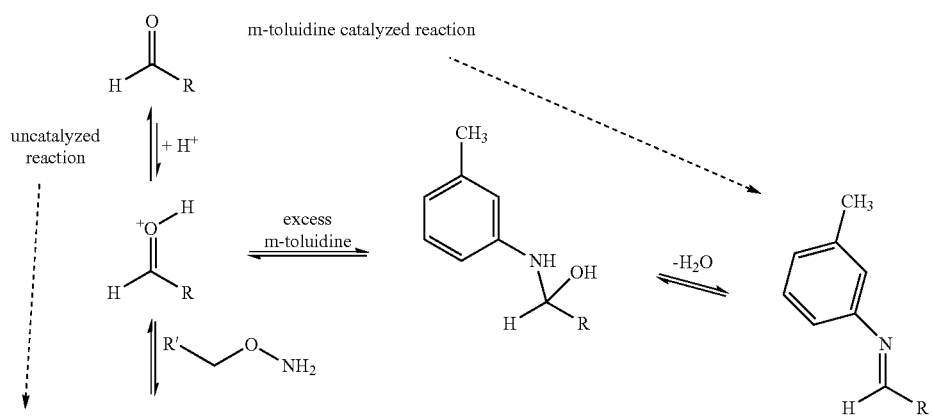

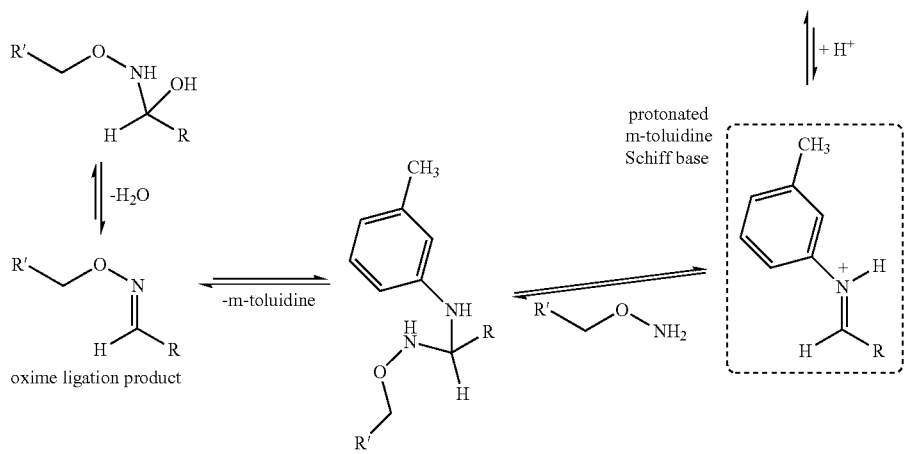

adapted from Kohler JJ. ChemBioChem 2009; 10: 2147-50

In one embodiment of the invention, m-toluidine (aka meta-toluidine, m-methylaniline, 3-methylaniline, or 3-amino-1-methylbenzene) is used to catalyze the conjugation reactions described herein. M-toluidine and aniline have similar physical properties and essentially the same pKa value (m-toluidine:pKa 4.73, aniline:pKa 4.63).

The nucleophilic catalysts of the invention are useful for oxime ligation (e.g., using aminooxy linkage) or hydrazone formation (e.g., using hydrazide chemistry). In various embodiments of the invention, the nucleophilic catalyst is provided in the conjugation reaction at a concentration of 0.1, 0.2, 0.3, 0.5, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15, 16, 17, 18, 19, 20, 25, 30, 35, 40, 45, or 50 mM. In one embodiment, the nucleophilic catalyst is provided between 1 to 10 mM. In various embodiments of the invention, the pH range of conjugation reaction is between 4.0 and 7.0, between 4.5 and 7.0, between 5.0 and 6.5, between 5.0 and 6.5. In various embodiments, the pH of the conjugation reaction is pH 4.5, 5.0, 5.5, 6.0, 6.5, 7.0 and 7.5. In one embodiment, the pH is between 5.5 to 6.5.

Purification of Conjugated Proteins

In various embodiments, purification of a protein that has been incubated with an oxidizing agent and/or a therapeutic protein that has been conjugated with a water soluble fatty acid derivative according to the invention, is desired. Numerous purification techniques are known in the art and include, without limitation, chromatographic methods, filtration methods, and precipitation methods (See, e.g., Guide to Protein Purification, Meth. Enzymology Vol 463 (edited by Burgess R R and Deutscher M P), 2nd edition, Academic Press 2009).

The following examples are not intended to be limiting but only exemplary of specific embodiments of the invention.

EXAMPLES

Example 1

Preparation of the homobifunctional linker $NH_2[OCH_2CH_2]_2ONH_2$

The homobifunctional linker $NH_2[OCH_2CH_2]_2ONH_2$

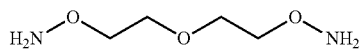

3oxapentane-1,5-dioxyamine containing two active aminooxy groups was synthesized according to Boturyn et al. (Tetrahedron 1997; 53:5485-92) in a two step organic reaction employing a modified Gabriel-Synthesis of primary amines (FIG. 1). In the first step one molecule of 2,2-dichlorodiethylether was reacted with two molecules of endo-N-hydroxy-5-norbornene-2,3-dicarbox imide in DMF. The desired homobifunctional product was prepared from the resulting intermediate by hydrazinolysis in ethanol.

Example 2

Preparation of the homobifunctional linker $NH_2[OCH_2CH_2]_6ONH_2$

The homobifunctional linker $NH_2[OCH_2CH_2]_6ONH_2$

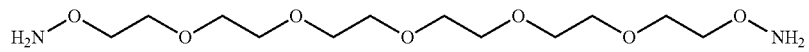

3,6,9,12,15-penatoxa-heptadecane-1,17-dioxyamine containing two active aminooxy groups was synthesized according to Boturyn et al. (Tetrahedron 1997; 53:5485-92) in a two step organic reaction employing a modified Gabriel-Synthesis of primary amines. In the first step one molecule of hexaethylene glycol dichloride was reacted with two molecules of endo-N-hydroxy-5-norbornene-2,3-dicarboximide in DMF. The desired homobifunctional product was prepared from the resulting intermediate by hydrazinolysis in ethanol.

Example 3

Preparation of the homobifunctional linker $NH_2[OCH_2CH_2]_4ONH_2$

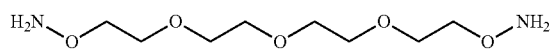 [SMILES: NOCCOCCOCCOCCON]

The homobifunctional linker $NH_2[OCH_2CH_2]_4ONH_2$ (3,6,9-Triaoxaundecane-1,11-dioxyamine) containing two active aminooxy groups was synthesized according to Boturyn et al. (Tetrahedron 1997; 53:5485-92) in a two step organic reaction employing a modified Gabriel-Synthesis of primary amines: In the first step one molecule bis-(2-(2-chloroethoxy)-ethyl)-ether was reacted with two molecules endo-N-hydroxy-5-norbornene-2,3-dicarboximide in DMF. The final homobifunctional product was prepared from the resulting intermediate by hydrazinolysis in ethanol.

Example 4

Preparation of 16-(2-(2-(2-(2-aminooxyethoxy)-ethoxy)-ethoxy)-ethoxyimino)-hexadecanoic Acid Sodium Salt The fatty acid-aminooxy linker 16-(2-(2-(2-(2-Aminooxyethoxy)-ethoxy)-ethoxy)-ethoxyimino)-hexadecanoic acid sodium salt was synthesized according to Halligan and Nair (Arkivoc 2006 (ii) 101-106) and Hubbs and Heathcock (J Am Chem Soc, 2003; 125:12836-43) in a two step reaction.

Intermediate 1: 16-oxohexadecanoic acid sodium salt

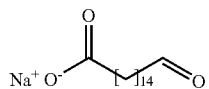

To a cooled solution (0° C.) of 16-hydroxyhexadecanoic acid (800 mg, 2.9 mmol) in dichloromethane (10 ml) and tetrahydrofurane (20 ml) Dess-Martin periodinane (1636 mg, 3.7 mmol) was added at 0° C. The mixture was stirred for 3.5 hrs at 0° C. and 2.5 hrs at room temperature under Ar-atmosphere. Then a 15%-solution of sodium thiosulfate in saturated sodium bicarbonate solution was added, the mixture was stirred at room temperature for 1.5 hrs. Intermediate 1 was extracted with diethylether, after drying over sodium sulfate the organic layer was evaporated to dryness and purified by column chromatography using silica gel as separating agent and a solvent mixture of toluene/ethylacetate. Yield: 34% (white solid).

Product: 16-(2-(2-(2-(2-aminooxyethoxy)-ethoxy)-ethoxy)-ethoxyimino)-hexadecanoic acid sodium salt

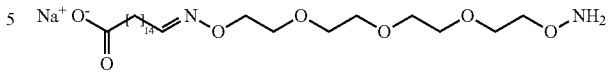

To a solution of 3,6,9-triaoxaundecane-1,11-dioxyamine (146 mg, 0.65 mmol) in anhydrous tetrahydrofurane (3 ml) Intermediate 1 (19.1 mg, 0.07 mmol) was added. The mixture was stirred for 1.5 hrs at room temperature under Ar-atmosphere. Then the mixture was evaporated to dryness and purified by column chromatography using silica gel as separating agent and a solvent mixture of dichloromethane/methanol/Huenig's base. Yield: 71% (white solid).

Mass spectrometry (ESI): m/z=477,3529 for $[M+2H]^+$

Example 5

Preparation of 16-(2-(2-(2-(2-aminooxyethoxy)-ethoxy)-ethoxy)-ethoxyamino)-hexadecanoic Acid Methyl Ester The fatty acid methyl ester-aminooxy linker 16-(2-(2-(2-(2-aminooxyethoxy)-ethoxy)-ethoxy)-ethoxyamino)-hexadecanoic acid methyl ester was synthesized according to Hang et al. (J Am Chem Soc 2007; 129:2744-5) in a three step reaction.

Intermediate 1: 16-hydroxyhexadecanoic acid methyl ester

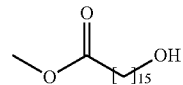

To a cooled (0° C.) solution of 16-hydroxyhexadecanoic acid (3000 mg, 10.79 mmol) in anhydrous methanol (27 ml) acetyl chloride (3.837 ml, 53.96 mmol) was added dropwise at 0° C. within 2 min, then the mixture was stirred at room temperature for 3.5 hrs under Ar-atmosphere. Subsequently the mixture was evaporated to dryness, the residue was dissolved in dichloromethane (100 ml), washed with saturated sodium bicarbonate solution (2×50 ml) and Brine solution (1×50 ml). After drying over sodium sulfate the collected organic layer was evaporated to dryness and vacuum dried at room temperature. Yield: 92% (white solid).

Intermediate 2: 16-methylsulfonylhexadecanoic acid methyl ester

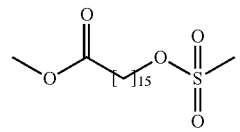

To a cooled solution (0° C.) of intermediate 1 (2807 mg, 9.80 mmol) in dichloromethane (40 ml) triethylamine (1.502 ml, 10.78 mmol) was added, then a precooled solution (0° C.) of mesyl chloride (0.834 ml, 10.78 mmol) in dichloromethane (5 ml) was added dropwise within 10 min at 0° C. The mixture was stirred for 30 min at 0° C. and for 2.75 hrs at room temperature. Then the mixture was diluted with dichloromethane (150 ml), washed with water (1×100 ml), saturated sodium bicarbonate solution (2×100 ml) and Brine solution (1×100 ml). After drying over sodium sulfate the collected organic layer was evaporated to dryness and vacuum dried at room temperature. Yield: 95% (white pale yellow solid).

Product: 16-(2-(2-(2-(2-aminooxyethoxy)-ethoxy)-ethoxy)-ethoxyamino)-hexa-decanoic acid methyl ester

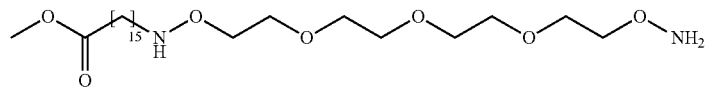

To a solution of 3,6,9-trioxaundecane-1,11-dioxyamine (517 mg, 2.30 mmol) in anhydrous N,N-dimethylformamide (22 ml) a solution of intermediate 2 (70 mg, 0.19 mmol) in anhydrous N,N-dimethylformamide (7 ml) was added dropwise for 1 hr at room temperature under Ar-atmosphere; the mixture was stirred for 2 days at different temperatures (room temperature, 50° C., 80° C.) to complete the reaction. Then the mixture was evaporated to dryness, the crude product was purified by column chromatography using silica gel as separating agent and a solvent mixture of dichloromethane/methanol. Yield: 31% (colorless partially solidified white oil).

Mass spectrometry (ESI): m/z=493,3824 for [M+H]$^+$

Example 6

Coupling of 16-(2-(2-(2-(2-aminooxyethoxy)-ethoxy)-ethoxy)-ethoxyamino)-hexa-decanoic acid methyl ester to the carbohydrate moiety of coagulation Factor VIII FA-rFVIII is prepared by using a two-step procedure. In the first step rFVIII is oxidized with NaIO$_4$ and purified by anion exchange chromatography (AEC). Subsequently the oxidized rFVIII is modified with the FA-aminoxy reagent.

rFVIII (45 mg starting material) is oxidized with NaIO$_4$ (final concentration 200 μM). After an incubation time of 30 minutes (22° C.), the oxidation reaction is stopped by adding an 1 M aqueous L-cysteine solution (final concentration: 10 mM). The oxidized rFVIII is purified by anion exchange chromatography on EMD TMAE(M). Then 25 μl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added to the eluate (protein concentration 2 mg/ml) and the coupling reaction is performed for 18 hours at 4° C. Then the FA-rFVIII conjugate is further purified by HIC on Phenyl Sepharose 4 FF. Finally the eluate is concentrated by UF/DF using a 30 kD membrane (MILLIPORE).

Example 7

Coupling of 16-(2-(2-(2-(2-aminooxyethoxy)-ethoxy)-ethoxy)-ethoxyamino)-hexa-decanoic acid methyl ester to the carbohydrate moiety of coagulation factor IX 10 mg rFIX is dissolved in reaction buffer (20 mM L-histidine, 5 mM CaCl$_2$, 150 mM NaCl, pH 6.0) to give a final concentration of 2.5 mg/ml. To this solution a 5 mM aqueous NaIO$_4$ solution was added to get a final concentration of 100 μM. The reaction mixture was incubated for 1 h at 4° C. under gentle stirring in the dark. Then the mixture is loaded onto a pre-equilibrated PD-10 desalting columns for removal of excess NaIO$_4$. To this mixture 8 μl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added and the coupling reaction is carried out at pH 6.0 for 18 h at 4° C. Then the conjugate is further purified by IEX on Q-Sepharose FF. Finally the eluate is concentrated by UF/DF using Vivaspin devices.

Example 8

Coupling of 16-(2-(2-(2-(2-aminooxyethoxy)-ethoxy)-ethoxy)-ethoxyamino)-hexa-decanoic acid methyl ester to the carbohydrate moiety of coagulation Factor VIIa 10 mg rFVIIa is dissolved in reaction buffer ((50 mM Hepes, 150 mM sodium chloride, 5 mM calcium chloride, pH 6.0) to give a final concentration of 2.0 mg/ml. To this solution a 5 mM aqueous NaIO$_4$ solution is added to get a final concentration of 50 μM. The reaction mixture is incubated for 1 h at 4° C. under gentle stirring in the dark. Then the mixture is loaded onto a pre-equilibrated PD-10 desalting columns for removal of excess NaIO$_4$. To this mixture 8 μl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added and the coupling reaction is carried out at pH 6.0 for 18 h at 4° C. Then the conjugate is further purified by IEX on Q-Sepharose FF. Finally the eluate is concentrated by UF/DF using Vivaspin devices.

Example 9

Coupling of 16-(2-(2-(2-(2-aminooxyethoxy)-ethoxy)-ethoxy)-ethoxyamino)-hexa-decanoic acid methyl ester to the carbohydrate moiety of coagulation factor VIII 10 mg rFVIII are dissolved in Hepes-buffer (50 mM Hepes, 150 mM NaCl, 5 mM calcium chloride, pH 6.0) to give a protein concentration of 2 mg/ml. Then 10 μl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added to the FVIII solution. Subsequently an aqueous solution of the nucleophilic catalyst m-toluidine (50 mM) is prepared and added to the mixture within 15 minutes to get a final concentration of 10 mM. Finally a 40 mM aqueous sodium periodate solution is added to give a concentration of 400 μM. The reaction mixture is incubated for 120 minutes in the dark at a temperature of 22° C. under gentle stirring. Then the reaction is stopped by the addition of an aqueous L-cysteine solution (1 M) to give a final concentration of 10 mM in the reaction mixture and incubation for 60 min. Subsequently the reaction mixture is loaded onto an IEX column filled with Q-Sepharose FF (1.6×8 cm). The column is washed with 20 column volumes equilibration buffer (20 mM Hepes, 5 mM CaCl$_2$, pH 7.4) and the FA-rFVIII conjugate is eluted with buffer B (20 mM Hepes, 5. mM CaCl$_2$, 0.5 M NaCl, pH 7.4).

Finally the product is subjected to UF/DF with Vivaspin devices using Hepes buffer, 7.4 (20 mM Hepes, 150 mM NaCl, 5 mM $CaCl_2$, pH 7.4) as diafiltration buffer.

Example 10

Coupling of 16-(2-(2-(2-(2-aminooxyethoxy)-ethoxy)-ethoxy)-ethoxyamino)-hexa-decanoic acid methyl ester to the carbohydrate moiety of coagulation factor IX 7 mg rFIX are dissolved in His-buffer (20 mM His, 150 mM NaCl, 5 mM $CaCl_2$, pH 6.0) to give a protein concentration of 2 mg/ml. Then 7 µl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added to the FIX solution. Then an aqueous solution of the nucleophilic catalyst m-toluidine (50 mM) is prepared and added to the mixture within 15 minutes to get a final concentration of 10 mM. Finally a 40 mM aqueous sodium periodate solution is added to give a concentration of 250 µM. The reaction mixture is incubated for 120 minutes in the dark at a temperature of 22° C. under gentle stirring. Subsequently the reaction is quenched by the addition of L-cysteine (final concentration: 5 mM) for 30 min at room temperature.

The FA-rFIX conjugate is purified by anion exchange chromatography. The reaction mixture is diluted with 10 ml buffer A (50 mM Hepes, 5 mM $CaCl_2$, pH 7.5) and loaded onto a 5 ml HiTrap Q FF column (GE Healthcare, Fairfield, Conn.) equilibrated with buffer A. The column is washed with 5 CV using the same buffer. Then the column is eluted with buffer B (50 mM Hepes, 1 M NaCl, 5 mM $CaCl_2$, pH 7.5). The conjugate containing fractions are concentrated by UF/DF using a 10 kD membrane made of regenerated cellulose. The final diafiltration step is performed against 20 mM Hepes buffer, pH 7.2 containing 150 mM NaCl and 5 mM $CaCl_2$.

Example 11

Coupling of 16-(2-(2-(2-(2-aminooxyethoxy)-ethoxy)-ethoxy)-ethoxyamino)-hexa-decanoic acid methyl ester to the carbohydrate moiety of coagulation factor VIIA 10 mg rFVIIa are dissolved in Hepes buffer (50 mM Hepes, 150 mM sodium chloride, 5 mM calcium chloride, pH 6.0). Then 10 µl of a 10% (w/v) solution of 16-(2-(2-(2-(2-aminooxyethoxy)-ethoxy)-ethoxy)-ethoxyamino)-hexa-decanoic acid methyl ester (prepared according to Example 3) in DMSO is added to the FVIIa solution. Subsequently an aqueous solution of the nucleophilic catalyst m-toluidine (50 mM) is prepared and added to the mixture within 15 minutes to get a final concentration of 10 mM. Finally a 40 mM aqueous sodium periodate solution is added to give a concentration of 250 µM. The reaction mixture is incubated for 120 minutes in the dark at a temperature of 22° C. under gentle stirring. Subsequently the reaction is quenched by the addition of L-cysteine (final concentration: 5 mM) for 30 min at room temperature. The FA-rFVIIa conjugate is purified by anion exchange chromatography. The reaction mixture is diluted with 10 ml buffer A (50 mM Hepes, pH 7.4) and loaded onto a 5 ml HiTrap Q FF column (GE Healthcare, Fairfield, Conn.) equilibrated with buffer A. The column is washed with 5 CV using the same buffer. Then the column is eluted with buffer B (50 mM Hepes, 1 M NaCl, 5 mM $CaCl_2$, pH 7.4). The conjugate containing fractions are concentrated by UF/DF using a 10 kD membrane made of regenerated cellulose. The final diafiltration step is performed against 20 mM Hepes buffer, pH 7.2 containing 150 mM NaCl and 5 mM $CaCl_2$.

Example 12

Coupling of a FA Derivative Containing an Active Aminooxy Group to an Oxidized Carbohydrate Moiety in the Presence of a Nucleophilic Catalyst The coupling of a FA derivative containing an active aminooxy group to an oxidized therapeutic protein (such as the proteins set out in Table 1 herein) is also provided.

For coupling of a FA derivative containing an aminooxy group, the carbohydrate moieties (predominantly N-glycans) of a therapeutic protein (e.g., EPO, G-CSF, or insulin; see Table 1; concentration: 0.5-3 mg/ml) are first oxidized with $NaIO_4$ (concentration: 200 µM). Then the reaction is stopped by addition of L-cysteine (final concentration: 5 mM) and the reagents are separated by UF/DF. After diafiltration the FA aminooxy reagent (i.e., the FA derivative) is added using a 25 M excess and the coupling reaction is performed at pH 6.0 for 1 hour at room temperature under gentle stirring in the presence of the nucleophilic catalyst m-toluidine (concentration: 10 mM). Subsequently the reaction mixture is loaded onto an ion exchange (IEX) column. The column is washed with >5 CV washing buffer and the conjugate is eluted with a linear NaCl gradient. Finally the conjugate containing fractions are subjected to UF/DF.

Example 13

Coupling of a FA Derivative Containing an Active Aminooxy Group to an Oxidized Carbohydrate Moiety in the Presence of a Nucleophilic Catalyst For coupling of a FA derivative containing an aminooxy group to the carbohydrate moiety of a therapeutic protein the protein (e.g., EPO, G-CSF, or insulin; see Table 1; concentration: 0.5-3 mg/ml) is incubated at pH 6.0 with $NaIO_4$ (concentration: 300 µM) for 1 hour at room temperature in the presence of the nucleophilic catalyst m-toluidine (concentration: 10 mM). Then the reaction is stopped by addition of L-cysteine (final concentration: 5 mM) and the reaction mixture is loaded onto an ion exchange (IEX) column. The column is washed with >5 CV washing buffer and the conjugate is eluted with a linear NaCl gradient. Finally the conjugate containing fractions are subjected to UF/DF.

Example 14

Coupling of a FA Derivative Containing an Active Aminooxy Group to an Oxidized Blood Coagulation Protein in the Presence of a Nucleophilic Catalyst The coupling of a FA derivative containing an active aminooxy group to an oxidized blood coagulation protein (such as FIX, FVIII and FVIIa as described in the above examples) may be carried out in the presence of a nucleophilic catalyst such as m-toluidine in a concentration range of 2-20 mM.

Example 15

Preparation of a Water Soluble MAL Fatty Acid Linker

A fatty acid linker containing a water soluble PEG chain in ω-position and an active MAL group is prepared in a two-step synthesis:

Step 1: Preparation of 16-hydroxyhexadecanoic acid methyl ester:

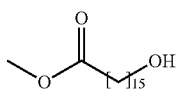

Commercially available 16-hydroxyhexadecanoic acid is esterified with acetyl chloride in methanol for 5 hrs at room temperature according to Example 3 to give the corresponding methyl ester (Hang et al., Chemical probes for the rapid detection of fatty-acylated proteins in mammalian cells, JACS 2007; 129:2744-5).

Step 2: Preparation of the MAL fatty acid linker:

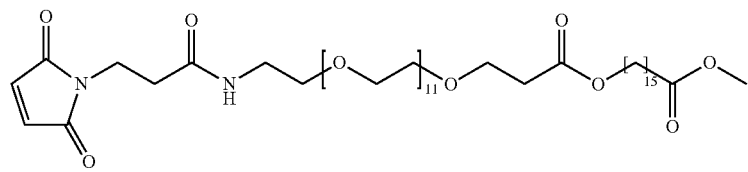

16-hydroxyhexadecanoic acid methyl ester is reacted with commercially available MAL-PEG-COOH (mal-Peg(12)-COOH/IRIS Biotech GmbH, Marktredwitz, Germany) employing a Mitsunobu reaction in THF at room temperature over night (Toyokuni et al., Synthesis of a New Heterobifunctional Linker, N-[4-(Aminooxy)butyl]-maleimide, for Facile Access to a Thiol-Reactive 18F-Labeling Agent, Bioconjugate Chem 2003; 14:1253-9).

Example 16

Preparation of a Water Soluble NHS Fatty Acid Linker

A fatty acid linker containing a water soluble PEG chain in ω-position and a terminal active NHS ester is prepared by use of a four-step synthesis:

Step 1: Preparation of 16-bromohexadecanoic Acid Methyl Ester

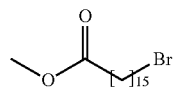

Commercially available 16-bromohexadecanoic acid is esterified with methanol and catalytic amount of concentrated sulfuric acid over night at reflux temperature to give the corresponding methyl ester (Zinic et al., Positionally Isomeric Organic Gelators: Structure-Gelation Study, Racemic versus Enantiomeric Gelators, and Solvation Effects, Chem Eur J 2010; 16:3066-82).

Step 2: Preparation of 16-azidohexadecanoic Acid Methyl Ester

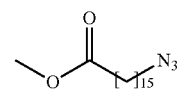

16-bromohexadecanoic acid methyl ester is reacted with sodium azide in acetonitrile for four days at reflux temperature to give the corresponding azide (Zinic et al., Positionally Isomeric Organic Gelators: Structure-Gelation Study, Racemic versus Enantiomeric Gelators, and Solvation Effects, Chem. Eur. J. 2010; 16:3066-82).

Step 3: Preparation of 16-aminohexadecanoic acid methyl ester

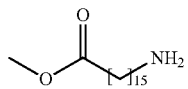

16-azidohexadecanoic acid methyl ester is catalytically hydrogenated with palladium/activated charcoal in methanol at 3 bar for three hours to give the corresponding amine (Zinic et al., Positionally Isomeric Organic Gelators: Structure-Gelation Study, Racemic versus Enantiomeric Gelators, and Solvation Effects, Chem. Eur. J. 2010; 16:3066-82).

Step 4: Preparation of the NHS fatty acid linker

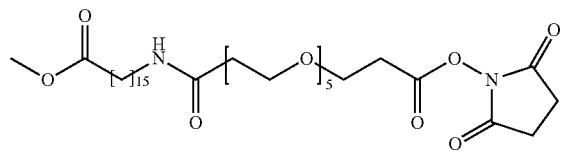

16-aminohexadecanoic acid methyl ester is reacted with commercially available NHS-PEG-NHS (NHS-dPEG(4)-NHS/IRIS Biotech GmbH, Marktredwitz, Germany) in 1,4-dioxane at room temperature for three days to give the NHS fatty acid linker (Cline et al., The Aminolysis of N-Hydroxysuccinimide Esters. A Structure-Reactivity Study, JACS 1987; 109:3087-91).

Example 17

Analytical Characterization of Protein FA Conjugates

The albumin binding properties of the FA-rFVIII, rFIX or FVIIa samples prepared according to the examples herein are verified in vitro by use of Enzyme Linked Immunosorbent Assay (ELISA) systems. A 96 well plate is coated with a polyclonal antibody directed against human serum albumin (HSA). The next step is the blocking of the ELISA plate with a PBS-gelatine buffer. Then HSA is bound to the antibody followed by binding of the FA-protein sample, which is diluted to different concentrations. Finally the HSA-protein sample is detected by a peroxidase labeled anti-VIII, anti-FIX or anti FVIIa antibody. Peroxidase activity is detected by using tetramethyl-benzidine (TMB) as substrate. The developed color intensity is measured with an ELISA reader at 450 nm. The binding of the FA-protein sample to HSA is evaluated by plotting the different sample concentrations on the x-axis and their corresponding'absorbance values on the y-axis.

Example 18

Preparation of a Water Soluble PEGylated Fatty Acid Linker Containing an Aminooxy Group A fatty acid linker containing a water soluble PEG chain with an aminooxy moiety at the ω-position connected to the fatty acid carboxyl group is prepared in a three step synthesis using 3-oxapentane-1,5-dioxyamine as described in Example 1.

Step 1: Preparation of N-(9-fluorenylmethoxycarbonyl)-3-oxapentane-1,5-dioxyamine

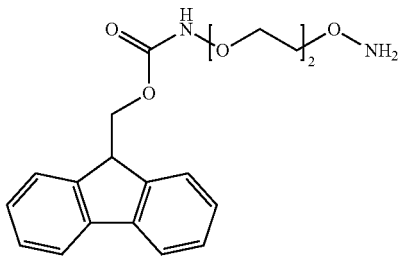

3-oxapentane-1,5-dioxyamine was reacted with 9-fluorenylmethylchloroformate in 1,4-dioxane at ambient temperature for 1 hour. The solution was evaporated under reduced pressure and the crude product was purified employing silica gel chromatography with dichloromethane/methanol 20/1 (v/v) as the solvent mixture to give pure mono-FMOC protected dioxyamine (Boturyn et al., Synthesis of Fluorescent Probes for the Detection of Abasic Sites in DNA, Tetrahedron 1997; Vol. 53, No. 15, 5485-92).

Step 2: Preparation of hexadecanoic acid (2-(2-(N-(9-fluorenylmethoxycarbonyl)aminooxy)ethoxy)ethoxy) amide

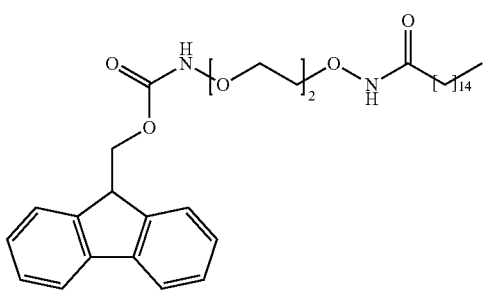

N-(9-fluorenylmethoxycarbonyl)-3-oxapentane-1,5-dioxyamine is reacted with commercially available palmitic acid N-hydroxysuccinimide ester in THF at ambient temperature over night to give the mono-FMOC protected aminooxy-fatty acid conjugate (Jong et al., Synthesis of ceramides using N-hydroxysuccinimide esters, Journal of Lipid Research 1972; Vol. 13, 819-22).

Step 3: Preparation of Hexadecanoic Acid (2-(2-aminooxyethoxy)ethoxy)amide

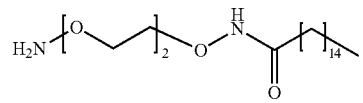

Mono-FMOC protected aminooxy-fatty acid conjugate is reacted with Piperidine in dichloromethane at ambient temperature to give the deprotected aminooxy-fatty acid linker as the final product (Boturyn et al., Synthesis of Fluorescent Probes for the Detection of Abasic Sites in DNA, Tetrahedron 1997; Vol. 53, No. 15, 5485-92).

Example 19

Coupling of a MAL fatty acid linker with A1PI

A fatty acid linker containing a MAL group is prepared as described in Example 15 by reaction of 16-hydroxyhexadecanoic acid methyl ester with commercially available MAL-PEG-COOH (mal-Peg(12)-COOH/IRIS Biotech GmbH, Marktredwitz, Germany) employing a Mitsunobu reaction. This linker is coupled to the free SH-group of A1PI.

10 mg of purified A1PI (concentration: 1 mg/ml) is dissolved in reaction buffer (20 mM phosphate, 5 mM EDTA, pH 7.0) and 10 µL of a 5% (w/v) solution of the MAL fatty acid linker in DMSO is added to the A1PI solution. The modification reaction is performed for 2 hours at room temperature followed by a quenching step using L-cysteine (final concentration: 10 mM). After the addition of L-cysteine the reaction mixture is incubated under gentle shaking for an additional hour at the same temperature. The modified A1PI is diluted with equilibration buffer (25 mM phosphate, pH 6.5) to correct the solutions conductivity to <4.5 mS/cm and loaded onto a pre-packed HiTrap Q FF (GE-Healthcare) with a column volume (CV) of 5 ml. Then the column is equilibrated with 10 CV equilibration buffer (flow rate: 2 ml/min). Finally the PEG-A1PI is eluted with a linear gradient with elution buffer (25 mM $Na_2HPO_4$. 1 M NaCl, pH 6.5).

Example 20

Coupling of a NHS Fatty Acid Linker With Coagulation Factor VIII

A fatty acid linker containing a NHS group is prepared as described in Example 16 by reaction of 16-hydroxyhexadecanoic acid methyl ester with commercially available NHS-PEG-NHS (NHS-dPEG(4)-NHS (IRIS Biotech GmbH, Marktredwitz, Germany). This linker is coupled to the free amino groups of lysine residues of coagulation factor VIII.

10 mg rFVIII is dissolved in Hepes-buffer (50 mM Hepes, 150 mM NaCl, 5 mM calcium chloride, pH 6.0) to give a protein concentration of 2 mg/ml. Then 10 µl of a 10% (w/v) solution of NHS fatty acid linker in DMSO is added to the FVIII solution. The reaction mixture is incubated for 120 minutes in the dark at a temperature of 22° C. under gentle stirring. Then the reaction is stopped by the addition of an aqueous glycine solution (1 M) to give a final concentration of 20 mM in the reaction mixture. The mixture is incubated for 15 min at room temperature under gentle stirring and subsequently loaded onto an IEX column filled with Q-Sepharose FF (1.6×8 cm). The column is washed with 20 column volumes equilibration buffer (20 mM Hepes, 5 mM CaCl$_2$, pH 7.4) and the FA-rFVIII conjugate is eluted with buffer B (20 mM Hepes, 5 mM CaCl$_2$, 0.5 M NaCl, pH 7.4). Finally the product is subjected to UF/DF with Vivaspin devices using Hepes buffer, 7.4 (20 mM Hepes, 150 mM NaCl, 5 mM CaCl$_2$, pH 7.4) as diafiltration buffer.

The invention claimed is:

1. A water soluble fatty acid derivative comprising a fatty acid or fatty acid ester attached to a water soluble linker, said fatty acid derivative stably attached to a therapeutic protein, wherein the water soluble linker comprises a water soluble polymer, at least one first functional group attached to the therapeutic protein, wherein the first functional group is an aminooxy group, and a second functional group attached to the fatty acid or fatty acid ester, wherein the second functional group is an aminooxy group.

2. The fatty acid derivative according to claim 1 that binds human serum albumin (HSA) in vitro or in vivo, has increased half-life relative to a native therapeutic protein, and wherein the fatty acid is a saturated fatty acid or unsaturated fatty acid.

3. The fatty acid derivative of claim 2 wherein the fatty acid is a branched chain fatty acid.

4. The fatty acid derivative according to claim 1 wherein the fatty acid comprises a chain length selected from the group consisting of C10, C12, C14, C16, C18, C20, C22, and C24.

5. The fatty acid derivative according to claim 1 wherein the fatty acid is attached to the water soluble linker at a group on the fatty acid selected from the group consisting of: terminal carboxyl group and ω-group, wherein the ω-group is selected from the group consisting of: hydroxyl, amino, thio, and carboxyl.

6. The fatty acid derivative according to claim 1 wherein the fatty acid is 16-hydroxyhexadecanoic acid.

7. The fatty acid derivative according claim 1 wherein the fatty acid ester is selected from the group consisting of: methyl ester and ethyl ester.

8. The fatty acid derivative of claim 7 wherein the fatty acid ester is 16-hydroxyhexadecanoic acid methyl ester.

9. The fatty acid derivative according to claim 1 wherein the water soluble polymer is selected from the group consisting of: polyethylene glycol (PEG), branched PEG, polysialic acid (PSA), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC).

10. The fatty acid derivative according to claim 9 wherein the water soluble polymer is PEG and comprises a chain length selected from the group consisting of O3, O5, O7, O9, O11, O13 and O15.

11. The fatty acid derivative according to claim 10 wherein the water soluble linker is selected from the group consisting of:

a) 3-oxapentane-1,5-dioxyamine of the formula:

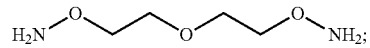

b) 3,6,9-triaoxaundecane-1,11-dioxyamine of the formula:

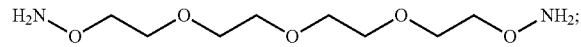 [SMILES: NOCCOCCOCCOCCON]

c) 3,6,9,12,15-penatoxaheptadecane-1,17-dioxyamine of the formula:

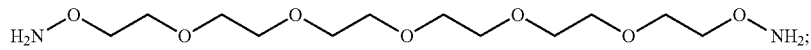 [SMILES: NOCCOCCOCCOCCOCCOCCON]

and d) 3,6,9,12,15,18,21-heptaoxatricosane-1,23-dioxyamine of the formula:

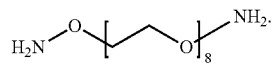

12. The fatty acid derivative according to claim 1 wherein the fatty acid derivative is stably attached to the therapeutic protein by an oxime linkage, wherein the oxime linkage is formed between an oxime group on the water soluble linker and an aldehyde group of an oxidized carbohydrate on the therapeutic protein.

13. The fatty acid derivative according to claim 1 wherein the fatty acid derivative is selected from the group consisting of:

a) 16-(2-(2-(2-(2-aminooxyethoxy)-ethoxy)-ethoxy)-ethoxyimino)-hexadecanoic acid sodium salt of the formula:

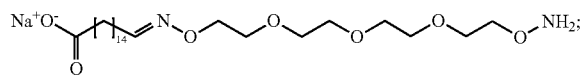

and
b) 16-(2-(2-(2-(2-aminooxyethoxy)-ethoxy)-ethoxy)-ethoxyamino)-hexadecanoic acid methyl ester,

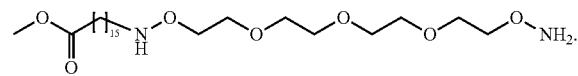

14. The fatty acid derivative according claim 1 wherein the therapeutic protein is selected from the group consisting of: Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11 bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor α, transforming growth factor β, transforming growth factor β1, transforming growth factor β1.2, transforming growth factor β1, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, adalimumab, denosumab, etanercept, and a protein in Table 1.

15. The fatty acid derivative of claim 14 wherein the therapeutic protein is FVIIa.

16. The fatty acid derivative of claim 14 wherein the therapeutic protein is FVIII.

17. The fatty acid derivative of claim 14 wherein the therapeutic protein is FIX.

18. A method of preparing a fatty acid derivative according to claim 1 comprising:
  a) oxidizing an ω-hydroxy group on a fatty acid to generate an aldehyde group on the fatty acid; and
  b) coupling a water soluble linker comprising an active aminooxy group to the aldehyde group to form a stable oxime linkage;
  wherein said fatty acid derivative is water soluble;
  wherein the ω-hydroxy group is oxidized by an oxidation reagent selected from the group consisting of: Dess Martin periodinane reagent, Tempo reagent, oxalyl chloride/DMSO, tetrapropylammoniumperruthenate (TPAP) and crome VI reagents (Collins reagent, pyridinium chloro chromate (PCC) and pyridinium dichromate);
  wherein the fatty acid is a saturated fatty acid or unsaturated fatty acid.

19. The method of claim 18 wherein the fatty acid is a branched chain fatty acid.

20. The method according to claim 18 wherein the fatty acid comprises a chain length selected from the group consisting of C10, C12, C14, C16, C18, C20, C22, and C24.

21. The method according to claim 20 wherein the fatty acid is 16-hydroxyhexadecanoic acid.

22. The method according to claim 18 wherein the water soluble linker comprises a water soluble polymer and at least one aminooxy group, wherein the water soluble polymer is selected from the group consisting of: polyethylene glycol (PEG), branched PEG, polysialic acid (PSA), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC).

23. The method according to claim 22 wherein the water soluble polymer is PEG and comprises a chain length selected from the group consisting of O3, O5, O7, O9, O11, O13 and O15.

24. The method of claim 23 wherein the water soluble linker is selected from the group consisting of:
  a) 3-oxapentane-1,5-dioxyamine of the formula:

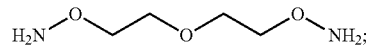

b) 3,6,9-triaoxaundecane-1,11-dioxyamine of the formula:

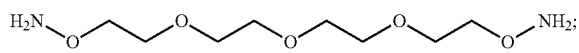 [SMILES: NOCCOCCOCCOCCON]

c) 3,6,9,12,15-penatoxaheptadecane-1,17-dioxyamine of the formula:

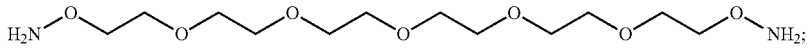

and
d) 3,6,9,12,15,18,21-heptaoxatricosane-1,23-dioxyamine of the formula:

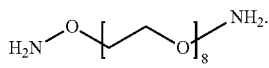

25. A method of preparing a fatty acid derivative according to claim 1 comprising:
    a) esterifying a carboxyl group on a fatty acid to generate an ester on the fatty acid;
    b) activating an ω-hydroxy group on a fatty acid to generate a mesyl group on the fatty acid of step a); and
    c) coupling a water soluble linker comprising an active aminooxy group by substituting the mesyl group of step b) thereby forming a stable oxyimine-methylene bond;
    wherein said fatty acid derivative is water soluble; wherein the carboxyl group is esterified by an esterifying agent selected from the group consisting of: acetyl chloride, methanol in the presence of acid, ethanol in the presence of acid, diazomethane, and methyliodide; wherein the ω-hydroxy group is activated by an activating agent selected from the group consisting of: mesyl chloride, tosyl chloride and nosyl chloride; and wherein the fatty acid is a saturated fatty acid or unsaturated fatty acid.

26. The method of claim 25 wherein the fatty acid is a branched chain fatty acid.

27. The method according to claim 25 wherein the fatty acid comprises a chain length selected from the group consisting of C10, C12, C14, C16, C18, C20, C22, and C24.

28. The method according to claim 27 wherein the fatty acid is 16-hydroxyhexadecanoic acid.

29. The method according to claim 25 wherein the water soluble linker comprises a water soluble polymer selected from the group consisting of:
    polyethylene glycol (PEG), branched PEG, polysialic acid (PSA), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), and 2-methacryloyloxy-2'-ethyltrimethylammoniumphosphate (MPC).

30. The method according to claim 29 wherein the water soluble polymer comprises is PEG and a chain length selected from the group consisting of O3, O5, O7, O9, O11, O13 and O15.

31. The method of claim 30 wherein the water soluble linker is selected from the group consisting of:
    a) 3-oxapentane-1,5-dioxyamine of the formula:

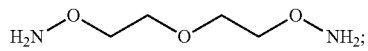

b) 3,6,9-triaoxaundecane-1,11-dioxyamine of the formula:

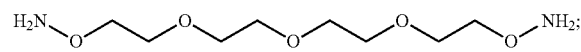 [SMILES: NOCCOCCOCCOCCON]

c) 3,6,9,12,15-penatoxaheptadecane-1,17-dioxyamine of the formula:

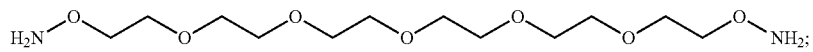

and
    d) 3,6,9,12,15,18,21-heptaoxatricosane-1,23-dioxyamine of the formula:

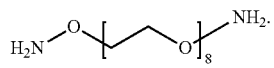

32. A method of preparing a conjugated therapeutic protein comprising contacting an oxidized carbohydrate moiety on the therapeutic protein with a fatty acid derivative according to claim 1 under conditions that allow conjugation;
    said carbohydrate moiety oxidized by incubation with a buffer comprising an oxidizing agent selected from the group consisting of sodium periodate ($NaIO_4$), lead tetraacetate ($Pb(OAc)_4$) and potassium perruthenate ($KRuO_4$);
    wherein an oxime linkage is formed between the oxidized carbohydrate moiety and an active aminooxy group on the fatty acid derivative;
    and wherein said oxime linkage formation is catalyzed by a nucleophilic catalyst selected from the group consisting of aniline, o-amino benzoic acid, m-amino benzoic acid, p-amino benzoic acid, sulfanilic acid, o-aminobenzamide, o-toluidine, m-toluidine, p-toluidine, o-anisidine, m-anisidine, and p-anisidine.

33. The method according to claim 32 wherein the therapeutic protein is selected from the group consisting of: Factor IX (FIX), Factor VIII (FVIII), Factor VIIa (FVIIa), von Willebrand Factor (VWF), Factor FV (FV), Factor X (FX), Factor XI (FXI), Factor XII (FXII), thrombin (FIT), protein C, protein S, tPA, PAI-1, tissue factor (TF), ADAMTS 13 protease, IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IFN-omega, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein α, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, adalimumab, denosumab, etanercept, and a protein in Table 1.

34. The method according to claim 33 wherein the therapeutic protein is FVIIa.

35. The method according to claim 33 wherein the therapeutic protein is FVIII.

36. The method according to claim 33 wherein the therapeutic protein is FIX.

37. The method according to claim 18 wherein the oxidation reagent is Dess Martin periodinane.

* * * * *